(12) United States Patent
Kotou et al.

(10) Patent No.: US 10,093,688 B2
(45) Date of Patent: Oct. 9, 2018

(54) NON-AQUEOUS LIQUID ELECTROLYTE, ELECTRICITY STORAGE DEVICE USING SAME, AND PHOSPHORUS COMPOUND USED THEREIN

(71) Applicant: UBE INDUSTRIES, LTD., Ube-shi (JP)

(72) Inventors: Yuichi Kotou, Takaishi (JP); Tatsuo Fujino, Ube (JP); Kei Shimamoto, Izumiotsu (JP); Shuichi Koso, Yamaguchi (JP); Shoji Shikita, Izumiotsu (JP); Yosuke Sato, Shimonoseki (JP); Junichi Chika, Ube (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 0 days.

(21) Appl. No.: 15/506,174

(22) PCT Filed: May 19, 2015

(86) PCT No.: PCT/JP2015/064377
§ 371 (c)(1),
(2) Date: Feb. 23, 2017

(87) PCT Pub. No.: WO2016/031316
PCT Pub. Date: Mar. 3, 2016

(65) Prior Publication Data
US 2017/0275311 A1 Sep. 28, 2017

(30) Foreign Application Priority Data

Aug. 25, 2014 (JP) ................................ 2014-170755
Feb. 20, 2015 (JP) ................................ 2015-031732
Feb. 20, 2015 (JP) ................................ 2015-031758

(51) Int. Cl.
*C07F 9/113* (2006.01)
*C07F 9/12* (2006.01)
*C07F 9/117* (2006.01)
*C07D 207/444* (2006.01)
*C07D 309/32* (2006.01)
*H01M 10/0525* (2010.01)
*H01M 10/0567* (2010.01)
*H01M 10/0569* (2010.01)
*C07F 1/02* (2006.01)

(52) U.S. Cl.
CPC .......... *C07F 9/113* (2013.01); *C07D 207/444* (2013.01); *C07D 309/32* (2013.01); *C07F 9/12* (2013.01); *H01M 10/0525* (2013.01); *H01M 10/0567* (2013.01); *H01M 10/0569* (2013.01); *C07F 1/02* (2013.01); *C07F 9/117* (2013.01)

(58) Field of Classification Search
CPC ......... H01M 10/0566; H01M 10/0567; H01M 10/0568; H01M 10/0525; H01M 10/0569; C07F 9/113; C07F 1/02; C07D 207/444; C07D 309/32; C07D 9/117; C07D 9/12
See application file for complete search history.

(56) References Cited

U.S. PATENT DOCUMENTS 3,943,201 A * 3/1976 McIntosh .............. C07F 9/4065
504/175
T986,003 I4 * 9/1979 Barrier ................... A01N 57/18
504/198

(Continued)

FOREIGN PATENT DOCUMENTS

JP 2730983 B2 12/1997
JP 2008-300081 A 12/2008

(Continued)

OTHER PUBLICATIONS

Montel, S., Midrier, C., Volle, J-N, Braun, R., Haaf, K., Willms, L., Pirat, J-L, Virieux, D—Functionalized Phosphanyl-Phosphonic Acids as Unusual Complexing Units as Analogues of Fosmidomycin, Eur. J.Org. Chem., 2012, pp. 3237-3248 (Year: 2012).*

(Continued)

*Primary Examiner* — Anca Eoff
(74) *Attorney, Agent, or Firm* — Oblon, McClelland, Maier & Neustadt, L.L.P.

(57) ABSTRACT

A nonaqueous electrolytic solution having an electrolyte salt dissolved in a nonaqueous solvent, containing a compound of formula (X):

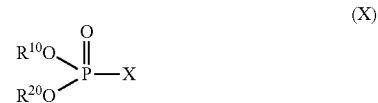

where $R^{10}$ and $R^{20}$ are each a group selected from an alkyl having 1 to 8 carbon atoms, an alkenyl having 2 to 6 carbon atoms, an alkynyl having 3 to 6 carbon atoms, and an aryl having 6 to 12 carbon atoms, or a lithium; and X is a polar group (i) containing a —C(═O), a —P(═O), or an —S(═O)$_2$ group, a polar group (ii) containing a —CN or an alkyl group having 1 to 6 carbon atoms, in which a part of hydrogen atoms is substituted with a fluorine atom, or a 4- to 7-membered ring polar group (iii) containing a —C(═O)—O— or a —C(═O)—N— group, where when X is a 4- to 7-membered ring polar group (iii) containing —C(═O)—N—, at least one of $R^{10}$ and $R^{20}$ is lithium.

22 Claims, No Drawings

(56) References Cited

U.S. PATENT DOCUMENTS

| | | | | |
|---|---|---|---|---|
| 8,574,773 | B2* | 11/2013 | Wilson | H01M 6/168 429/200 |
| 2010/0035147 | A1* | 2/2010 | Kotato | H01M 10/052 429/203 |
| 2013/0129595 | A1 | 5/2013 | Schulz et al. | |
| 2014/0134479 | A1* | 5/2014 | Kim | H01M 10/0567 429/200 |

FOREIGN PATENT DOCUMENTS

| | | |
|---|---|---|
| JP | 2010-282836 A | 12/2010 |
| JP | 2013-109930 A | 6/2013 |
| JP | 2013-534205 A | 9/2013 |
| JP | 2015-18713 A | 1/2015 |
| WO | WO 2008/123038 A1 | 10/2008 |
| WO | WO 2012/067248 A1 | 5/2012 |
| WO | WO 2013/168716 A1 | 11/2013 |

OTHER PUBLICATIONS

Moss, R.A., Gong, P.K.—Proton exchange and chemoselectivity in metal cation and hydroxide ion hydrolyses of phosphonoacetate diesters, Tetrahedron Letters, 44 (2003), pp. 7845-7848 (Year: 2003).*

Voncken, W.G., Castelijns, A.M.C.F., de Leeuw, S.A.J., Buck, H.M.—Group Transfer Reactions via Pentavalent Phosphorus Intermediates, Tetrahedron Letters No. 8, pp. 729-732, 1977 (Year: 1977).*

Kinzhybalo et al., "Electron density distribution in tetralithium hypodiphosphate hexahydrate, $Li_4P_2O_6 \cdot 6H_2O$", Structural Science, Crystal Engineering and Materials, Acta Crystallographica Section 8, B69, vol. 69 (2013), pp. 344-355.

* cited by examiner

NON-AQUEOUS LIQUID ELECTROLYTE, ELECTRICITY STORAGE DEVICE USING SAME, AND PHOSPHORUS COMPOUND USED THEREIN

TECHNICAL FIELD

The present invention relates to a nonaqueous electrolytic solution capable of improving electrochemical characteristics in a broad temperature range, an energy storage device using the same, and a novel phosphorus compound in which a polar group is bound to a phosphorus atom.

BACKGROUND ART

An energy storage device, especially a lithium secondary battery, has been widely used recently for a power source of a small-sized electronic device, such as a mobile telephone, a notebook personal computer, etc., and a power source for an electric vehicle or electric power storage. There is a possibility that such an electronic device or vehicle is used in a broad temperature range, such as a high temperature in the midsummer, a low temperature in the coldest season, etc., and therefore, it is required to improve electrochemical characteristics with good balance in a broad temperature range.

In particular, in order to achieve prevention of global warming, it is an urgent need to reduce the $CO_2$ emissions. Among eco-friendly vehicles mounted with an energy storage system composed of an energy storage device, such as a lithium secondary battery, a capacitor, etc., early dissemination of hybrid electric vehicle (HEV), plug-in hybrid electric vehicle (PHEV), and battery electric vehicle (BEV) is demanded. In vehicles, a moving distance is long, and therefore, there is a possibility that the vehicles are used in regions of a broad temperature range of from a very warm region of the tropics to a coldest region. In consequence, in particular, such an onboard energy storage device is required such that even when used in a broad temperature range of from high temperatures to low temperatures, the electrochemical characteristics are not worsened.

In the present specification, the term "lithium secondary battery" is used as a concept also including a so-called lithium ion secondary battery.

A lithium secondary battery is mainly constituted of a positive electrode and a negative electrode, each containing a material capable of absorbing and releasing lithium, and a nonaqueous electrolytic solution including a lithium salt and a nonaqueous solvent; and a carbonate, such as ethylene carbonate (EC), propylene carbonate (PC), etc., is used as the nonaqueous solvent.

In addition, metal lithium, a metal compound capable of absorbing and releasing lithium (e.g., a metal elemental substance, a metal oxide, an alloy with lithium, etc.), and a carbon material are known as the negative electrode. In particular, a lithium secondary battery using a carbon material capable of absorbing and releasing lithium, for example, coke, artificial graphite, natural graphite, etc., is widely put into practical use.

For example, as for a lithium secondary battery using, as a negative electrode material, a highly crystallized carbon material, such as natural graphite, artificial graphite, etc., it is known that decomposed products or a gas generated when a solvent in a nonaqueous electrolytic solution is reductively decomposed on a surface of the negative electrode at the time of charging hinders a desired electrochemical reaction of the battery, worsening of cycle properties is caused. In addition, when the decomposed products of the nonaqueous solvent are accumulated, it becomes difficult to smoothly achieve absorption and release of lithium on and from the negative electrode, and when used in a broad temperature range, electrochemical characteristics are apt to be worsened.

Furthermore, it is known that a lithium secondary battery using a metal lithium or an alloy thereof, a metal elemental substance, such as tin, silicon, etc., or an oxide thereof as the negative electrode material may have a high initial battery capacity, but the battery capacity and the battery performance thereof, such as cycle properties, may be largely worsened because the micronized powdering of the material may be promoted during cycles, which brings about accelerated reductive decomposition of the nonaqueous solvent, as compared with the negative electrode formed of a carbon material. In addition, the micronized powering of such a negative electrode material is promoted, or when the decomposed products of the nonaqueous solvent are accumulated, it becomes difficult to smoothly achieve absorption and release of lithium on and from the negative electrode, and when used in a broad temperature range, electrochemical characteristics are apt to be worsened.

Meanwhile, as for a lithium secondary battery using, as a positive electrode, for example, $LiCoO_2$, $LiMn_2O_4$, $LiNiO_2$, $LiFePO_4$, etc., it is known that decomposed products or a gas generated when a part of a nonaqueous solvent in a nonaqueous electrolytic solution is locally oxidatively decomposed on an interface between the positive electrode material and the nonaqueous electrolytic solution in a charged state hinders a desired electrochemical reaction of the battery, and thus, when used in a broad temperature range, the electrochemical characteristics are apt to be worsened, too.

In the light of the above, the movement of lithium ions is hindered, or the battery expands due to decomposed products or a gas generated when the nonaqueous electrolytic solution is decomposed on the positive electrode or negative electrode, so that the battery performance was worsened. Irrespective of the foregoing situation, the multifunctionality of electronic devices on which lithium secondary batteries are mounted is more and more advanced, and the electric power consumption tends to increase. The capacity of the lithium secondary battery is thus being much increased, and because of an increase of a density of the electrode, a reduction of a useless space capacity within the battery, and so on, a volume occupied by the nonaqueous electrolytic solution in the battery is becoming small. In consequence, it is the present situation that in the case of using the battery in a broad temperature range, the electrochemical characteristics are apt to be worsened due to decomposition of a bit of the nonaqueous electrolytic solution.

PTL 1 describes that a nonaqueous electrolytic solution containing, as an additive, a phosphate ester compound, such as triethyl phosphonoacetate, triethyl phosphonoformate, etc., is able to improve continuous charging properties and high-temperature storage properties and inhibit the gas generation.

PTL 2 describes that a nonaqueous electrolytic solution capable of realizing a lithium ion secondary battery having a higher positive electrode potential than that in a conventional one, being excellent in cycle properties, and generating little gas and a lithium ion secondary battery using the foregoing nonaqueous electrolytic solution can be provided.

CITATION LIST

Patent Literature

PTL 1: WO 2008/123038
PTL 2: JP-A 2015-18713

SUMMARY OF INVENTION

Technical Problem

A problem of the present invention is to provide a nonaqueous electrolytic solution capable of improving electrochemical characteristics in a broad temperature range, an energy storage device using the same, and a novel compound in which a polar group is bound to a phosphorus atom.

Solution to Problem

The present inventors made investigations in detail with respect to the performances of the aforementioned conventional nonaqueous electrolytic solutions. As a result, it was the actual situation that in the secondary batteries using the nonaqueous electrolytic solutions of PTLs 1 and 2, the effect could not be substantially exhibited with respect to the problem of improving the electrochemical characteristics in a broad temperature range, such as low-temperature discharging properties after high-temperature storage, etc.

Then, in order to solve the aforementioned problem, the present inventors made extensive and intensive investigations. As a result, it has been found that in a nonaqueous electrolytic solution having an electrolyte salt dissolved in a nonaqueous solvent, when it contains one or more compounds in which a specified polar group is bound directly to a phosphorus atom, the electrochemical characteristics of an energy storage device in a broad temperature range, particularly electrochemical characteristics of a lithium battery, can be improved, leading to accomplishment of the present invention. Such an effect is not suggested in PTLs 1 and 2 at all.

Specifically, the present invention provides the following (1) to (11).

(1) A nonaqueous electrolytic solution having an electrolyte salt dissolved in a nonaqueous solvent, the nonaqueous electrolytic solution containing a compound represented by the following general formula (X), in which a polar group (X) is bound to a phosphorus atom (P).

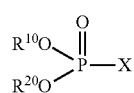
(X)

In the formula, $R^{10}$ and $R^{20}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and X is a polar group (i) containing a —C(=O) group, a —P(=O) group, or an —S(=O)$_2$ group, a polar group (ii) containing a —CN group or an alkyl group having 1 to 6 carbon atoms, in which a part of hydrogen atoms is substituted with a fluorine atom, or a 4- to 7-membered ring polar group (iii) containing a —C(=O)—O— group or a —C(=O)—N— group, provided that when X is a 4- to 7-membered ring polar group (iii) containing a —C(=O)—N— group, at least one of $R^{10}$ and $R^{20}$ is a lithium atom.

(2) The nonaqueous electrolytic solution as set forth in the above item (1), wherein the compound is a lithium phosphate represented by the following general formula (I), in which a polar group ($X^1$) is bound directly to a phosphorus atom (P) (first invention).

(I)

In the formula, $R^{20}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^1$ is a polar group (i) containing a —C(=O) group, a —P(=O) group, or an —S(=O)$_2$ group.

(3) The nonaqueous electrolytic solution as set forth in the above item (1), wherein the compound is a compound represented by the following general formula (II), in which a cyclic polar group ($X^2$) is bound directly to a phosphorus atom (P) (second invention).

(II)

In the formula, $R^{10}$ and $R^{20}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^2$ is a 4- to 7-membered ring polar group (iii) containing a —C(=O)—O— group or a —C(=O)—N— group, provided that when $X^2$ is a 4- to 7-membered ring polar group containing a —C(=O)—N— group, at least one of $R^{10}$ and $R^{20}$ is a lithium atom.

(4) The nonaqueous electrolytic solution as set forth in the above item (1), wherein the compound is a compound represented by the following general formula (III), in which a polar group ($X^3$) is bound to a phosphorus atom (P) (third invention).

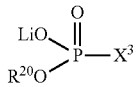
(III)

In the formula, $R^{20}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^3$ is a polar group containing a —C(=O) group, a —P(=O) group, an —S(=O)$_2$ group, a —CN group, or an alkyl group having 1 to 6 carbon atoms, in which a part of hydrogen atoms is substituted with a fluorine atom.

(5) An energy storage device including a positive electrode, a negative electrode, and a nonaqueous electrolytic solution having an electrolyte salt dissolved in a nonaqueous solvent, the nonaqueous electrolytic solution being the nonaqueous electrolytic solution as set forth in any of the above items (1) to (4).

(6) A lithium phosphate represented by any of general formulae (I-V) to (I-VII) as mentioned later, in which a polar group is bound directly to a phosphorus atom.

(7) An additive for an energy storage device, including the lithium phosphate as set forth in the above item (6).

(8) A lithium phosphonate represented by any of general formulae (IV-I) to (IV-VI) as mentioned later, in which a cyclic polar group is bound directly to a phosphorus atom.

(9) An additive for an energy storage device, including the lithium phosphonate as set forth in the above item (8).

(10) A compound represented by any of general formulae (III-1) to (III-7) as mentioned later, in which a polar group is bound to a phosphorus atom.

(11) An additive for an energy storage device, including the compound as set forth in the above item (10).

Advantageous Effects of Invention

In accordance with the present invention, it is possible to provide a nonaqueous electrolytic solution capable of improving electrochemical characteristics, particularly low-temperature discharging properties after high-temperature storage, of an energy storage device in a broad temperature range, an energy storage device using the same, such as a lithium battery, etc., and a novel compound in which a polar group is bound to a phosphorus atom.

DESCRIPTION OF EMBODIMENTS

[Nonaqueous Electrolytic Solution]

The nonaqueous electrolytic solution of the present invention is a nonaqueous electrolytic solution having an electrolyte salt dissolved in a nonaqueous solvent, the nonaqueous electrolytic solution containing a compound represented by the following general formula (X), in which a polar group (X) is bound to a phosphorus atom (P).

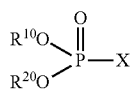

(X)

In the formula, $R^{10}$ and $R^{20}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and X is a polar group (i) containing a —C(=O) group, a —P(=O) group, or an —S(=O)$_2$ group, a polar group (ii) containing a —CN group or an alkyl group having 1 to 6 carbon atoms, in which a part of hydrogen atoms is substituted with a fluorine atom, or a 4- to 7-membered ring polar group (iii) containing a —C(=O)—O— group or a —C(=O)—N— group, provided that when X is a 4- to 7-membered ring polar group (iii) containing a —C(=O)—N— group, at least one of $R^{10}$ and $R^{20}$ is a lithium atom.

More specifically, nonaqueous electrolytic solutions of the first to third inventions are preferably exemplified as the nonaqueous electrolytic solution of the present invention.

The nonaqueous electrolytic solution of the first invention is a nonaqueous electrolytic solution having an electrolyte salt dissolved in a nonaqueous solvent, the nonaqueous electrolytic solution containing a compound represented by the foregoing general formula (I), in which a polar group ($X^1$) is bound directly to a phosphorus atom (P).

The nonaqueous electrolytic solution of the second invention is a nonaqueous electrolytic solution having an electrolyte salt dissolved in a nonaqueous solvent, the nonaqueous electrolytic solution containing a compound represented by the foregoing general formula (II), in which a heterocyclic polar group ($X^2$) is bound directly to a phosphorus atom (P).

The nonaqueous electrolytic solution of the third invention is a nonaqueous electrolytic solution having an electrolyte salt dissolved in a nonaqueous solvent, the nonaqueous electrolytic solution containing a compound represented by the foregoing general formula (III), in which a polar group ($X^3$) is bound to a phosphorus atom (P).

The reasons why the nonaqueous electrolytic solution of the present invention is able to drastically improve the electrochemical characteristics of the energy storage device in a broad temperature range are not always elucidated yet, the following may be considered.

In the lithium phosphate which is used in the first invention, as shown in the general formula (I), the polar group ($X^1$) containing a —C(=O) group, a —P(=O) group, or an —S(=O)$_2$ group is bound directly to the phosphorus atom (P). For that reason, the lithium phosphate is apt to be electrochemically decomposed, and a surface film that is minute and high in heat resistance is formed on a positive electrode and a negative electrode. In addition, the lithium phosphate represented by the general formula (I) is literally a lithium salt, and therefore, the aforementioned surface film is excellent in lithium ion conductivity. In consequence, it may be considered that the electrochemical characteristics are markedly improved in a broad temperature range as compared with those in triethyl phosphonoacetate or triethyl phosphonoformate as described in PTL 1.

In the compound which is used in the second invention, as shown in the general formula (II), the 4- to 7-membered heterocyclic ring-containing polar group ($X^2$) containing a —C(=O)—O— group or a —C(=O)—N— group is bound directly to the phosphorus atom (P). For that reason, the foregoing compound is apt to be electrochemically decomposed, and a surface film that is minute and high in heat resistance is formed on a positive electrode and a negative electrode. In addition, in the case where in the general formula (II), at least one of $R^{10}$ and $R^{20}$ is an Li atom, the foregoing compound is a lithium salt, and therefore, the aforementioned surface film is excellent in lithium ion conductivity. In consequence, it may be considered that the electrochemical characteristics are markedly improved in a broad temperature range as compared with those in triethyl phosphonoacetate or triethyl phosphonoformate as described in PTL 1.

In the compound which is used in the third invention, as shown in the general formula (III), the polar group ($X^3$) containing a —C(=O) group, a —P(=O) group, an —S(=O)$_2$ group, a —CN group, or an alkyl group having 1 to 6 carbon atoms, in which a part of hydrogen atoms is substituted with a fluorine atom, is bound to the phosphorus atom (P). For that reason, the foregoing compound is apt to be electrochemically decomposed, and a surface film that is minute and high in heat resistance is formed on a positive electrode and a negative electrode. In addition, the compound represented by the general formula (III) is a lithium salt, and therefore, the aforementioned surface film is excellent in lithium ion conductivity. In consequence, it may be considered that the electrochemical characteristics are markedly improved in a broad temperature range as compared with those in triethyl phosphonoacetate or triethyl phosphonoformate as described in PTL 1 or hexylphosphonic acid or 2-phosphonoacetic acid as described in PTL 2.

<Nonaqueous Electrolytic Solution of First Invention>

The lithium phosphate that is contained in the nonaqueous electrolytic solution of the first invention is represented by the following general formula (I).

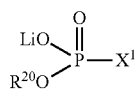

(I)

In the formula, $R^{20}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^1$ is a polar group (i) containing a —C(=O) group, a —P(=O) group, or an —S(=O)$_2$ group.

In the general formula (I), $R^{20}$ is preferably an organic group selected from the group consisting of an alkyl group having 1 to 6 carbon atoms, an alkenyl group having 3 to 4 carbon atoms, an alkynyl group having 3 to 6 carbon atoms, and an aryl group having 6 to 10 carbon atoms, in each of which a part of hydrogen atoms may be substituted with a halogen atom, or a lithium atom; and more preferably an organic group selected from an alkyl group having 1 to 4 carbon atoms and an alkynyl group having 3 to 4 carbon atoms, in each of which a part of hydrogen atoms may be substituted with a halogen atom.

As specific examples of the organic group represented by $R^{20}$, in which a part of hydrogen atoms may be substituted with a halogen atom, there are suitably exemplified a straight-chain alkyl group, such as a methyl group, an ethyl group, an n-propyl group, an n-butyl group, an n-pentyl group, an n-hexyl group, an n-heptyl group, an n-octyl group, etc.; a branched alkyl group, such as an isopropyl group, a sec-butyl group, a tert-butyl group, a tert-amyl group, etc.; a cycloalkyl group, such as a cyclopropyl group, a cyclobutyl group, a cyclopentyl group, a cyclohexyl group, etc.; an alkyl group, in which a part of hydrogen atoms is substituted with a halogen atom, such as a fluoromethyl group, a difluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a straight-chain alkenyl group, such as a vinyl group, a 1-propenyl group, a 2-propenyl group, a 2-butenyl group, a 3-butenyl group, a 4-pentenyl group, a 5-hexen-1-yl group, etc.; a branched alkenyl group, such as a 1-propen-2-yl group, a 1-buten-2-yl group, a 2-methyl-2-propen-1-yl group, etc.; an alkenyl group, in which a part of hydrogen atoms is substituted with a halogen atom, such as a 3,3-difluoro-2-propen-1-yl group, a 4,4-difluoro-3-buten-1-yl group, a 3,3-dichloro-2-propen-1-yl group, a 4,4-dichloro-3-buten-1-yl group, etc.; a straight-chain alkynyl group, such as a 2-propynyl group, a 2-butynyl group, a 3-butynyl group, a 4-heptynyl group, etc.; a branched alkynyl group, such as a 1-methyl-2-propynyl group, a 1,1-dimethyl-2-propynyl group, a 1-methyl-3-butynyl group, a 1-methyl-4-heptynyl group, etc.; an aryl group, such as a phenyl group, a 2-methylphenyl group, a 3-methylphenyl group, a 4-methylphenyl group, a 2,4-di-tert-butylphenyl group, a 4-tert-butylphenyl group, etc.; an aryl group, in which a part of hydrogen atoms is substituted with a halogen atom, such as a 2-fluorophenyl group, a 3-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,4-difluorophenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and the like.

Among those, a methyl group, an ethyl group, an n-propyl group, an n-butyl group, a 2,2-difluoroethyl group, a 2,2,2-trifluoroethyl group, a 2-propenyl group, a 2-propynyl group, and a phenyl group are preferred; and a methyl group, an ethyl group, a 2,2,2-trifluoroethyl group, a 2-propenyl group, and a 2-propynyl group are more preferred.

The lithium phosphate represented by the general formula (I) is preferably at least one lithium phosphate represented by any of the following general formulae (I-II) to (I-IV).

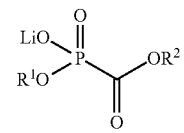

(I-II)

In the formula, $R^1$ and $R^2$ are each independently synonymous with $R^{20}$.

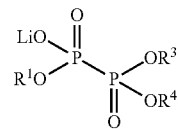

(I-III)

In the formula, $R^1$, $R^3$, and $R^4$ are each independently synonymous with $R^{20}$.

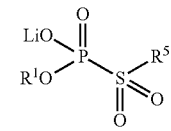

(I-IV)

In the formula, $R^1$ and $R^5$ are each independently synonymous with $R^{20}$.

Among the lithium phosphates represented by any of the general formulae (I-II) to (I-IV), the lithium phosphates represented by the general formula (I-II) or (I-III) are more preferred, and the lithium phosphates represented by the general formula (I-II) are still more preferred.

In the general formula (I-II), it is preferred that at least one of $R^1$ and $R^2$ is an organic group, in which a part of hydrogen atoms may be substituted with a halogen atom, and it is more preferred that both of $R^1$ and $R^2$ are an organic group, in which a part of hydrogen atoms may be substituted with a halogen atom.

Specific examples and suitable examples in the case where $R^1$ and $R^2$ are an organic group, in which a part of hydrogen atoms may be substituted with a halogen atom, are the same as the specific examples and suitable examples of $R^{20}$, and it is still more preferred that at least one of $R^1$ and $R^2$ is an alkynyl group having 3 to 4 carbon atoms.

In the general formula (I-III), it is preferred that at least one of $R^1$, $R^3$, and $R^4$ is an organic group, in which a part of hydrogen atoms may be substituted with a halogen atom; it is more preferred that at least two of $R^1$, $R^3$, and $R^4$ are an organic group, in which a part of hydrogen atoms may be substituted with a halogen atom; and it is still more preferred that all of $R^1$, $R^3$, and $R^4$ are an organic group, in which a part of hydrogen atoms may be substituted with a halogen atom.

Specific examples and suitable examples in the case where $R^1$, $R^3$, and $R^4$ are an organic group, in which a part of hydrogen atoms may be substituted with a halogen atom, are the same as the specific examples and suitable examples of $R^{20}$, and it is still more preferred that at least one of $R^1$, $R^3$, and $R^4$ is an alkynyl group having 3 to 4 carbon atoms.

In the general formula (I-IV), it is preferred that at least one of $R^1$ and $R^5$ is an organic group, in which a part of hydrogen atoms may be substituted with a halogen atom, and it is more preferred that both of $R^1$ and $R^5$ are an organic group, in which a part of hydrogen atoms may be substituted with a halogen atom.

Specific examples and suitable examples in the case where $R^1$ and $R^5$ are an organic group, in which a part of hydrogen atoms may be substituted with a halogen atom, are the same as the specific examples and suitable examples of $R^{20}$, and it is still more preferred that at least one of $R^1$ and $R^5$ is an alkynyl group having 3 to 4 carbon atoms.

As the lithium phosphates represented by any of the general formulae (I-II) and (I-IV), there are specifically exemplified the following compounds.

[Compounds Represented by General Formula (I-II)]

AA1

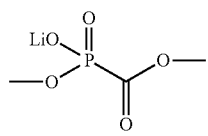

AA2

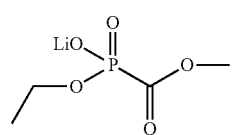

AA3

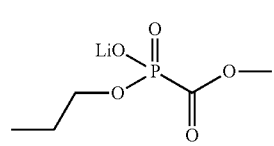

AA4

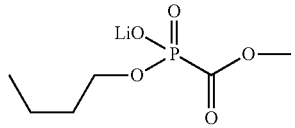

AA5

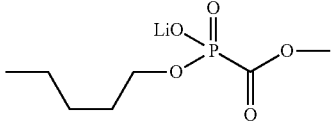

AA6

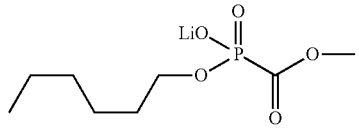

AA7

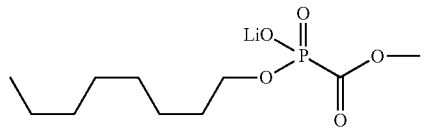

AA8

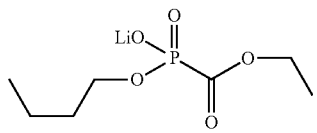

AA9

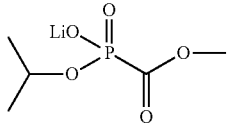

AA10

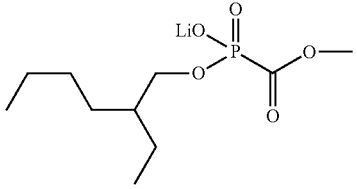

AA11

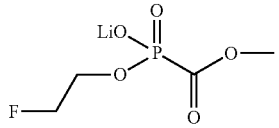

AA12

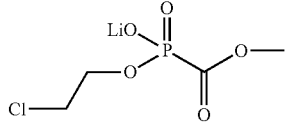

AA13

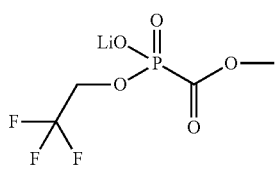

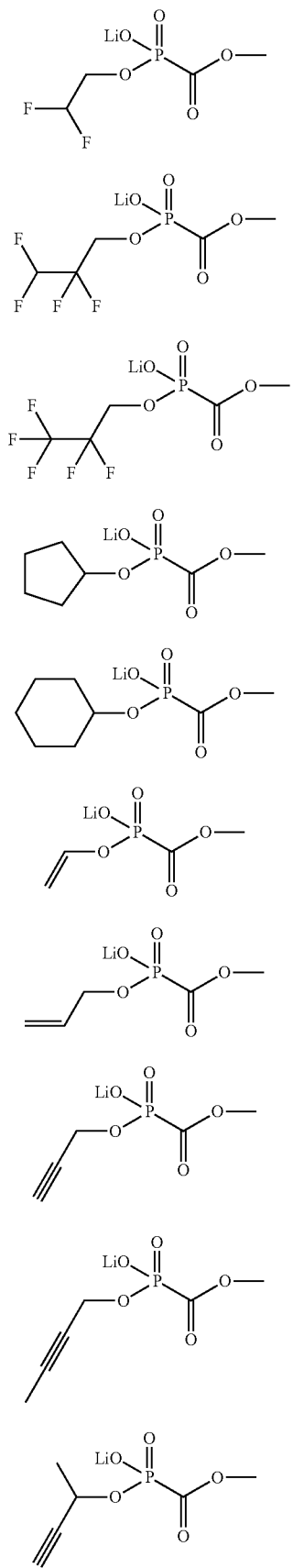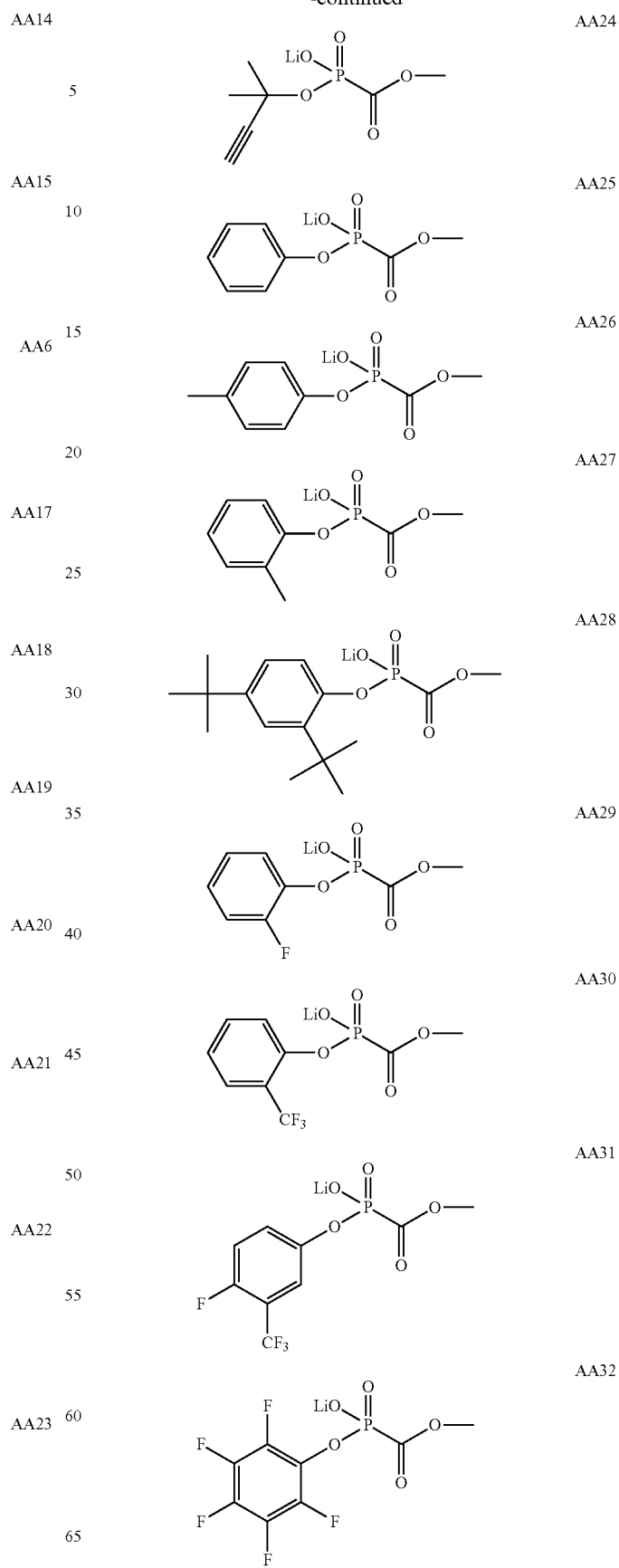

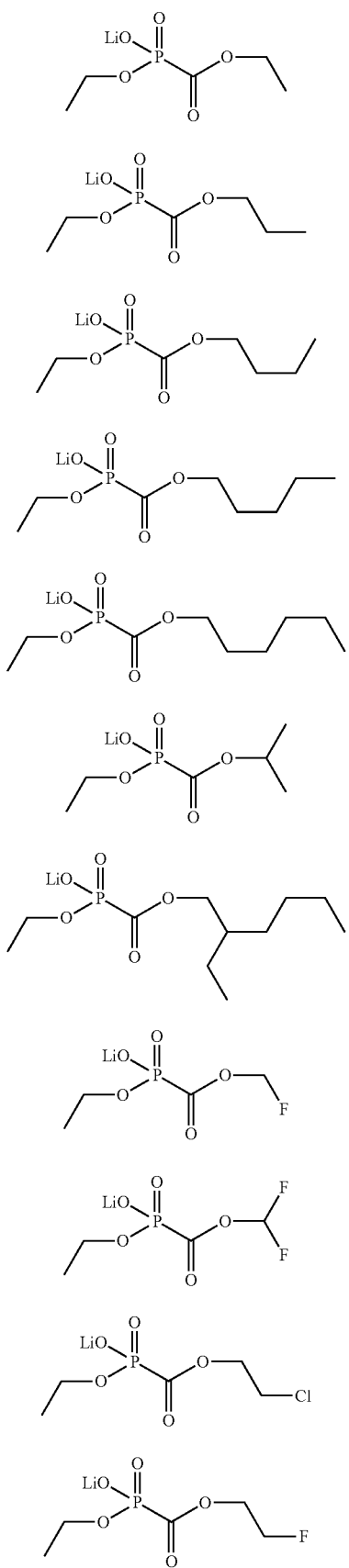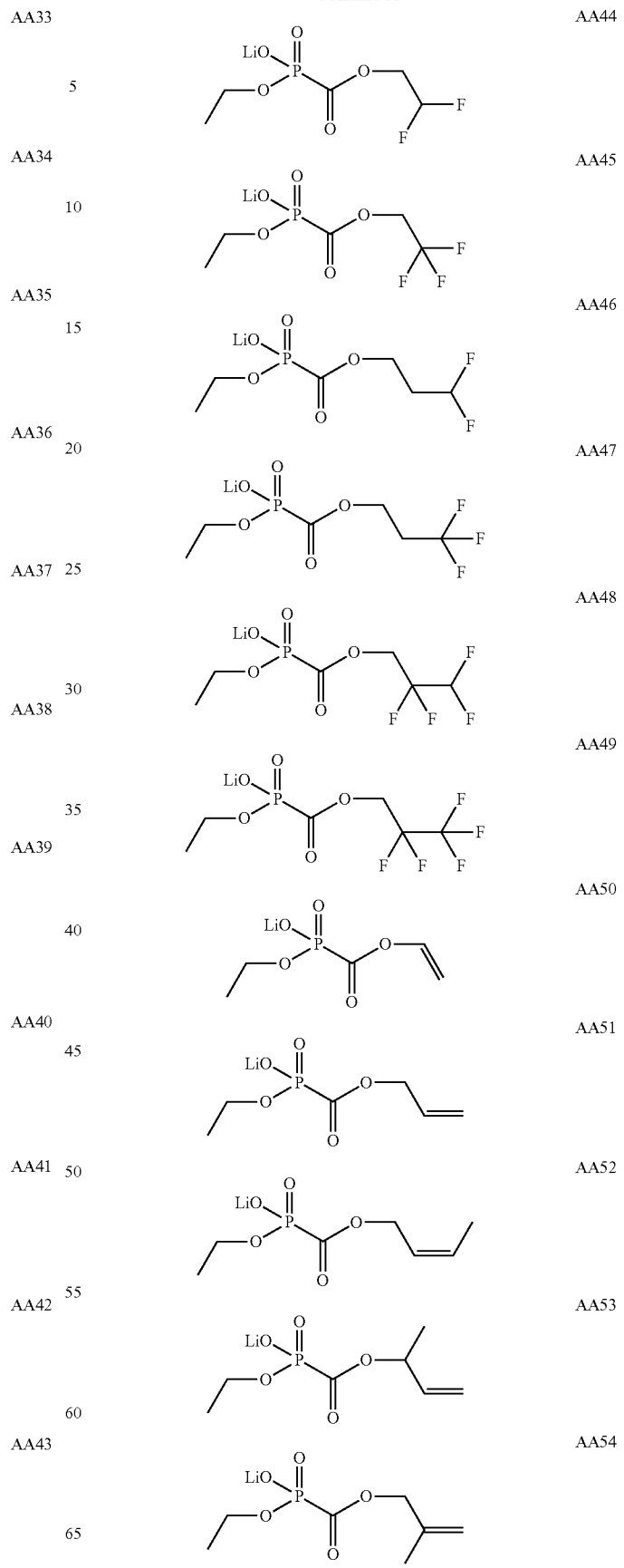

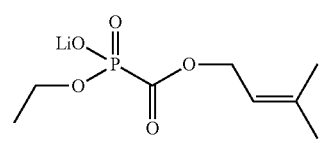 AA55
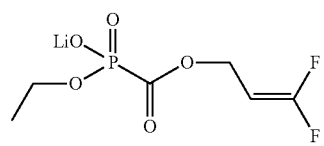 AA56
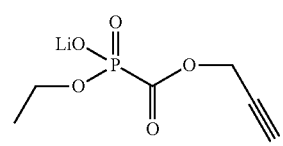 AA57
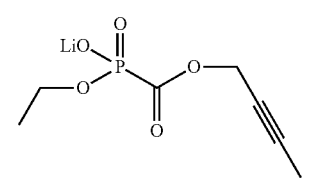 AA58
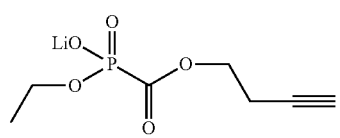 AA59
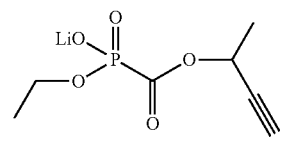 AA60
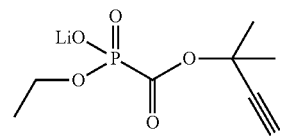 AA61
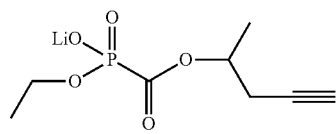 AA62
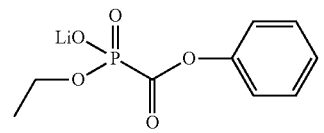 AA63
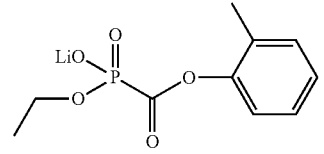 AA64
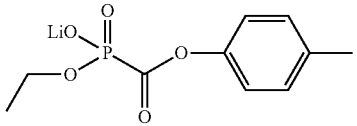 AA65
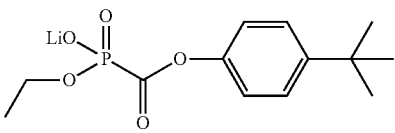 AA66
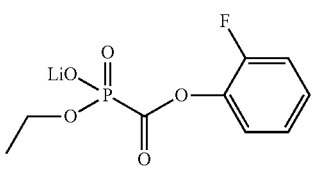 AA67
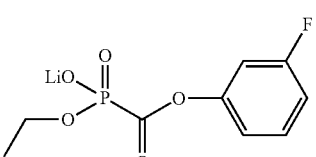 AA68
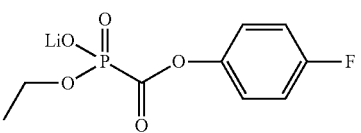 AA69
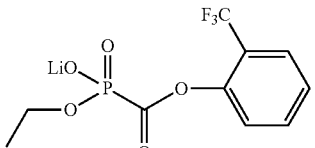 AA70
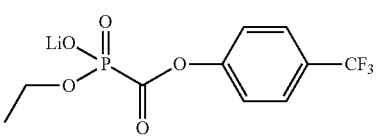 AA71
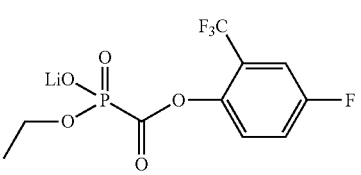 AA72
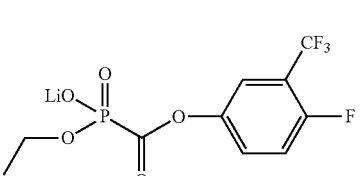 AA73
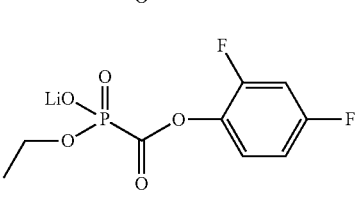 AA74

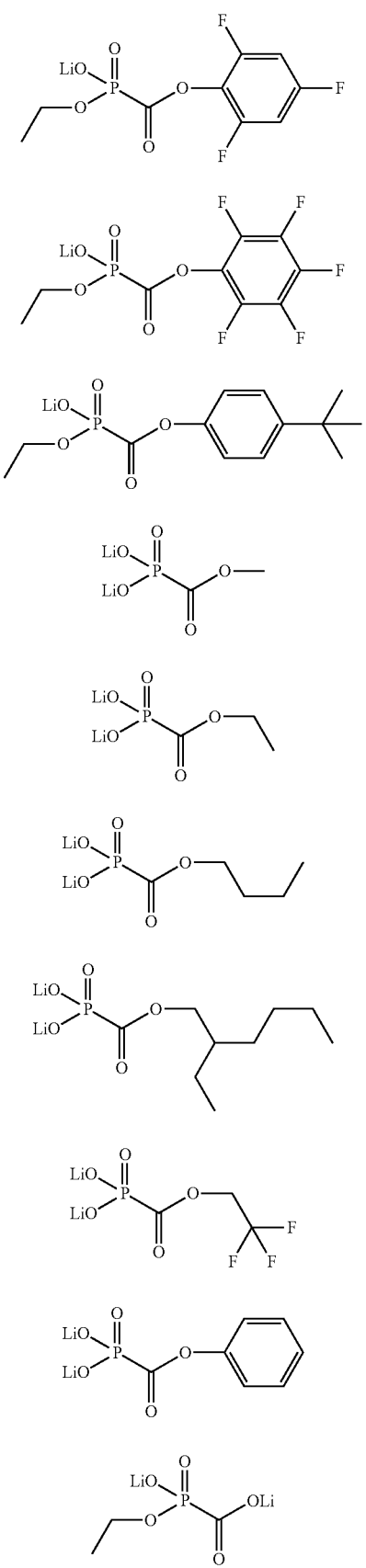
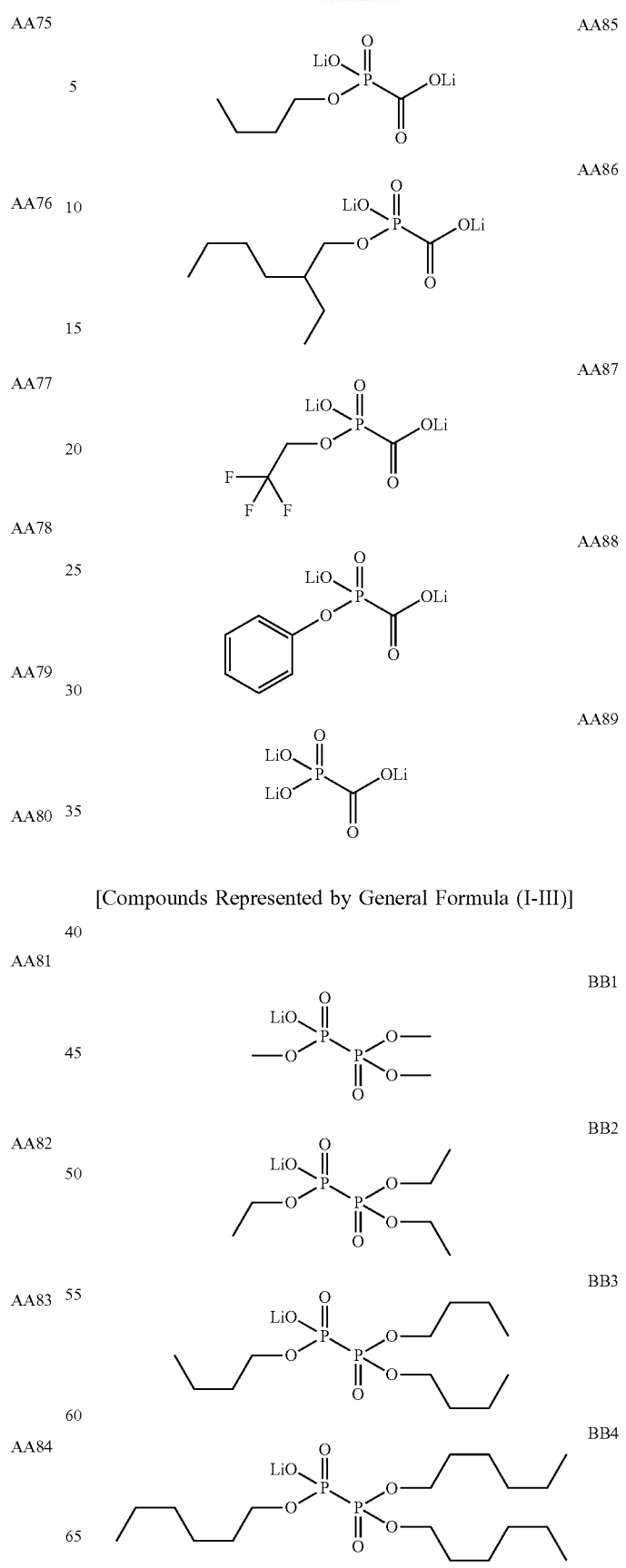
[Compounds Represented by General Formula (I-III)]

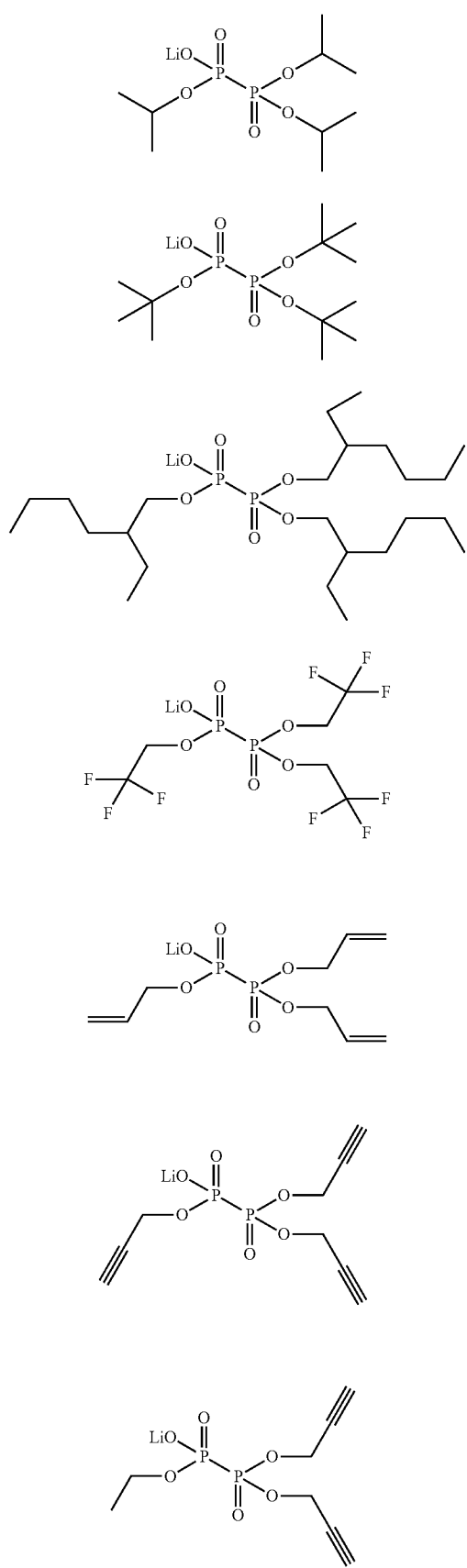

-continued

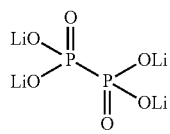
BB22

[Compounds Represented by General Formula (I-IV)]

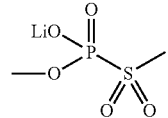
CC1

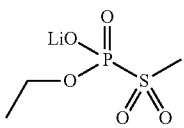
CC2

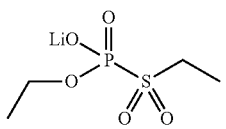
CC3

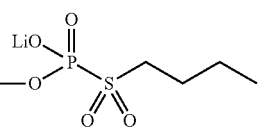
CC4

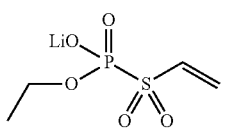
CC5

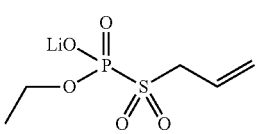
CC6

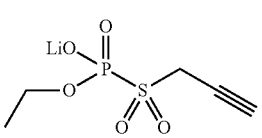
CC7

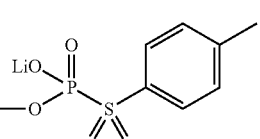
CC8

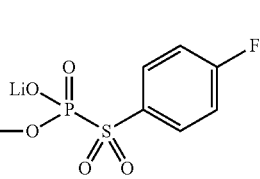
CC9

-continued

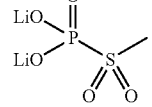
CC10

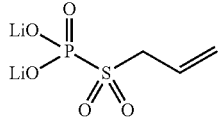
CC11

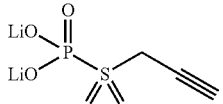
CC12

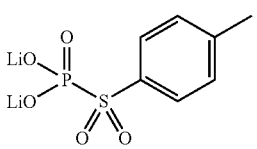
CC13

Among the aforementioned specific examples, one or more selected from Compounds AA1 to AA16, AA20 to AA35, AA40 to AA49, AA51, AA57 to AA61, AA63 to AA85, AA87 to AA89, BB1 to BB3, BB9 to BB13, BB17 to BB21, CC1 to CC3, and CC6 to CC9 are preferred; one or more selected from Compounds AA1 to AA4, AA8, AA20 to AA21, AA23 to AA29, AA33 to AA35, AA43 to AA45, AA51, AA57, AA60 to AA61, AA63 to AA67, AA77 to AA80, AA82, AA84 to AA85, AA89, BB1 to BB3, BB9 to BB11, BB17 to BB18, BB20 to BB21, CC1 to CC2, and CC7 are more preferred; and one or more selected from lithium methyl methoxycarbonylphosphonate (Compound AA1), lithium ethyl methoxycarbonylphosphonate (Compound AA2), lithium butyl methoxycarbonylphosphonate (Compound AA4), lithium butyl ethoxycarbonylphosphonate (Compound AA8), lithium 2-propenyl methoxycarbonylphosphonate (Compound AA20), lithium 2-propynyl methoxycarbonylphosphonate (Compound AA21), lithium 3-butyn-2-yl methoxycarbonylphosphonate (Compound AA23), lithium 2-methyl-3-butyn-2-yl methoxycarbonylphosphonate (Compound AA24), lithium phenyl methoxycarbonylphosphonate (Compound AA25), lithium 2,4-di-tert-butylphenyl methoxycarbonylphosphonate (Compound AA28), lithium ethyl ethoxycarbonylphosphonate (Compound AA33), lithium ethyl butoxycarbonylphosphonate (Compound AA35), lithium ethyl 2,2-difluoroethoxycarbonylphosphonate (Compound AA44), lithium ethyl 2,2,2-trifluoroethoxycarbonylphosphonate (Compound AA45), lithium ethyl 2-propenyloxycarbonylphosphonate (Compound AA51), lithium ethyl 2-propynyloxycarbonylphosphonate (Compound AA57), lithium ethyl 3-butyn-2-yloxycarbonylphosphonate (Compound AA60), lithium ethyl 2-methyl-3-butyn-2-yloxycarbonylphosphonate (Compound AA61), lithium ethyl phenyloxycarbonylphosphonate (Compound AA63), lithium ethyl 4-tert-butylphenyloxycarbonylphosphonate (Compound AA66), lithium phenyl 4-tert-butylphenyloxycarbonylphosphonate (Compound AA77), dilithium methoxycarbonylphosphonate (Compound AA78), dilithium ethoxycarbonylphosphonate (Compound AA79), ethyl dilithium oxycarbonylphoshonate (Compound AA84), trilithium oxycarbonylphosphonate (Compound AA89), lithium trimethylhypodiphosphate (Compound BB1), lithium triethylhypodiphosphate (Compound BB2), lithium tributylhypodiphosphate (Compound BB3), lithium tris(2-propenyl)hypodiphosphate (Compound BB9), lithium tris(2-propynyl)hypodiphosphate (Compound BB10), lithium methyl methylsulfonylphosphonate (Compound CC1), lithium ethyl methylsulfonylphosphonate (Compound CC2), and lithium ethyl 2-propyne-1-ylsulfonylphosphonate (Compound CC7) are especially preferred.

In the nonaqueous electrolytic solution of the first invention, a content of the lithium phosphate represented by the general formula (I), which is contained in the nonaqueous electrolytic solution, is preferably 0.001 to 10 mass % in the nonaqueous electrolytic solution. When the content is 10 mass % or less, there is less concern of occurrence of the matter that a surface film is excessively formed on an electrode, so that the low-temperature properties are worsened, whereas when it is 0.001 mass % or more, the formation of a surface film is sufficient, and an improving effect of the electrochemical characteristics in a broad temperature range is enhanced, and hence, such is preferred. The content is more preferably 0.05 mass % or more, and still more preferably 0.1 mass % or more in the nonaqueous electrolytic solution. An upper limit thereof is more preferably 5 mass % or less, and still more preferably 3 mass % or less.

In the nonaqueous electrolytic solution of the first invention, by combining the lithium phosphate represented by the general formula (I) with a nonaqueous solvent, an electrolyte salt, and further other additives as mentioned later, a peculiar effect of synergistically improving the electrochemical characteristics in a broad temperature range is revealed.

<Nonaqueous Electrolytic Solution of Second Invention>

The compound that is contained in the nonaqueous electrolytic solution of the second invention, in which a cyclic polar group ($X^2$) is bound directly to a phosphorus atom (P), is represented by the following general formula (II).

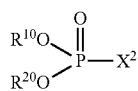

(II)

In the formula, $R^{10}$ and $R^{20}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^2$ is a 4- to 7-membered ring polar group containing a —C(=O)—O— group or a —C(=O)—N— group, provided that when $X^2$ is a 4- to 7-membered ring polar group containing a —C(=O)—N— group, at least one of $R^{10}$ and $R^{20}$ is a lithium atom.

In the general formula (II), $R^{10}$ and $R^{20}$ are each preferably an organic group selected from the group consisting of an alkyl group having 1 to 6 carbon atoms, an alkenyl group having 3 to 4 carbon atoms, an alkynyl group having 3 to 6 carbon atoms, and an aryl group having 6 to 12 carbon atoms, in each of which a part of hydrogen atoms may be substituted with a halogen atom, or a lithium atom; and more preferably an organic group selected from the group consisting of an alkyl group having 1 to 4 carbon atoms and an aryl group having 6 to 12 carbon atoms, in each of which a part of hydrogen atoms may be substituted with a halogen atom, or a lithium atom.

Specific examples and suitable examples of $R^{10}$ and $R^{20}$ are the same as the specific examples and suitable examples of $R^{20}$ of the general formula (I) in the first invention.

In the general formula (II), it is preferred that at least of $R^{10}$ and $R^{20}$ is a lithium atom.

In the general formula (II), $X^2$ is preferably a heterocyclic polar group selected from a 5- to 7-membered ring cyclic carbonate ester group, a 4- to 7-membered ring cyclic carboxylic acid ester group, a 5- to 7-membered ring cyclic acid anhydride group, a 5- to 7-membered ring cyclic imide group, a maleimide group, and a 5- to 7-membered ring cyclic amide group; more preferably a heterocyclic polar cyclic group selected from a 5- to 6-membered ring cyclic carbonate ester group, a 5- to 6-membered ring cyclic carboxylic acid ester group, a 5- to 6-membered ring cyclic acid anhydride group, a 5- to 6-membered ring cyclic imide group, a maleimide group, and a 5- to 6-membered ring cyclic amide group; and especially preferably a heterocyclic polar group selected from a 5- to 6-membered ring cyclic carbonate ester group, a 5- to 6-membered ring cyclic carboxylic acid ester group, and a 5- to 6-membered ring cyclic imide group.

The compound represented by the general formula (II) is preferably at least one compound represented by any of the following general formulae (II-I) to (II-VI).

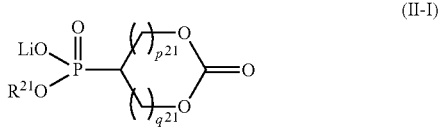

(II-I)

In the formula, $R^{21}$ is synonymous with $R^{20}$; and $p^{21}$ and $q^{21}$ each independently represent an integer of 0 to 2 and satisfy a relation: $1 \leq (p^{21}+q^{21}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (II-VII).

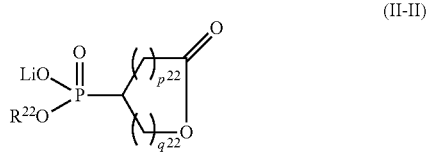

(II-II)

In the formula, $R^{22}$ is synonymous with $R^{20}$; and $p^{22}$ and $q^{22}$ each independently represent an integer of 0 to 3 and satisfy a relation: $1 \leq (p^{22}+q^{22}) \leq 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (II-VII).

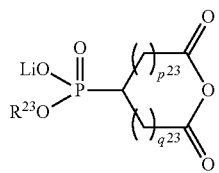

(II-III)

In the formula, $R^{23}$ is synonymous with $R^{20}$; and $p^{23}$ and $q^{23}$ each independently represent an integer of 0 to 2 and satisfy a relation: $1 \leq (p^{23}+q^{23}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (II-VII).

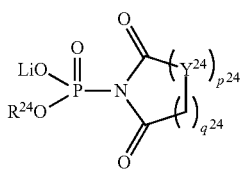

(II-IV)

In the formula, $R^{24}$ is synonymous with $R^{20}$; $Y^{24}$ represents an —NH— group or an —O— group; $p^{24}$ represents an integer of 0 to 1; $q^{24}$ represents an integer of 1 to 4; and $p^{24}$ and $q^{24}$ satisfy a relation: $2 \leq (p^{24}+q^{24}) \leq 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (II-VII).

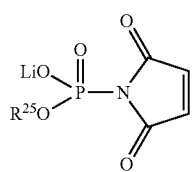

(II-V)

In the formula, $R^{25}$ is synonymous with $R^{20}$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (II-VII).

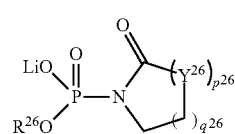

(II-VI)

In the formula, $R^{26}$ is synonymous with $R^{20}$; $Y^{26}$ represents an —NH— group or an —O— group; $p^{26}$ represents an integer of 0 to 1; $q^{26}$ represents an integer of 1 to 4; and $p^{26}$ and $q^{26}$ satisfy a relation: $2 \leq (p^{26}+q^{26}) \leq 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (II-VII).

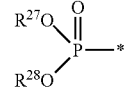

(II-VII)

In the formula, $R^{27}$ and $R^{28}$ are each independently synonymous with $R^{20}$; and * represents a site binding to the cyclic polar group.

Among the compounds represented by the general formulae (II-I) to (II-VI), the compounds represented by the general formula (II-I), (II-II), or (II-IV) are more preferred, and the compounds represented by the general formula (II-I) or (II-IV) are still more preferred.

In the general formula (II-I), specific examples and suitable examples of $R^{21}$ are the same as the specific examples and suitable examples of $R^{20}$. $R^{21}$ is preferably a methyl group, an ethyl group, an n-propyl group, an n-butyl group, a 2,2-difluoroethyl group, a 2,2,2-trifluoroethyl group, a 2-propenyl group, a 2-propynyl group, a phenyl group, or a lithium atom, and more preferably a methyl group, an ethyl group, a 2,2,2-trifluoroethyl group, a phenyl group, or a lithium atom.

In the general formula (II-II), specific examples and suitable examples of $R^{22}$ are the same as the specific examples and suitable examples of $R^{20}$, and more specific examples thereof are the same as the aforementioned suitable examples of $R^{21}$.

In the general formula (II-III), specific examples and suitable examples of $R^{23}$ are the same as the specific examples and suitable examples of $R^{20}$, and more specific examples thereof are the same as the aforementioned suitable examples of $R^{21}$.

In the general formula (II-IV), specific examples and suitable examples of $R^{24}$ are the same as the specific examples and suitable examples of $R^{20}$, and more specific examples thereof are the same as the aforementioned suitable examples of $R^{21}$.

In the general formula (II-V), specific examples and suitable examples of $R^{25}$ are the same as the specific examples and suitable examples of $R^{20}$, and more specific examples thereof are the same as the aforementioned suitable examples of $R^{21}$.

In the general formula (II-VI), specific examples and suitable examples of $R^{26}$ are the same as the specific examples and suitable examples of $R^{20}$, and more specific examples thereof are the same as the aforementioned suitable examples of $R^{21}$.

As the compounds represented by the general formulae (II-I) to (II-VI), in which the specified cyclic polar group is bound directly to the phosphorus atom (P), specifically, there are suitably exemplified the following compounds.

[Compounds Represented by General Formula (II-I)]

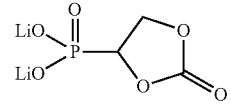

a1

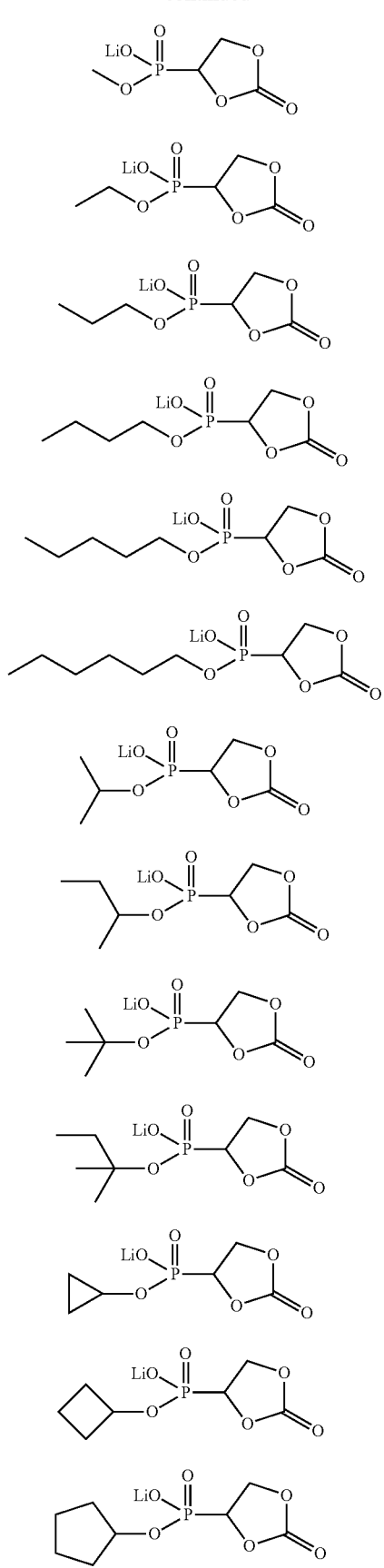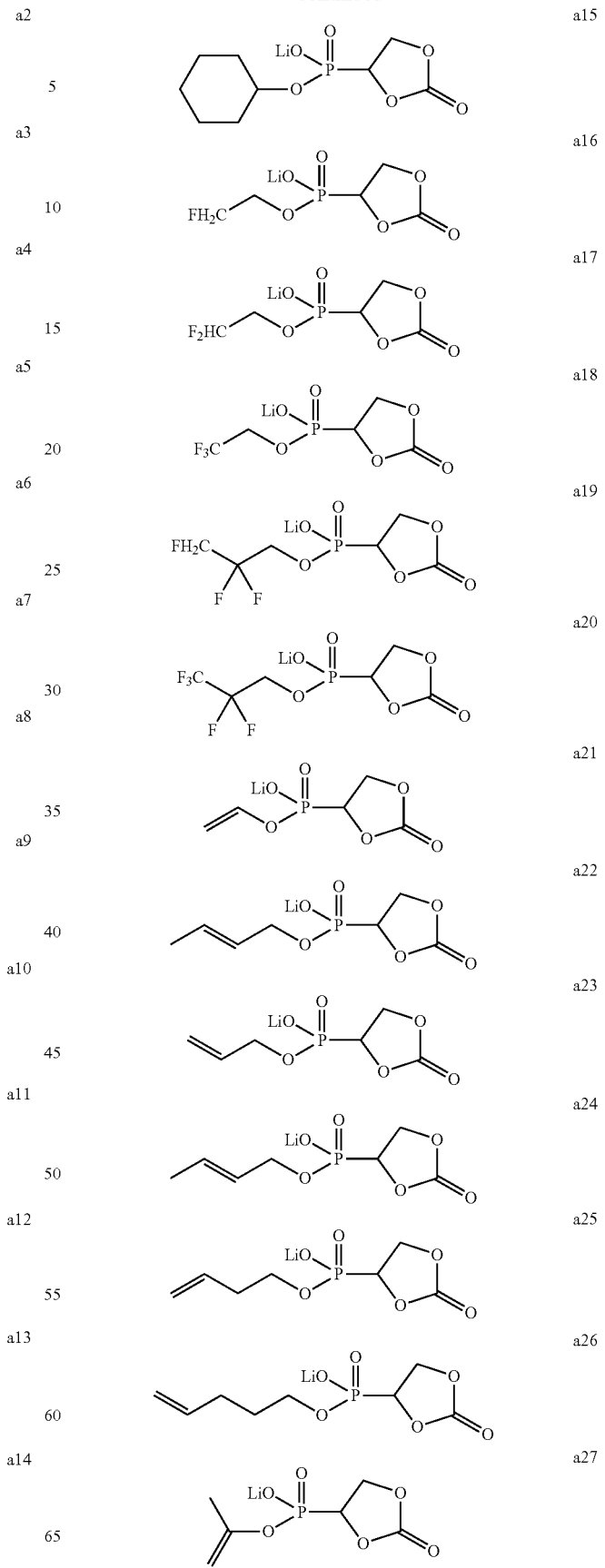

-continued
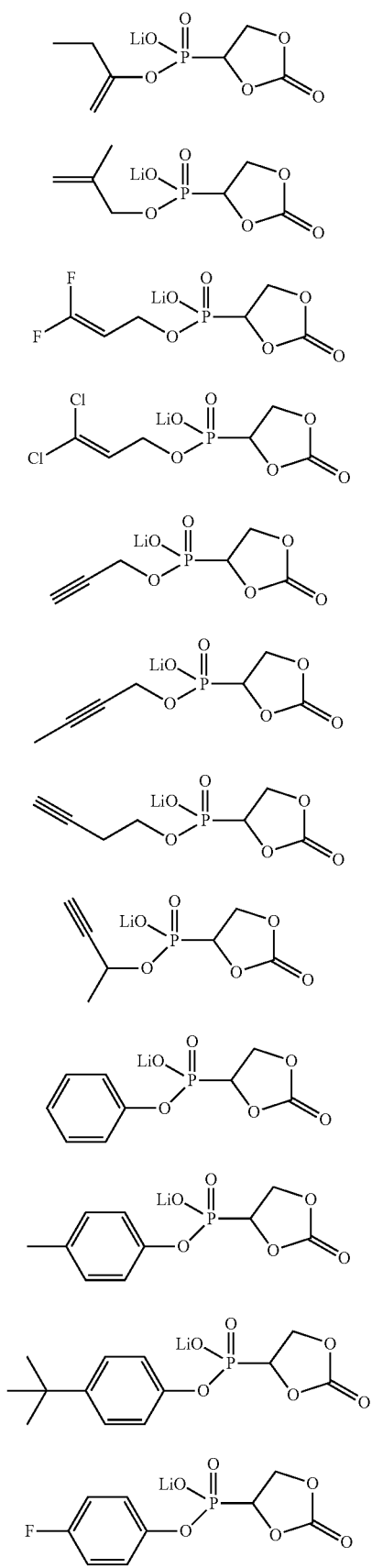
a28
a29
a30
a31
a32
a33
a34
a35
a36
a37
a38
a39
-continued
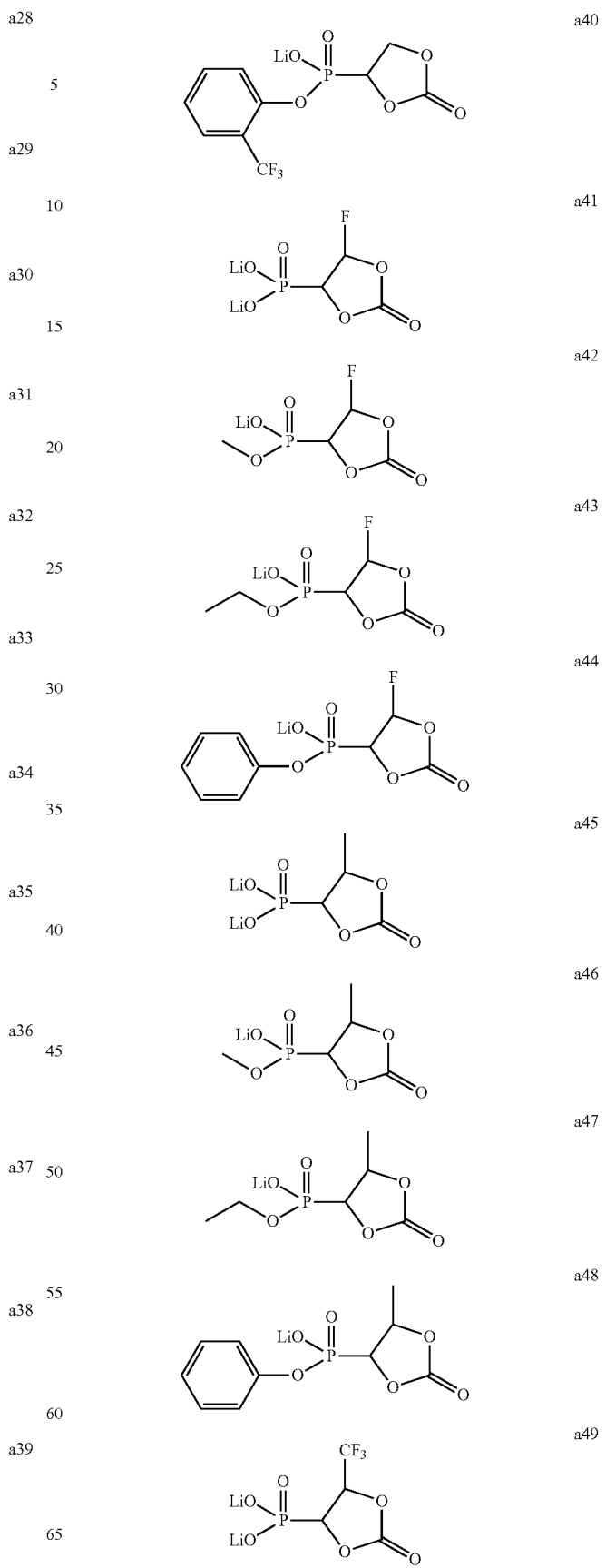
a40
a41
a42
a43
a44
a45
a46
a47
a48
a49

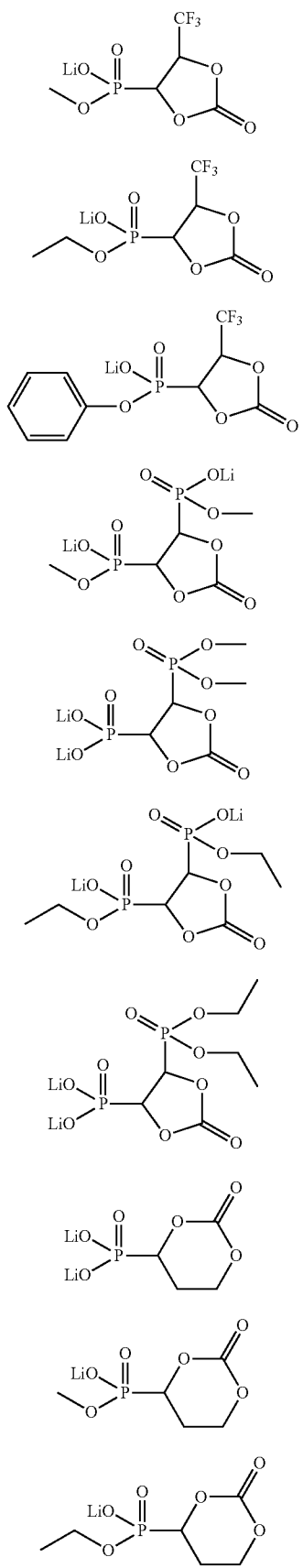
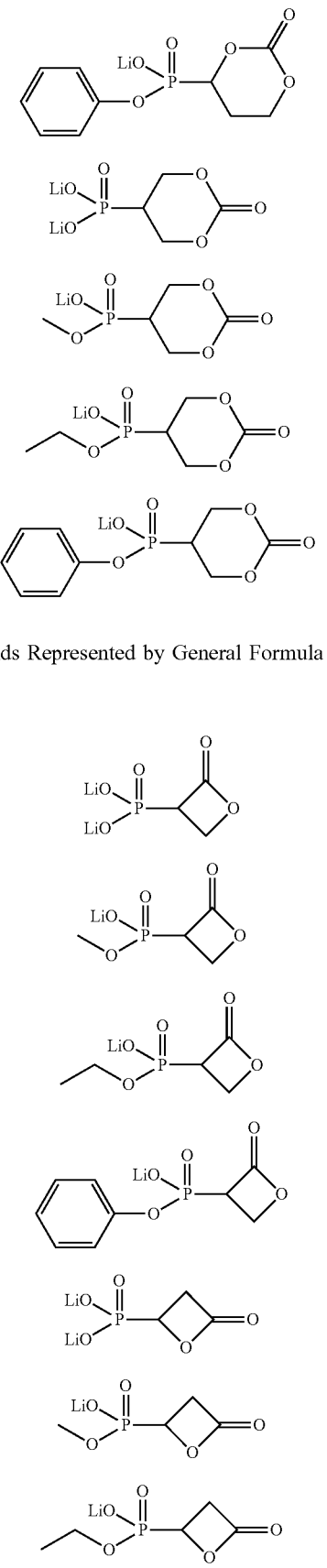
[Compounds Represented by General Formula (II-II)]

-continued
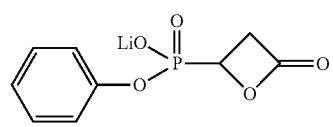 b8
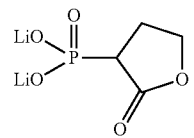 b9
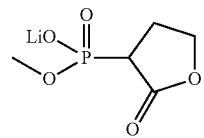 b10
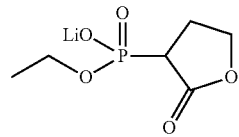 b11
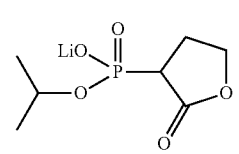 b12
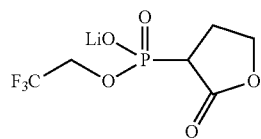 b13
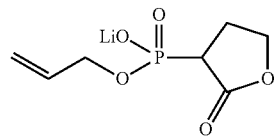 b14
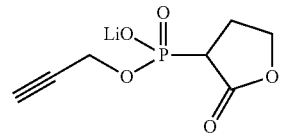 b15
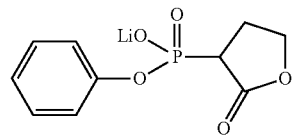 b16
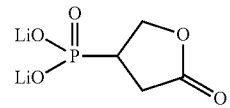 b17
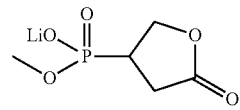 b18
-continued
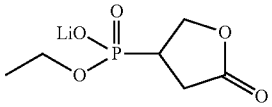 b19
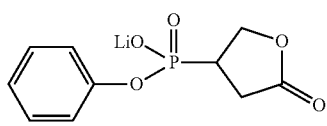 b20
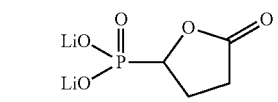 b21
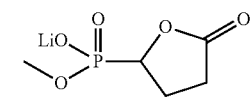 b22
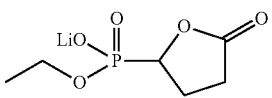 b23
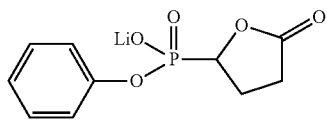 b24
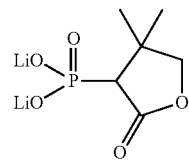 b25
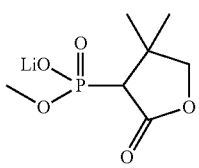 b26
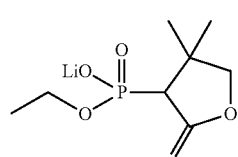 b27
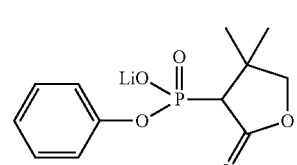 b28
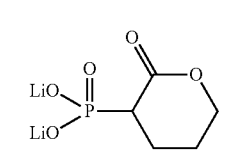 b29

[Compounds Represented by General Formula (II-III)]
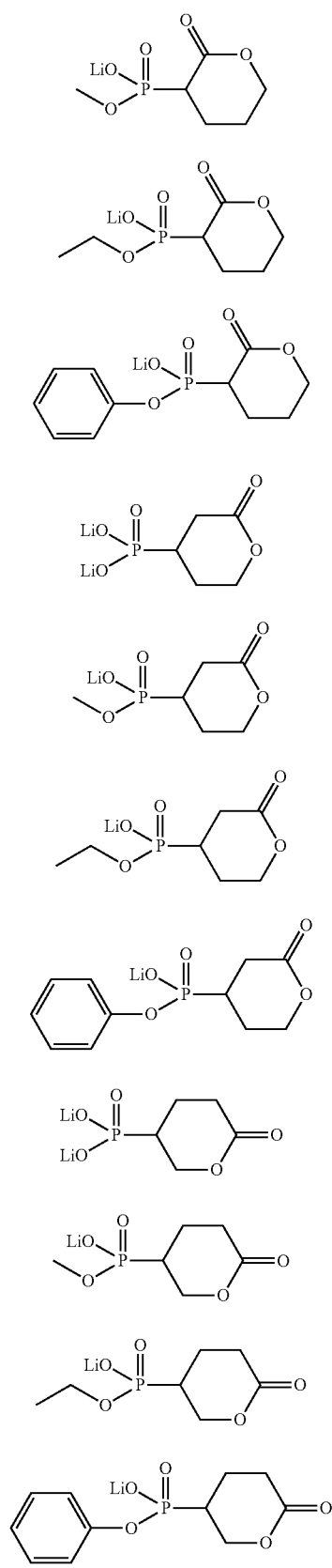

-continued
c11 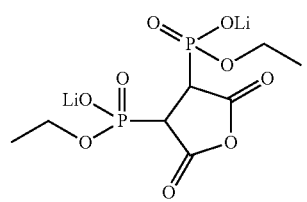
c12 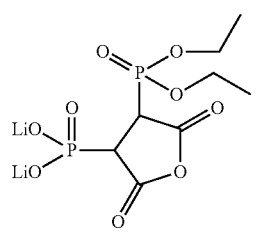
c13 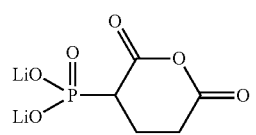
c14 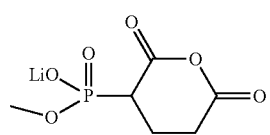
c15 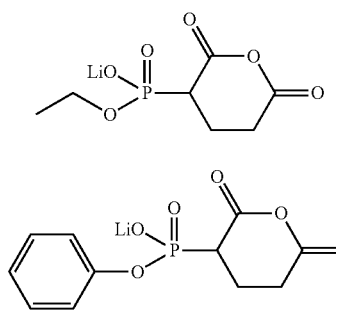
c16 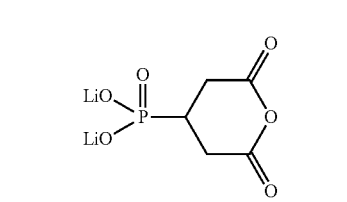
c17 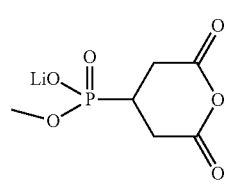
c18 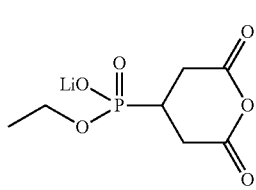
c19 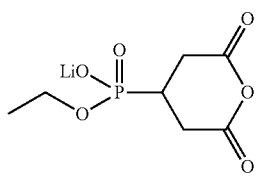
-continued
c20 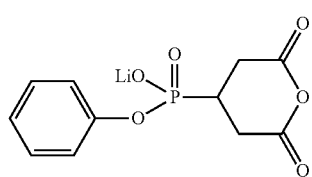
[Compounds Represented by General Formula (II-IV)]
g1 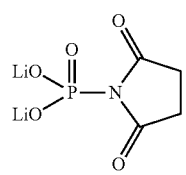
g2 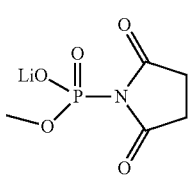
g3 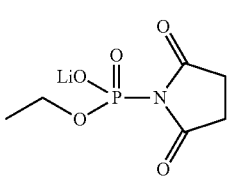
g4 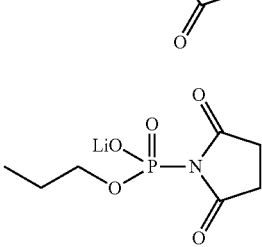
g5 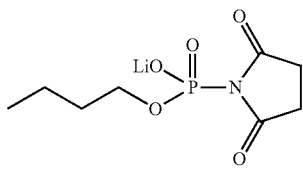
g6 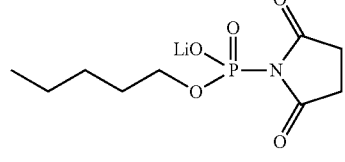
g7 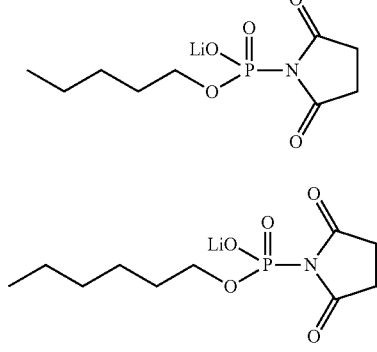

g8 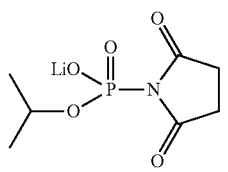
g9 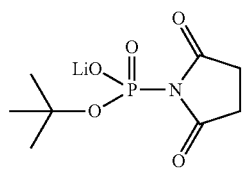
g10 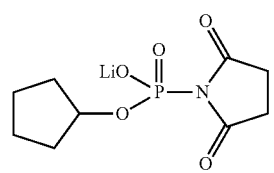
g11 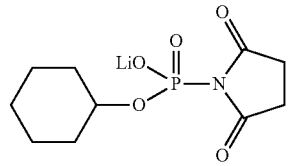
g12 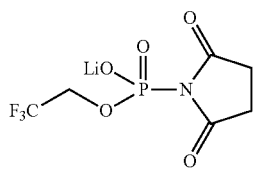
g13 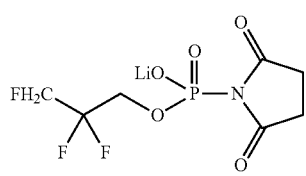
g14 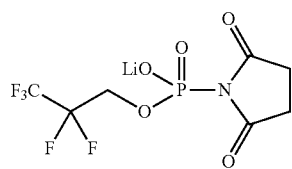
g15 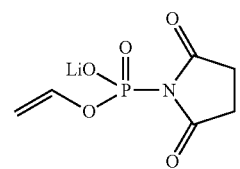
g16 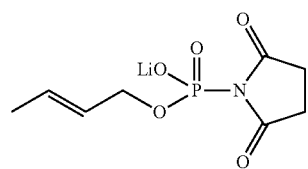
g17 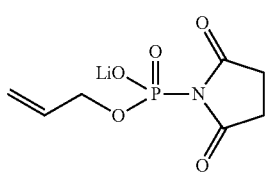
g18 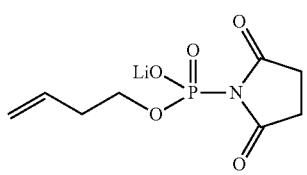
g19 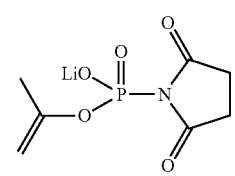
g20 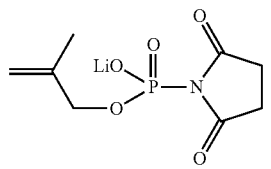
g21 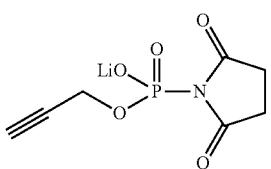
g22 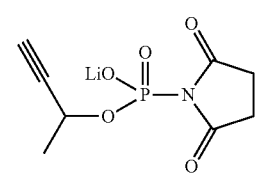
g23 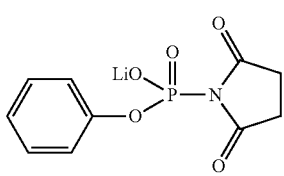
g24 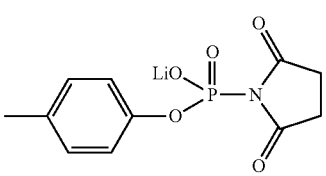
g25 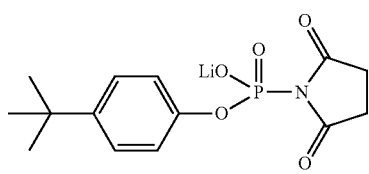

-continued
g26
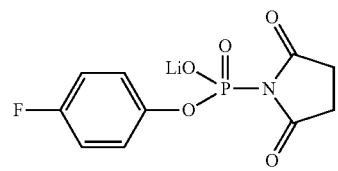
g27
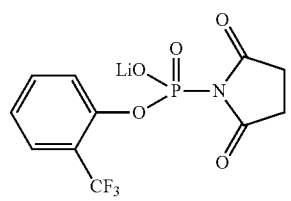
g28
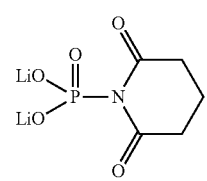
g29
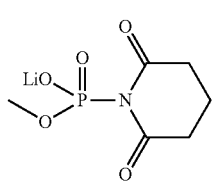
g30
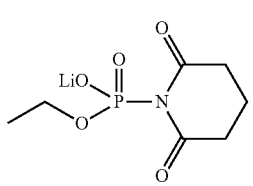
g31
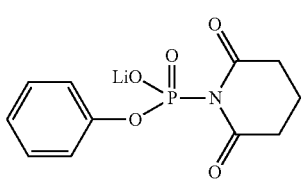
g32
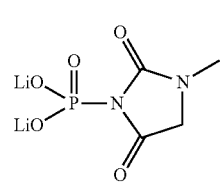
g33
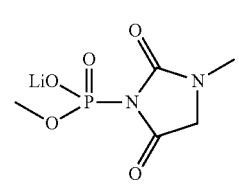
g34
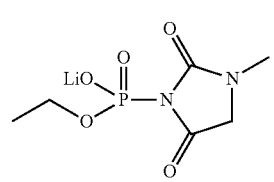
-continued
g35
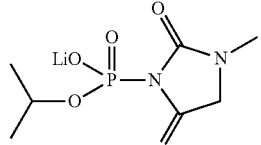
g36
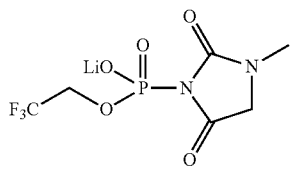
g37
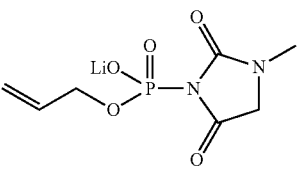
g38
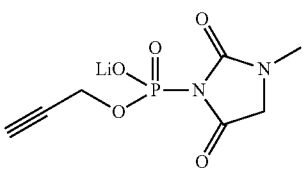
g39
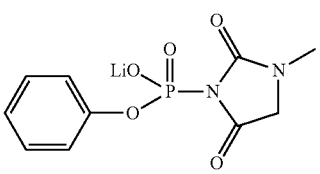
g40
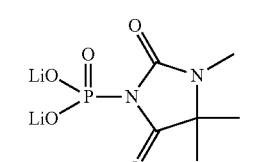
g41
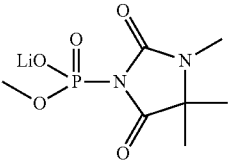
g42
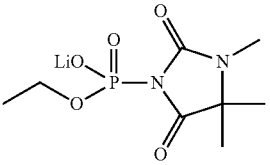
g43
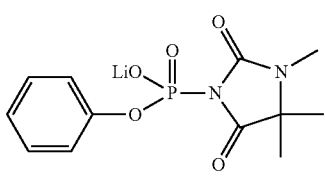

[Compounds Represented by General Formula (II-V)]
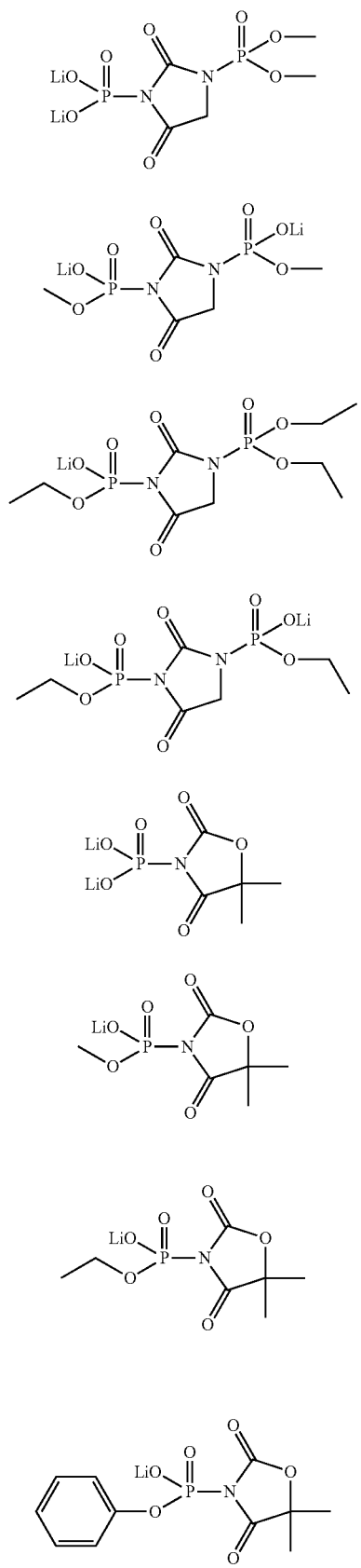

[Compounds Represented by General Formula (II-VI)]
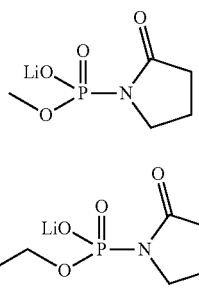 i1
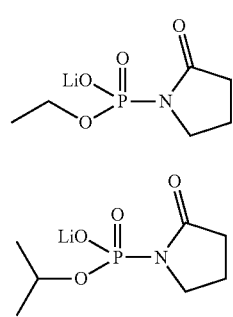 i2
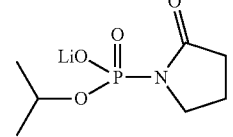 i3
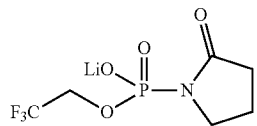 i4
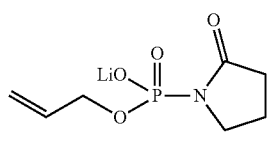 i5
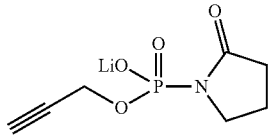 i6
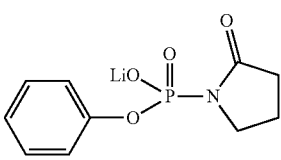 i7
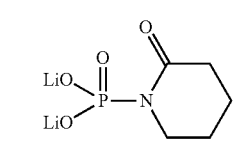 i8
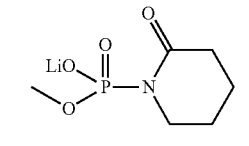 i9
i10
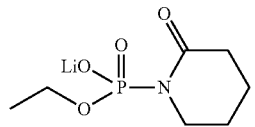 i11
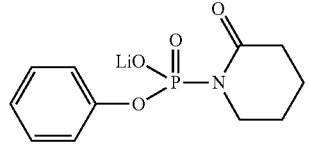 i12
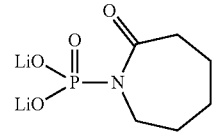 i13
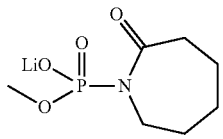 i14
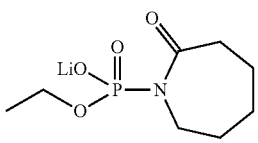 i15
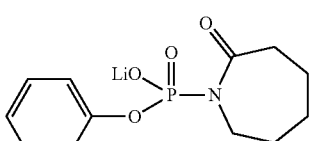 i16
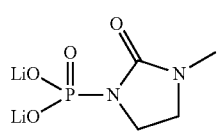 i17
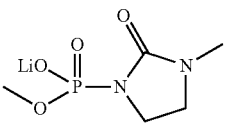 i18
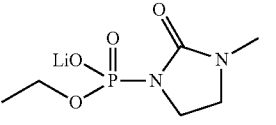 i19
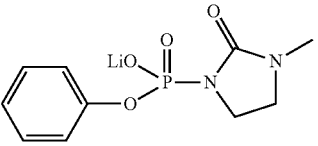 i20
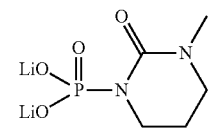 i21

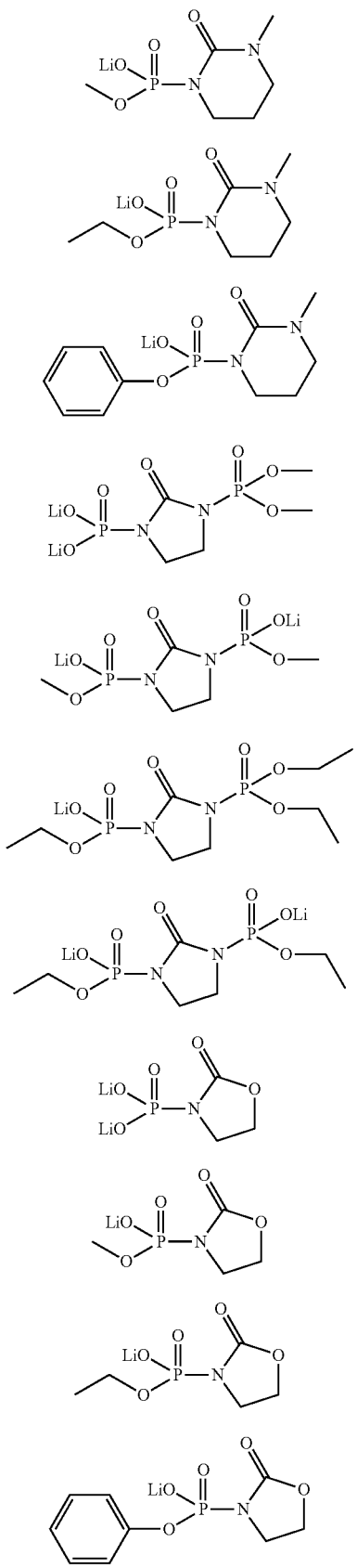

Among the aforementioned suitable examples, one or more selected from Compounds a1 to a6, a8 to a11, a14 to a18, a21 to a24, a30 to a33, a35 to a64, b9 to b40, c1 to C20, g1 to g6, g8 to g12, g15 to g17, g21 to g51, h1 to h8, i1 to i12, and i17 to i32 are preferred; one or more selected from Compounds a1 to a5, a17, a18, a23, a36, a41 to a64, b9 to b11, b13 to b24, c1 to c3, c5 to c20, g1 to g5, g12, g17, g23, g28 to g31, g32 to g34, g36, g37, g39, g40 to g43, g44 to g51, h1 to h3, h5, h6, h8, i1 to i3, i5, i6, i8, i9 to i12, and i17 to i32 are more preferred; and one or more selected from lithium (2-oxo-1,3-dioxolan-4-yl)phosphonate (Compound a1), lithium methyl (2-oxo-1,3-dioxolan-4-yl)phosphonate (Compound a2), lithium ethyl (2-oxo-1,3-dioxolan-4-yl) phosphonate (Compound a3), lithium 2,2,2-trifluoroethyl (2-oxo-1,3-dioxolan-4-yl)phosphonate (Compound a18), lithium phenyl (2-oxo-1,3-dioxolan-4-yl)phosphonate (Compound a36), lithium (2-oxotetrahydrofuran-3-yl)phosphonate (Compound b9), lithium methyl (2-oxotetrahydrofuran-3-yl)phosphonate (Compound b10), lithium ethyl (2-oxotetrahydrofuran-3-yl)phosphonate (Compound b11), lithium 2,2,2-trifluoroethyl (2-oxotetrahydrofuran-3-yl) phosphonate (Compound b13), lithium phenyl (2-oxotetrahydrofuran-3-yl)phosphonate (Compound b16), lithium (2,5-dioxotetrahydrofuran-3-yl)phosphonate (Compound c1), lithium methyl (2,5-dioxotetrahydrofuran-3-yl)phosphonate (Compound c2), lithium ethyl (2,5-dioxotetrahydrofuran-3-yl)phosphonate (Compound c3), lithium 2,2,2-trifluoroethyl (2,5-dioxotetrahydrofuran-3-yl)phosphonate (Compound c5), lithium phenyl (2,5-dioxotetrahydrofuran-3-yl)phosphonate (Compound c8), lithium (2,5-dioxopyrolidin-1-yl)phosphonate (Compound g1), lithium methyl (2,5-dioxopyrolidin-1-yl)phosphonate (Compound g2), lithium ethyl (2,5-dioxopyrolidin-1-yl)phosphonate (Compound g3), lithium 2,2,2-trifluoroethyl (2,5-dioxopyrolidin-1-yl)phosphonate (Compound g12), lithium phenyl (2,5-dioxopyrolidin-1-yl)phosphonate (Compound g23), lithium ethyl (3-methyl-2,5-dioxoimidazolidin-1-yl)phosphonate (Compound g34), lithium (2,5-dioxo-2,5-dihydro-1H-pyrrol-1-yl)phosphonate (Compound h1), lithium ethyl (2,5-dioxo-2,5-dihydro-1H-pyrrol-1-yl)phosphonate (Compound h3), lithium 2,2,2-trifluoroethyl (2,5-dioxo-2,5-dihydro-1H-pyrrol-1-yl)phosphonate (Compound h5), lithium phenyl (2,5-dioxo-2,5-dihydro-1H-pyrrol-1-yl)phosphonate (Compound h8), lithium ethyl (2-oxopyrolidin-1-yl)phosphonate (Compound i3), lithium ethyl (2-oxopiperidin-1-yl)phosphonate (Compound i11), lithium ethyl (3-methyl-2-oxoimidazolidin-1-yl)phosphonate (Compound i19), and lithium ethyl (2-oxooxazolidin-3-yl)phosphonate (Compound i31) are especially preferred.

The compound represented by the general formula (II) is also preferably at least one selected from the group consisting of compounds represented by the following general formulae (V-I) to (V-III), in which a specified cyclic polar group is bound directly to a phosphorus atom (P).

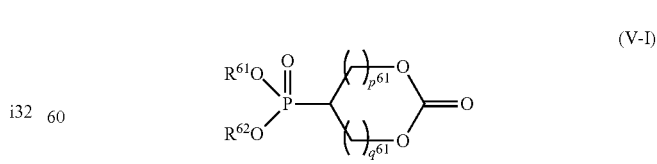

(V-I)

In the formula, $R^{61}$ and $R^{62}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom; and $p^{61}$ and $q^{61}$ each independently represent an integer of 0 to 2 and satisfy a relation: $1 \leq (p^{61}+q^{61}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (V-IV).

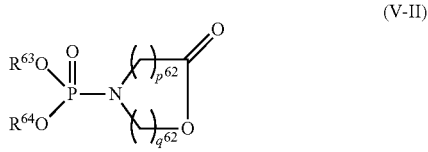

(V-II)

In the formula, $R^{63}$ and $R^{64}$ are each independently synonymous with $R^{61}$ and $R^{62}$, respectively; and $p^{62}$ and $q^{62}$ each independently represent an integer of 0 to 3 and satisfy a relation: $1 \leq (p^{62}+q^{62}) \leq 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (V-IV).

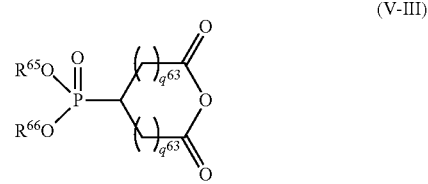

(V-III)

In the formula, $R^{65}$ and $R^{66}$ are each independently synonymous with $R^{61}$ and $R^{62}$, respectively; and $p^{63}$ and $q^{63}$ each independently represent an integer of 0 to 2 and satisfy a relation: $1 \leq (p^{63}+q^{63}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (V-IV).

(V-IV)

In the formula, $R^{71}$ and $R^{72}$ are each independently synonymous with $R^{61}$ and $R^{62}$, respectively.

Among the compounds represented by the general formulae (V-I) to (V-III), the compounds represented by the general formula (V-I) or (V-II) are more preferred, and the compounds represented by the general formula (V-I) are still more preferred.

In the general formula (V-I), $R^{61}$ and $R^{62}$ are each preferably an organic group selected from the group consisting of an alkyl group having 1 to 6 carbon atoms, an alkenyl group having 3 to 4 carbon atoms, an alkynyl group having 3 to 6 carbon atoms, and an aryl group having 6 to 12 carbon atoms, in each of which a part of hydrogen atoms may be substituted with a halogen atom; and more preferably an organic group selected from an alkyl group having 1 to 4 carbon atoms and an aryl group having 6 to 12 carbon atoms, in each of which a part of hydrogen atoms may be substituted with a halogen atom.

As specific examples of $R^{61}$ and $R^{62}$, there are suitably exemplified a straight-chain alkyl group, such as a methyl group, an ethyl group, an n-propyl group, an n-butyl group, an n-pentyl group, an n-hexyl group, an n-heptyl group, an n-octyl group, etc.; a branched alkyl group, such as an isopropyl group, a sec-butyl group, a tert-butyl group, a tert-amyl group, etc.; a cycloalkyl group, such as a cyclopropyl group, a cyclobutyl group, a cyclopentyl group, a cyclohexyl group, etc.; an alkyl group, in which a part of hydrogen atoms is substituted with a halogen atom, such as a fluoromethyl group, a difluoromethyl group, a 2-chloroethyl group, a 2-fluoroethyl group, a 2,2-difluoroethyl group, a 2,2,2-trifluoroethyl group, a 3-fluoropropyl group, a 3-chloropropyl group, a 3,3-difluoropropyl group, a 3,3,3-trifluoropropyl group, a 2,2,3,3-tetrafluoropropyl group, a 2,2,3,3,3-pentafluoropropyl group, etc.; a straight-chain alkenyl group, such as a vinyl group, a 1-propenyl group, a 2-propenyl group, a 2-butenyl group, a 3-butenyl group, a 4-pentenyl group, a 5-hexen-1-yl group, etc.; a branched alkenyl group, such as a 1-propen-2-yl group, a 1-buten-2-yl group, a 2-methyl-2-propen-1-yl group, etc.; an alkenyl group, in which a part of hydrogen atoms is substituted with a halogen atom, such as a 3,3-difluoro-2-propen-1-yl group, a 4,4-difluoro-3-buten-1-yl group, a 3,3-dichloro-2-propen-1-yl group, a 4,4-dichloro-3-buten-1-yl group, etc.; a straight-chain alkynyl group, such as a 2-propynyl group, a 2-butynyl group, a 3-butynyl group, a 4-heptynyl group, etc.; a branched alkynyl group, such as a 1-methyl-2-propynyl group, a 1,1-dimethyl-2-propynyl group, a 1-methyl-3-butynyl group, a 1-methyl-4-heptynyl group, etc.; an aryl group, such as a phenyl group, a 2-methylphenyl group, a 3-methylphenyl group, a 4-methylphenyl group, a 2,4-di-tert-butylphenyl group, a 4-tert-butylphenyl group, etc.; an aryl group, in which a part of hydrogen atoms is substituted with a halogen atom, such as a 2-fluorophenyl group, a 3-fluorophenyl group, a 4-fluorophenyl group, a 2-trifluoromethylphenyl group, a 3-trifluoromethylphenyl group, a 4-trifluoromethylphenyl group, a 4-fluoro-2-trifluoromethylphenyl group, a 4-fluoro-3-trifluoromethylphenyl group, a 2,4-difluorophenyl group, a 2,6-difluorophenyl group, a 3,5-difluorophenyl group, a 2,4,6-trifluorophenyl group, a 2,3,5,6-tetrafluorophenyl group, a perfluorophenyl group, etc.; and the like.

Among those, a methyl group, an ethyl group, an n-propyl group, an n-butyl group, a 2,2-difluoroethyl group, a 2,2,2-trifluoroethyl group, a 2-propenyl group, a 2-propynyl group, and a phenyl group are preferred; and a methyl group, an ethyl group, a 2,2,2-trifluoroethyl group, and a phenyl group are more preferred.

In the general formula (V-II), specific examples and suitable examples of $R^{63}$ and $R^{64}$ are each independently the same as the specific examples and suitable examples of $R^{61}$ and $R^{62}$, respectively. Among those, a methyl group, an ethyl group, an n-propyl group, an n-butyl group, a 2,2-difluoroethyl group, a 2,2,2-trifluoroethyl group, a 2-propenyl group, a 2-propynyl group, and a phenyl group are preferred; and a methyl group, an ethyl group, a 2,2,2-trifluoroethyl group, and a phenyl group are more preferred.

In the general formula (V-III), specific examples and suitable examples of $R^{65}$ and $R^{66}$ are each independently the same as the specific examples and suitable examples of $R^{61}$ and $R^{62}$, respectively. Among those, a methyl group, an ethyl group, an n-propyl group, an n-butyl group, a 2,2- difluoroethyl group, a 2,2,2-trifluoroethyl group, a 2-propenyl group, a 2-propynyl group, and a phenyl group are preferred; and a methyl group, an ethyl group, a 2,2,2-trifluoroethyl group, and a phenyl group are more preferred.

As the compounds represented by the general formulae (V-I) to (V-III), specifically, there are suitably exemplified the following compounds.

[Compounds Represented by General Formula (V-I)]

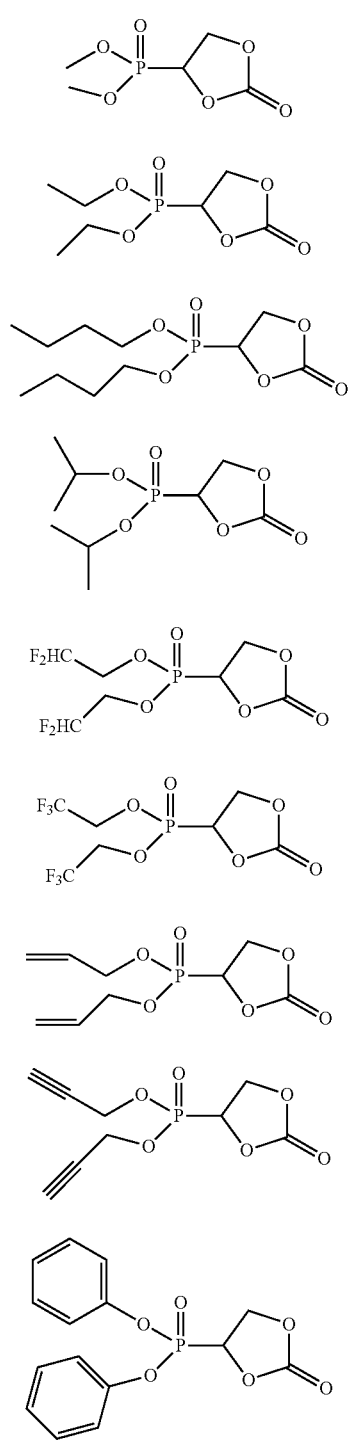

-continued

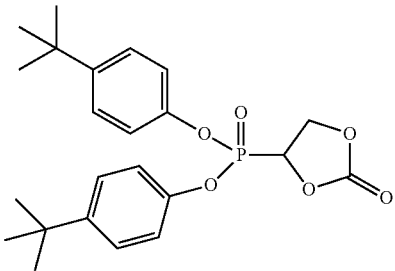

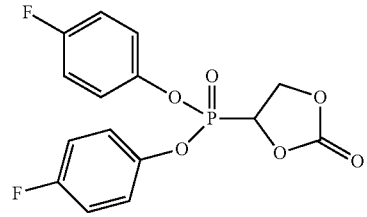

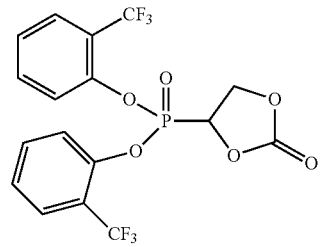

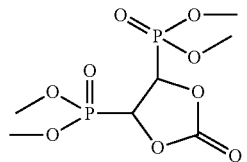

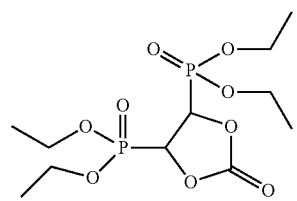

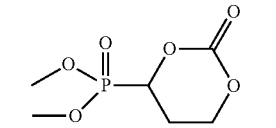

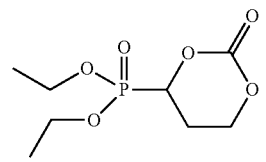

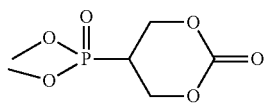

-continued
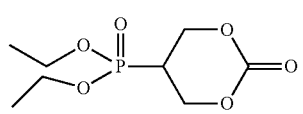
d18
[Compounds Represented by General Formula (V-II)]
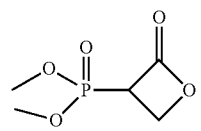
e1
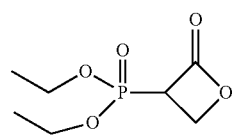
e2
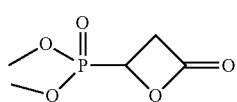
e3
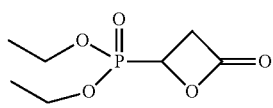
e4
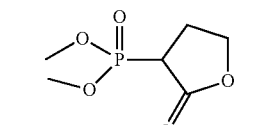
e5
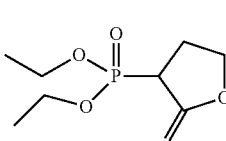
e6
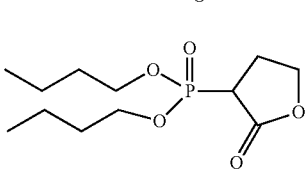
e7
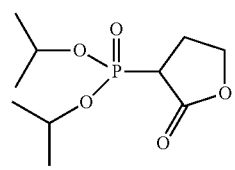
e8
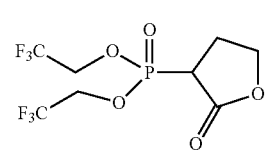
e9
-continued
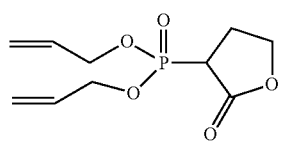
e10
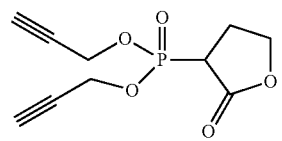
e11
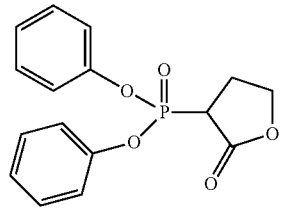
e12
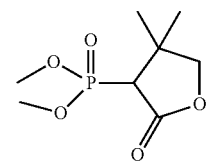
e13
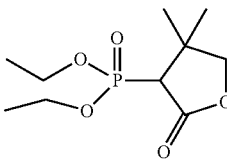
e14
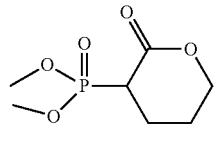
e15
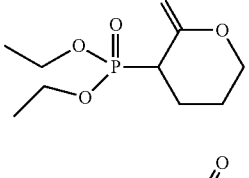
e16
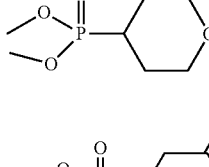
e17
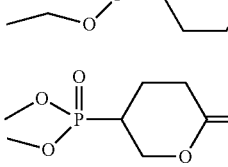
e18
e19

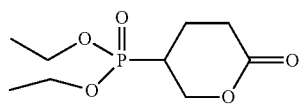

[Compounds Represented by General Formula (V-III)]

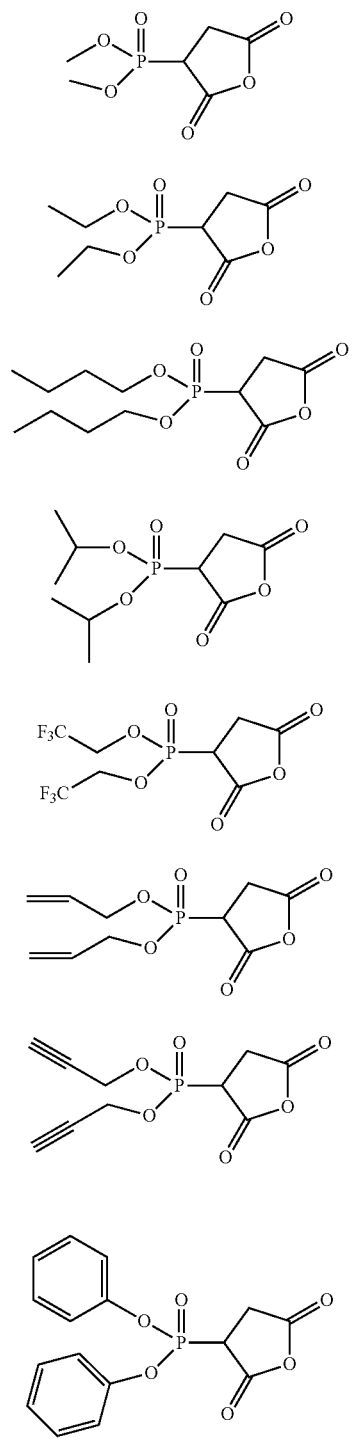

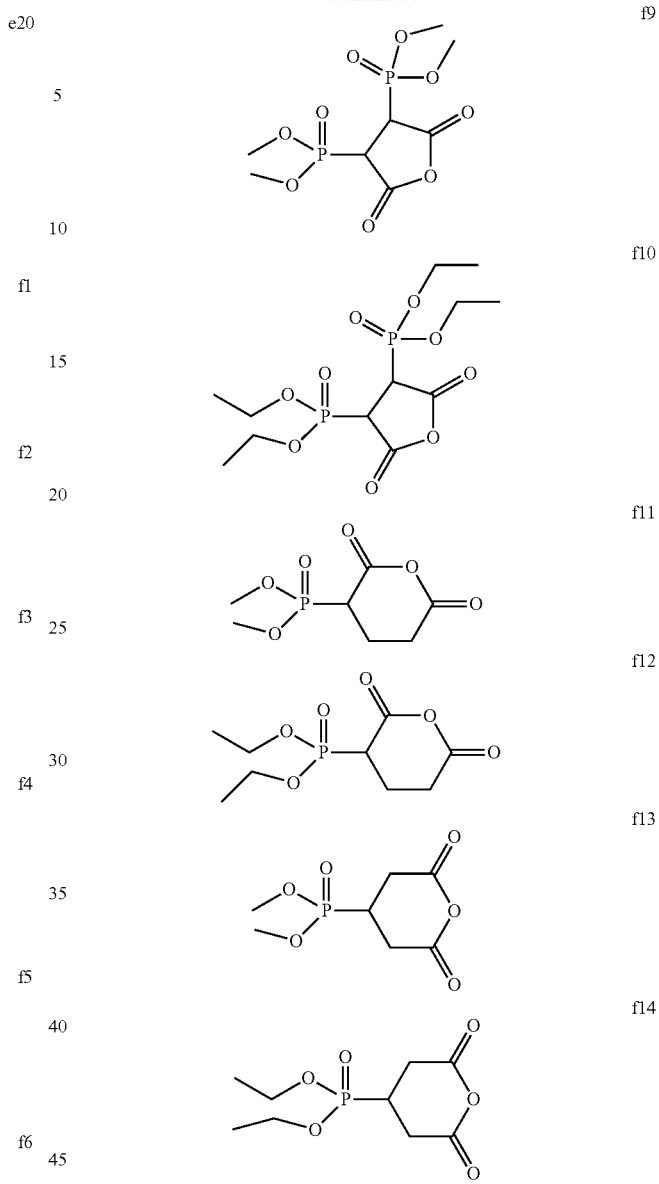

Among the aforementioned suitable examples, one or more selected from Compounds d1 to d18, e5 to e20, and f1 to f14 are preferred; one or more selected from Compounds d1 to d3, d5 to d18, e5 to e7, e9 to e20, f1 to f3, and f5 to f14 are more preferred; and one or more selected from dimethyl (2-oxo-1,3-dioxolan-4-yl)phosphonate (Compound d1), diethyl (2-oxo-1,3-dioxolan-4-yl)phosphonate (Compound d2), bis(2,2,2-trifluoroethyl) (2-oxo-1,3-dioxolan-4-yl)phosphonate (Compound d6), diphenyl (2-oxo-1,3-dioxolan-4-yl)phosphonate (Compound d9), dimethyl (2-oxotetrahydrofuran-3-yl)phosphonate (Compound e5), diethyl (2-oxotetrahydrofuran-3-yl)phosphonate (Compound e6), bis(2,2,2-trifluoroethyl) (2-oxotetrahydrofuran-3-yl)phosphonate (Compound e9), diphenyl (2-oxotetrahydrofuran-3-yl)phosphonate (Compound e12), dimethyl (2,5-dioxotetrahydrofuran-3-yl)phosphonate (Compound f1), diethyl (2,5-dioxotetrahydrofuran-3-yl)phosphonate (Compound f2), bis(2,2,2-trifluoroethyl) (2,5-dioxotetrahydrofuran-3-yl)phosphonate (Compound f5), diphenyl (2,5-dioxotetrahydrofuran-3-yl)phosphonate (Compound f8), and tetraethyl (2,5-dioxotetrahydrofuran-3,4-diyl)bis(phosphonate) (Compound f10) are especially preferred.

In the nonaqueous electrolytic solution of the second invention, a content of the compound represented by the general formula (II), which is contained in the nonaqueous electrolytic solution, is preferably 0.001 to 10 mass % in the nonaqueous electrolytic solution. When the content is 10 mass % or less, there is less concern of occurrence of the matter that a surface film is excessively formed on an electrode, so that the low-temperature properties are worsened, whereas when it is 0.001 mass % or more, the formation of a surface film is sufficient, and an improving effect of the electrochemical characteristics in a broad temperature range is enhanced, and hence, the aforementioned range is preferred. The content is more preferably 0.05 mass % or more, and still more preferably 0.1 mass % or more in the nonaqueous electrolytic solution. An upper limit thereof is more preferably 7 mass % or less, still more preferably 5 mass % or less, and especially preferably 3 mass % or less.

In the nonaqueous electrolytic solution of the second invention, by combining the compound represented by the general formula (II) with a nonaqueous solvent, an electrolyte salt, and further other additives as mentioned later, a peculiar effect of synergistically improving the electrochemical characteristics in a broad temperature range is revealed.

<Nonaqueous Electrolytic Solution of Third Invention>

The compound that is contained in the nonaqueous electrolytic solution of the third invention, in which a specified polar group ($X^3$) is bound to a phosphorus atom (P), is represented by the following general formula (III).

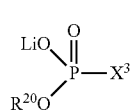

(III)

In the formula, $R^{20}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^3$ is a polar group containing a —C(=O) group, a —P(=O) group, an —S(=O)$_2$ group, a —CN group, or an alkyl group having 1 to 6 carbon atoms, in which a part of hydrogen atoms is substituted with a fluorine atom.

In the general formula (III), $R^{20}$ is preferably an organic group selected from the group consisting of an alkyl group having 1 to 6 carbon atoms, an alkenyl group having 3 to 4 carbon atoms, an alkynyl group having 3 to 6 carbon atoms, and an aryl group having 6 to 10 carbon atoms, in each of which a part of hydrogen atoms may be substituted with a halogen atom, or a lithium atom; more preferably an organic group selected from the group consisting of an alkyl group having 1 to 4 carbon atoms, an alkenyl group having 2 to 4 carbon atoms, and an alkynyl group having 3 to 4 carbon atoms, in each of which a part of hydrogen atoms may be substituted with a halogen atom; and especially preferably an alkyl group having 1 to 4 carbon atoms.

Specific examples of the organic group represented by $R^{20}$, in which a part of hydrogen atoms may be substituted with a halogen atom, are the same as the specific examples of $R^{20}$ of the general formula (I) in the first invention.

Among those, a methyl group, an ethyl group, an n-propyl group, an n-butyl group, a 2,2-difluoroethyl group, a 2,2,2-trifluoroethyl group, a 2-propenyl group, a 2-propynyl group, and a phenyl group are preferred; a methyl group, an ethyl group, a 2,2,2-trifluoroethyl group, a 2-propenyl group, and a 2-propynyl group are more preferred; and a methyl group and an ethyl group are still more preferred.

The compound represented by the general formula (III) is at least one compound represented by any of the following general formulae (III-1) to (III-7).

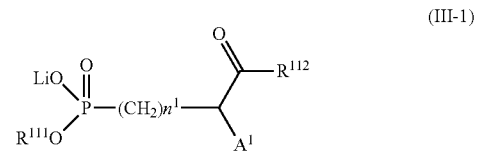

(III-1)

In the formula, $A^1$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{113}$ group, an —OC(=O)—OR$^{114}$ group, an —S(=O)$_2R^{115}$ group, or an —S(=O)$_2$OR$^{116}$ group; $R^{111}$, $R^{114}$, and $R^{116}$ each independently represent an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; $R^{112}$, $R^{113}$, and $R^{115}$ each represent an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atoms; and $n^1$ represents an integer of 0 to 2.

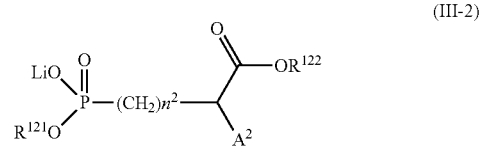

(III-2)

In the formula, $A^2$ represents an alkoxy group having 1 to 8 carbon atoms, in which a part of hydrogen atoms may be substituted with a halogen atom, an —OC(=O)$R^{123}$ group, an —OC(=O)—OR$^{124}$ group, an —S(=O)$_2R^{125}$ group, or an —S(=O)$_2$OR$^{126}$ group; $R^{121}$, $R^{122}$, $R^{124}$, and $R^{126}$ are each independently synonymous with $R^{20}$; $R^{123}$ and $R^{125}$ are each independently synonymous with $R^{113}$ and $R^{115}$, respectively; and $n^2$ represents an integer of 0 to 2.

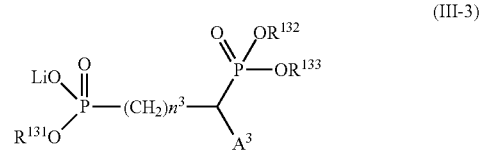

(III-3)

In the formula, $A^3$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{134}$ group, an —OC(=O)—O$R^{135}$ group, an —S(=O)$_2R^{136}$ group, or an —S(=O)$_2$O$R^{137}$ group; $R^{131}$, $R^{132}$, $R^{133}$, $R^{135}$, and $R^{137}$ are each independently synonymous with $R^{20}$; $R^{134}$ and $R^{136}$ are each independently synonymous with $R^{113}$ and $R^{115}$, respectively; and $n^3$ represents an integer of 0 to 2.

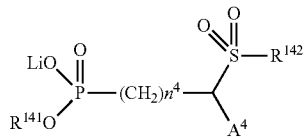

(III-4)

In the formula, $A^4$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{143}$ group, an —OC(=O)—O$R^{144}$ group, an —S(=O)$_2R^{145}$ group, or an —S(=O)$_2$O$R^{146}$ group; $R^{141}$, $R^{144}$, and $R^{146}$ are each independently synonymous with $R^{20}$; $R^{142}$, $R^{143}$, and $R^{145}$ are each independently synonymous with $R^{113}$ and $R^{115}$, respectively; and $n^4$ represents an integer of 0 to 2.

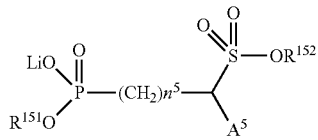

(III-5)

In the formula, $A^5$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{153}$ group, an —OC(=O)—O$R^{154}$ group, an —S(=O)$_2R^{155}$ group, or an —S(=O)$_2$O$R^{156}$ group; $R^{151}$, $R^{152}$, $R^{154}$, and $R^{156}$ are each independently synonymous with $R^{20}$; $R^{153}$ and $R^{155}$ are each independently synonymous with $R^{113}$ and $R^{115}$, respectively; and $n^5$ represents an integer of 0 to 2.

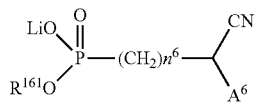

(III-6)

In the formula, $A^6$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{162}$ group, an —OC(=O)—O$R^{163}$ group, an —S(=O)$_2R^{164}$ group, or an —S(=O)$_2$O$R^{165}$ group; $R^{161}$, $R^{163}$, and $R^{165}$ are each independently synonymous with $R^{20}$; $R^{162}$ and $R^{164}$ are each independently synonymous with $R^{113}$ and $R^{115}$, respectively; and $n^6$ represents an integer of 0 to 2.

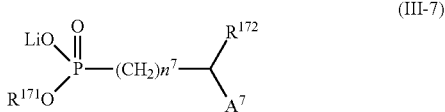

(III-7)

In the formula, $R^{172}$ represents an alkyl group having 1 to 6 carbon atoms, in which a part of hydrogen atoms are substituted with a fluorine atom; $A^7$ represents an alkoxy group having 1 to 8 carbon atoms, in which a part of hydrogen atoms may be substituted with a halogen atom, an —OC(=O)$R^{173}$ group, an —OC(=O)—O$R^{174}$ group, an —S(=O)$_2R^{175}$ group, or an —S(=O)$_2$O$R^{176}$ group; $R^{171}$, $R^{174}$, and $R^{176}$ are each independently synonymous with $R^{20}$; $R^{173}$ and $R^{175}$ are each independently synonymous with $R^{113}$ and $R^{115}$, respectively; and $n^7$ represents an integer of 0 to 2.

Among the compounds represented by any of the general formulae (III-1) to (III-7), the compounds represented by the general formulae (III-2) to (III-4) are more preferred, and the compounds represented by the general formula (III-2) or (III-3) are still more preferred.

In the general formulae (III-1) to (III-7), preferred ranges of $R^{111}$, $R^{114}$, $R^{116}$, $R^{121}$, $R^{122}$, $R^{124}$, $R^{126}$, $R^{131}$, $R^{132}$, $R^{133}$, $R^{135}$, $R^{137}$, $R^{141}$, $R^{144}$, $R^{146}$, $R^{151}$, $R^{152}$, $R^{154}$, $R^{156}$, $R^{161}$, $R^{163}$, $R^{165}$, $R^{171}$, $R^{174}$, and $R^{176}$ are each synonymous with those of $R^{20}$; and $R^{112}$, $R^{113}$, $R^{115}$, $R^{123}$, $R^{125}$, $R^{134}$, $R^{136}$, $R^{142}$, $R^{143}$, $R^{145}$, $R^{153}$, $R^{155}$, $R^{162}$, $R^{164}$, $R^{173}$, and $R^{175}$ each represent an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, preferably an organic group selected from the group consisting of an alkyl group having 1 to 6 carbon atoms, an alkenyl group having 3 to 4 carbon atoms, an alkynyl group having 3 to 6 carbon atoms, and an aryl group having 6 to 10 carbon atoms, in each of which a part of hydrogen atoms may be substituted with a halogen atom, more preferably an organic group selected from the group consisting of an alkyl group having 1 to 4 carbon atoms, an alkenyl group having 2 to 4 carbon atoms, and an alkynyl group having 3 to 4 carbon atoms, in each of which a part of hydrogen atoms may be substituted with a halogen atom, and especially preferably an alkyl group having 1 to 4 carbon atoms.

Specific examples in the case where $R^{112}$, $R^{113}$, $R^{115}$, $R^{123}$, $R^{125}$, $R^{134}$, $R^{136}$, $R^{142}$, $R^{143}$, $R^{145}$, $R^{153}$, $R^{155}$, $R^{162}$, $R^{164}$, $R^{173}$, and $R^{175}$ each represent an organic group, in which a part of hydrogen atoms may be substituted with a halogen atom, are the same as the specific examples of $R^{20}$ of the general formula (I) in the first invention.

Among those, a methyl group, an ethyl group, an n-propyl group, an n-butyl group, a trifluoromethyl group, a 2,2,2-trifluoroethyl group, a 2-propenyl group, a 2-propynyl group, and a phenyl group are preferred; a methyl group, an ethyl group, a trifluoromethyl group, a 2-propenyl group, and a 2-propynyl group are more preferred; and a methyl group and an ethyl group are still more preferred.

In the general formula (III-7), $R^{172}$ represents an alkyl group having 1 to 6 carbon atoms, in which a part of hydrogen atoms is substituted with a halogen atom, preferably an alkyl group having 1 to 4 carbon atoms, in which a part of hydrogen atoms is substituted with a halogen atom, and more preferably an alkyl group having 1 carbon atom or 2 carbon atoms, in which all of hydrogen atoms are substituted with a halogen atom.

As specific examples of $R^{172}$, there are suitably exemplified a fluoromethyl group, a difluoromethyl group, a trifluoromethyl group, a 2,2,2-trifluoroethyl group, a 1,1,2,2-tetrafluoroethyl group, a perfluoroethyl group, a 2,2,3,3-tetrafluoropropyl group, a perfluoropropyl group, a perfluorobutyl group, and a perfluoropentyl group. Among those, a difluoromethyl group, a trifluoromethyl group, a 2,2,2-trifluoroethyl group, a 1,1,2,2-tetrafluoroethyl group, a perfluoroethyl group, a 2,2,3,3-tetrafluoropropyl group, and a perfluoropropyl group are preferred, and a trifluoromethyl group and a perfluoroethyl group are more preferred.

As the compounds represented by any of the general formulae (III-1) to (III-7), in which the specified polar group is bound to the phosphorus atom (P), specifically, there are suitably exemplified the following compounds.

[Compounds Represented by General Formula (III-1)]

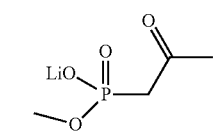
A1

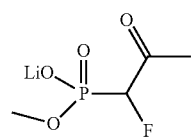
A2

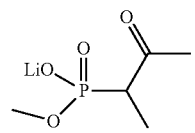
A3

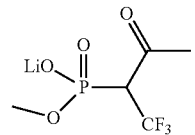
A4

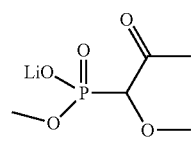
A5

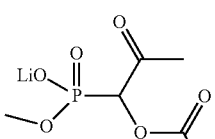
A6

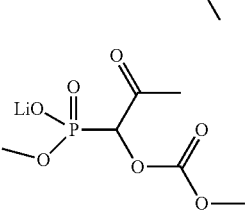
A7

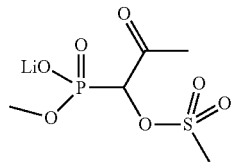
A8

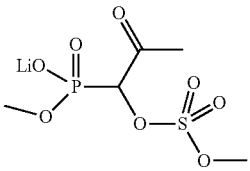
A9

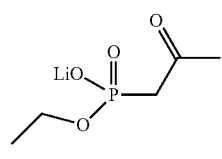
A10

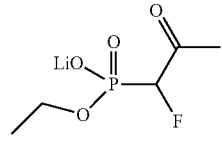
A11

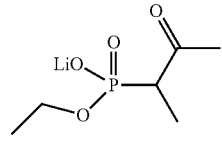
A12

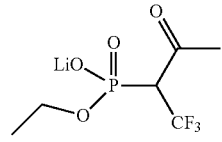
A13

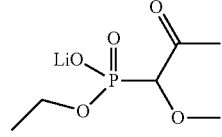
A14

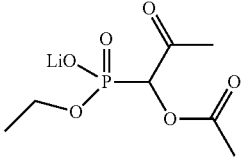
A15

A16

-continued
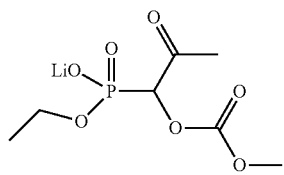
A17
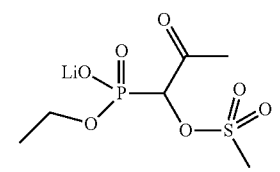
A18
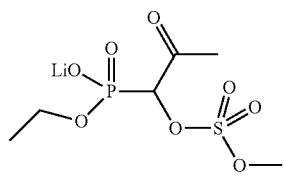
A19
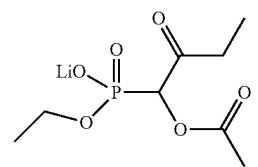
A20
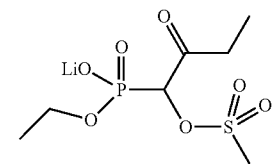
A21
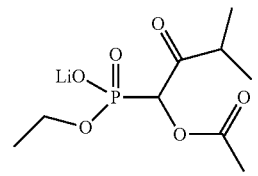
A22
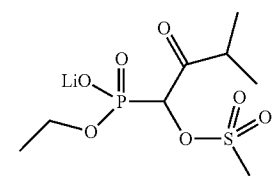
A23
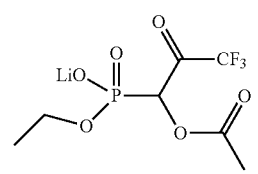
A24
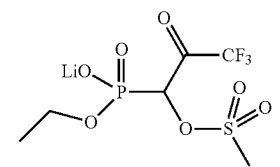
A25
-continued
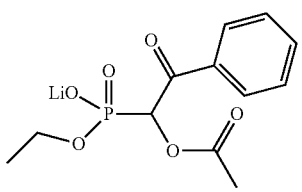
A26
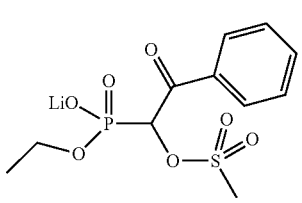
A27
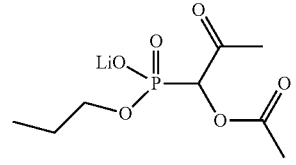
A28
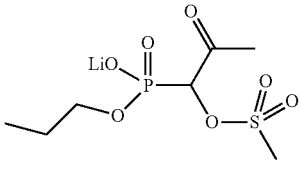
A29
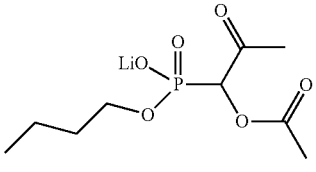
A30
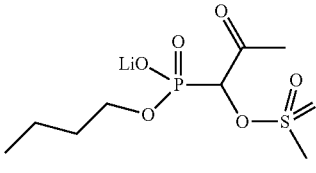
A31
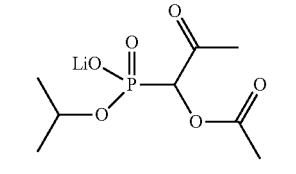
A32
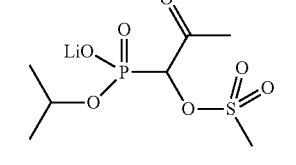
A33
A34

-continued
| | | |
|---|---|---|
| 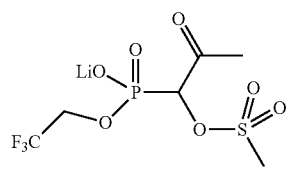 | A35 | |
| 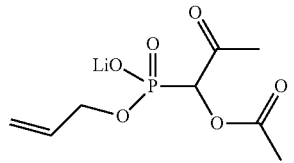 | A36 | |
| 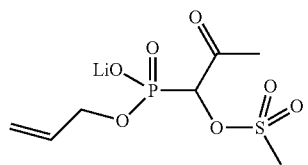 | A37 | |
| 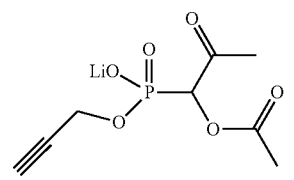 | A38 | |
| 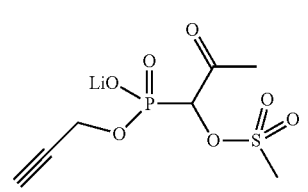 | A39 | |
| 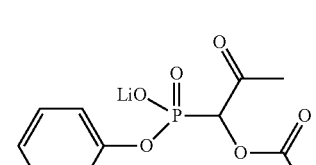 | A40 | |
| 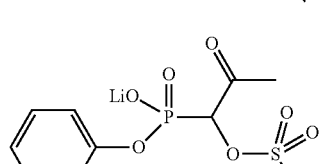 | A41 | |
| 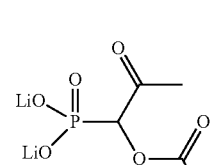 | A42 | |
| 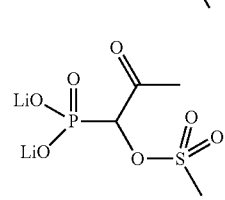 | A43 | |
-continued
| | | |
|---|---|---|
| 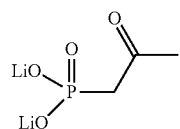 | A44 | |
| 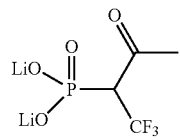 | A45 | |
| 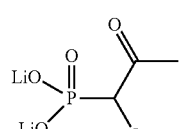 | A46 | |
| 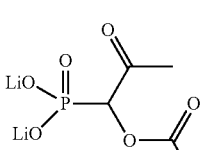 | A47 | |
| 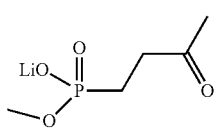 | A48 | |
| 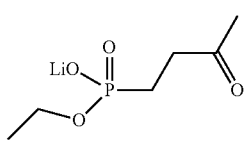 | A49 | |
| 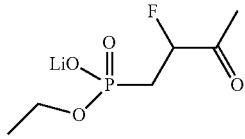 | A50 | |
| 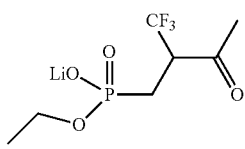 | A51 | |
| 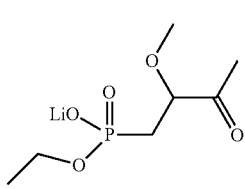 | A52 | |
| 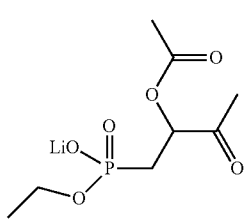 | A53 | |

A54 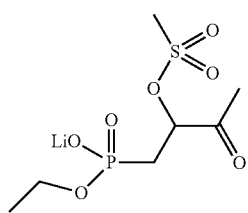
A55 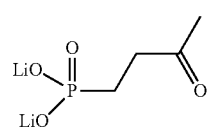
A56 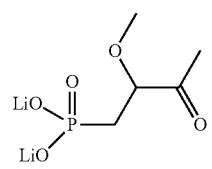
A57 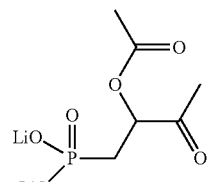
A58 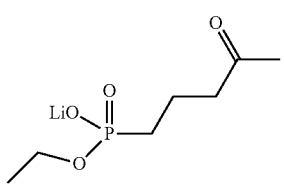
[Compounds Represented by General Formula (III-2)]
B1 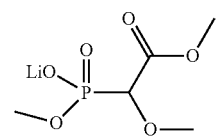
B2 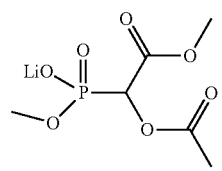
B3 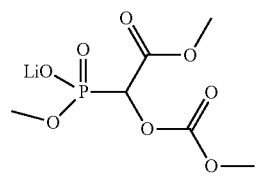
B4 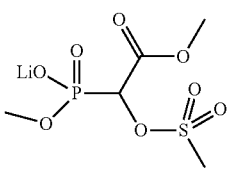
B5 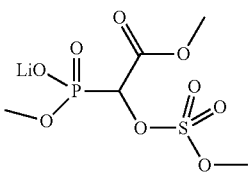
B6 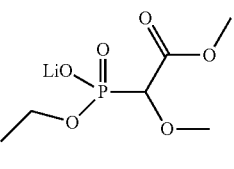
B7 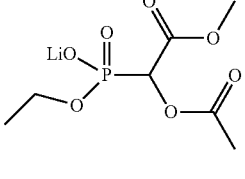
B8 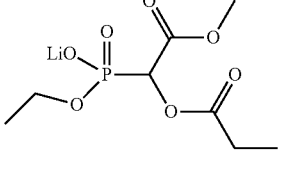
B9 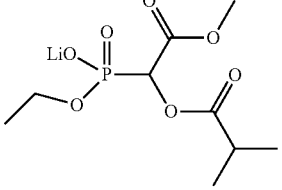
B10 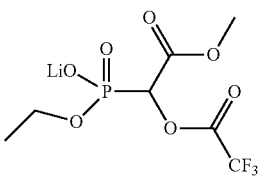
B11 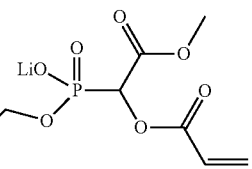

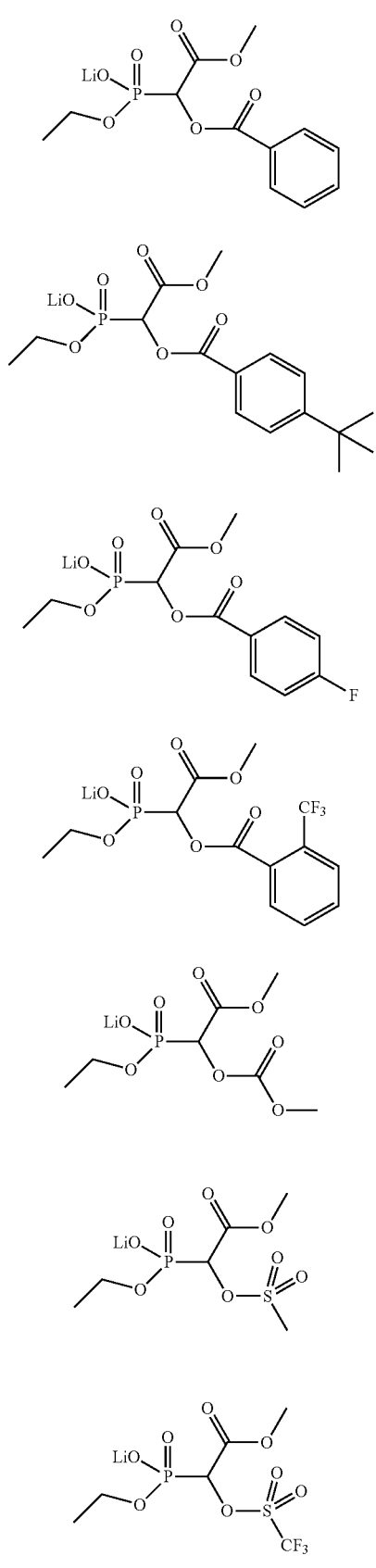
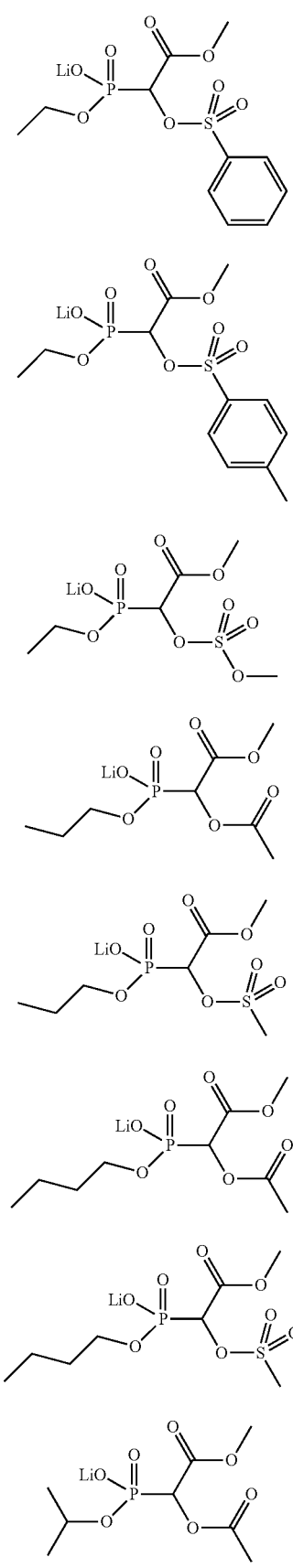

B27 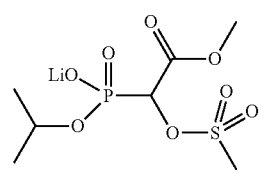
B28 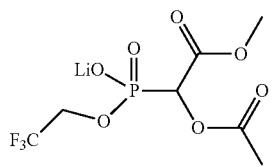
B29 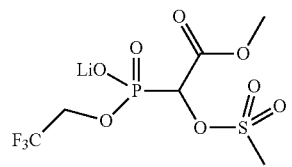
B30 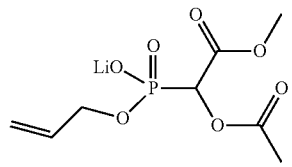
B31 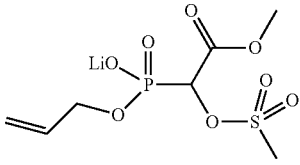
B32 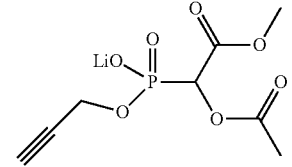
B33 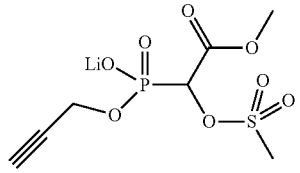
B34 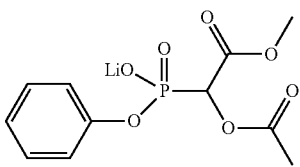
B35 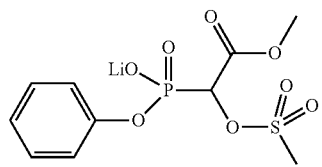
B36 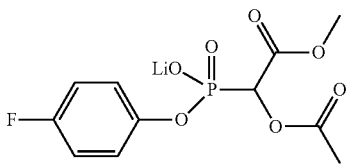
B37 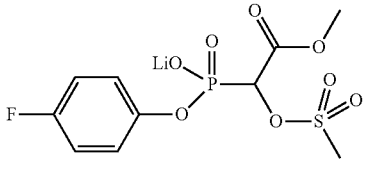
B38 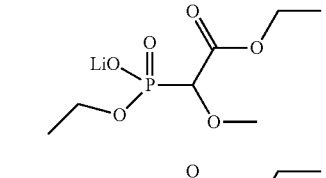
B39 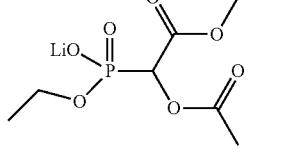
B40 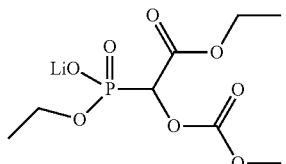
B41 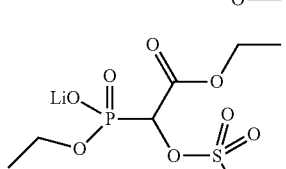
B42 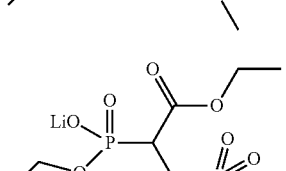
B43 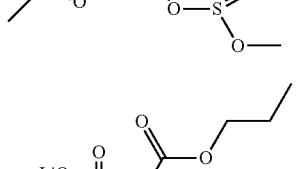
B44 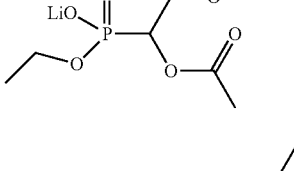

B45 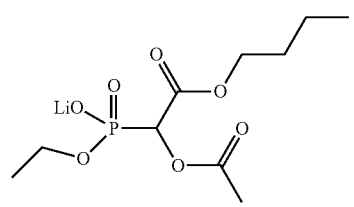
B46 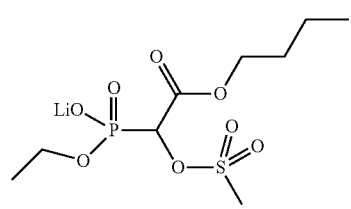
B47 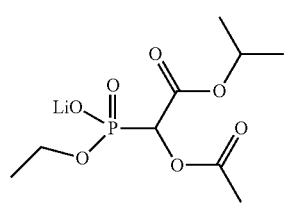
B48 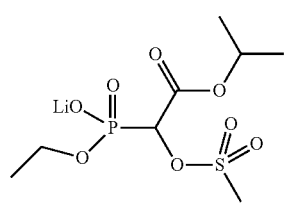
B49 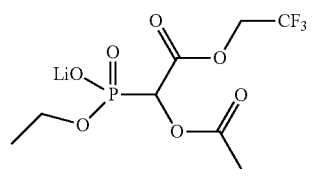
B50 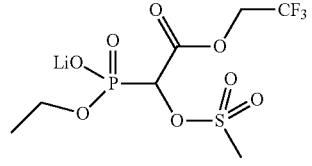
B51 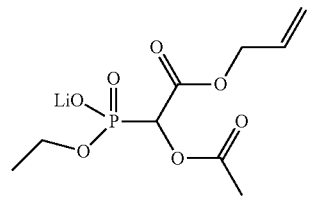
B52 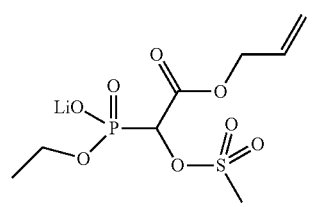
B53 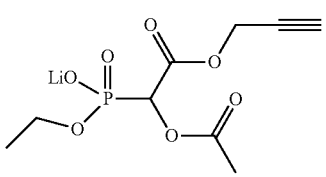
B54 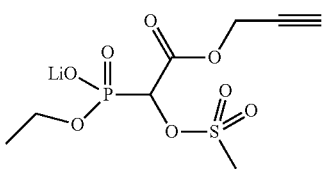
B55 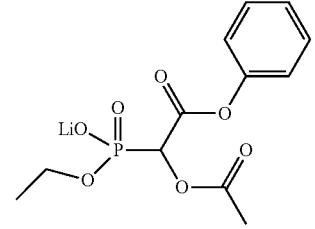
B56 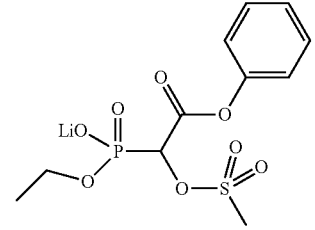
B57 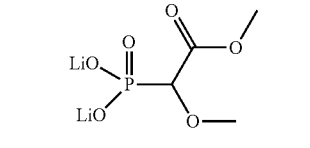
B58 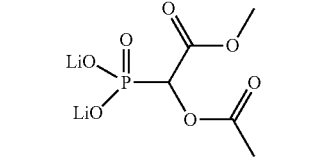
B59 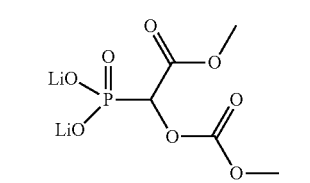
B60 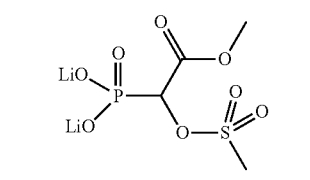

-continued
B61 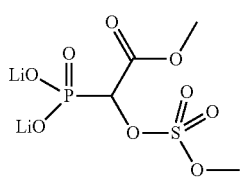
B62 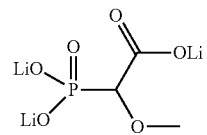
B63 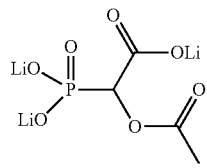
B64 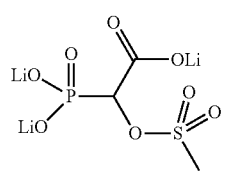
B65 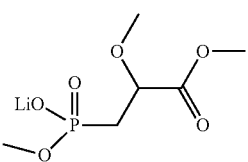
B66 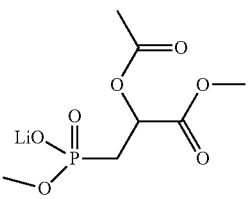
B67 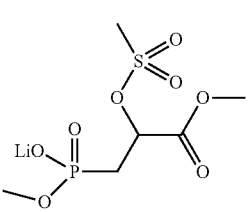
B68 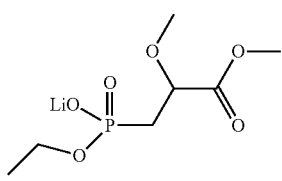
-continued
B69 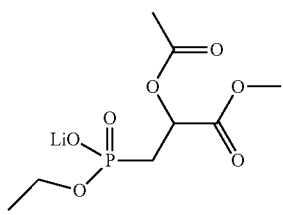
B70 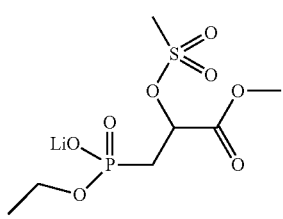
B71 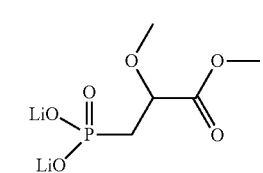
B72 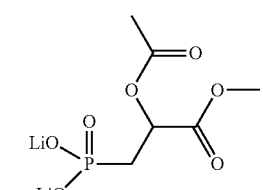
B73 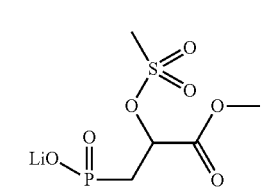
B74 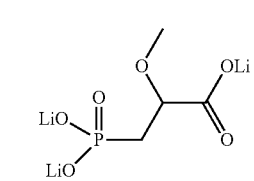
B75 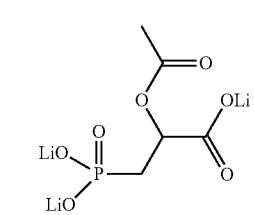
B76 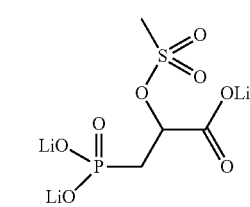

| B77 | 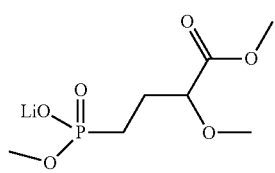 |
| B78 | 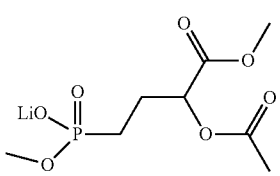 |
| B79 | 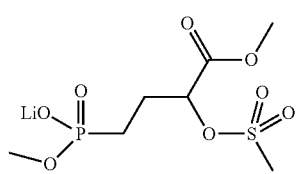 |
[Compounds Represented by General Formula (III-3)]
| C1 | 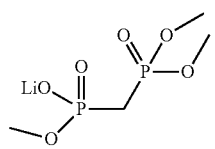 |
| C2 | 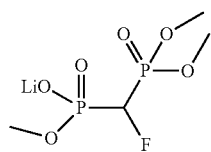 |
| C3 | 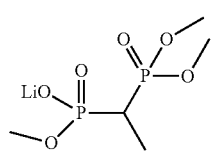 |
| C4 | 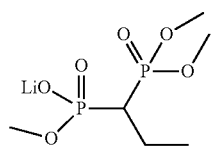 |
| C5 | 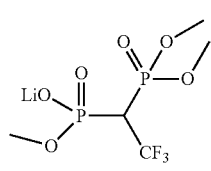 |
| C6 | 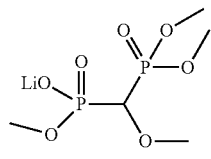 |
| C7 | 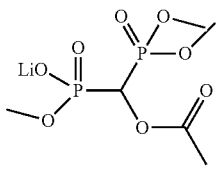 |
| C8 | 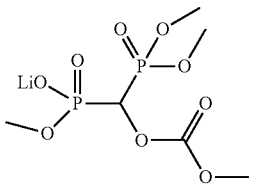 |
| C9 | 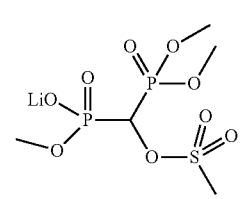 |
| C10 | 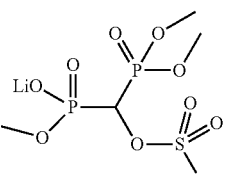 |
| C11 | 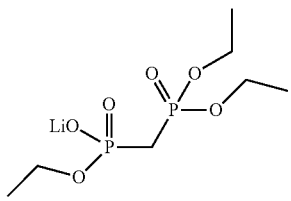 |
| C12 | 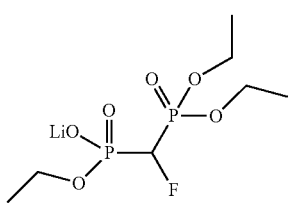 |
| C13 | 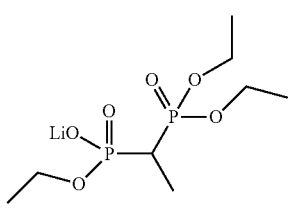 |
| C14 | 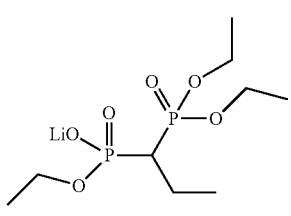 |

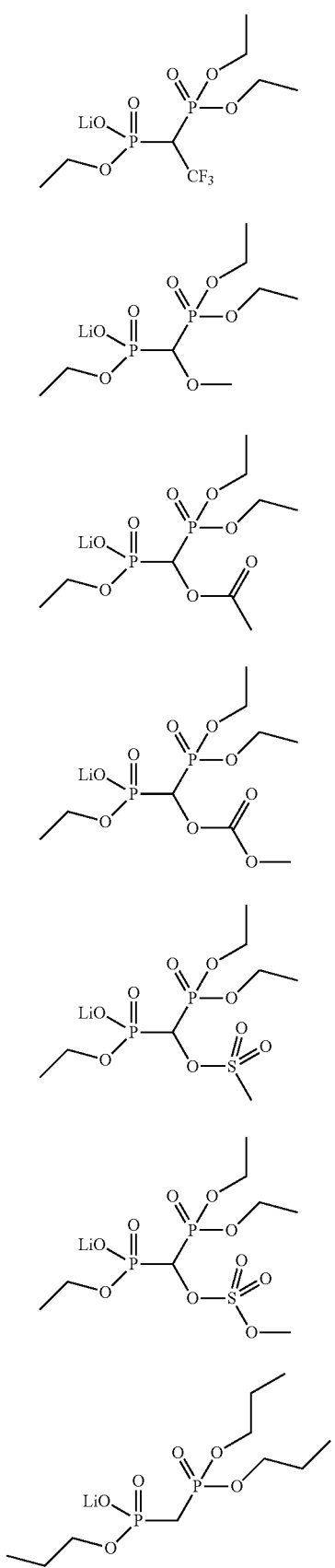
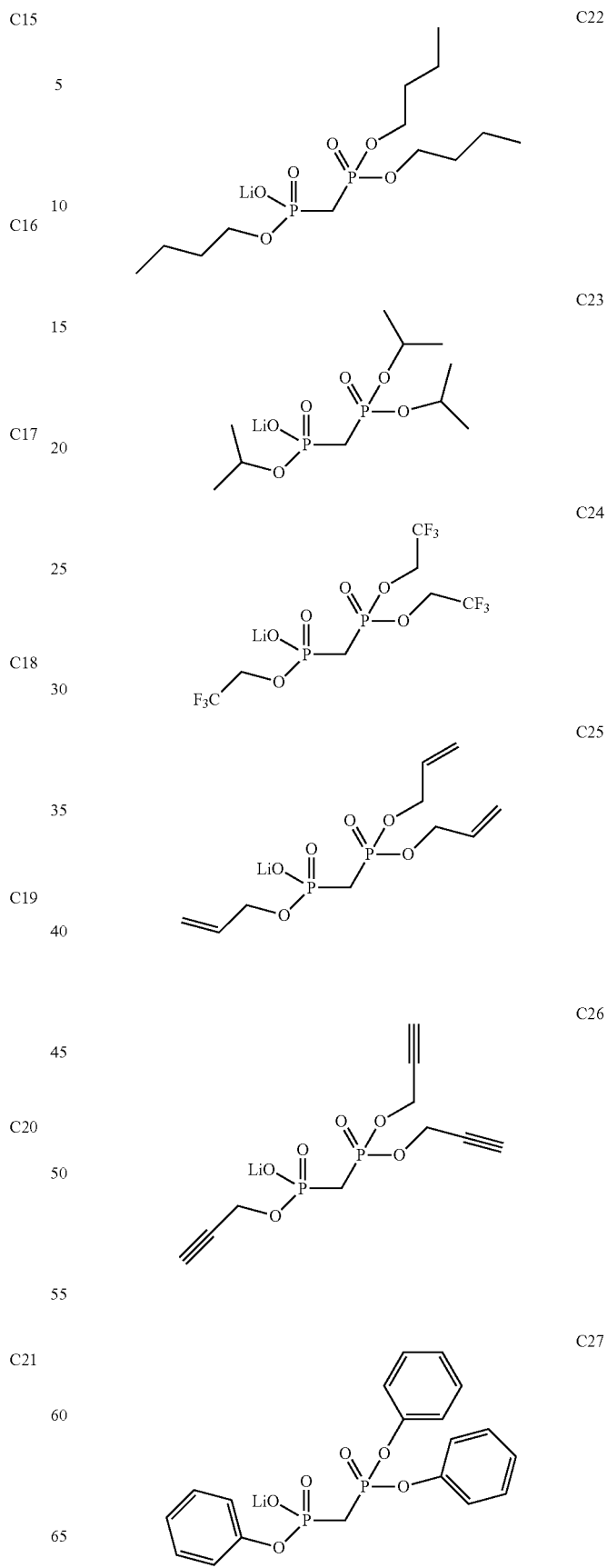

C28
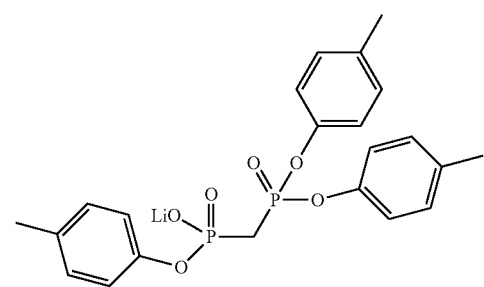
C29
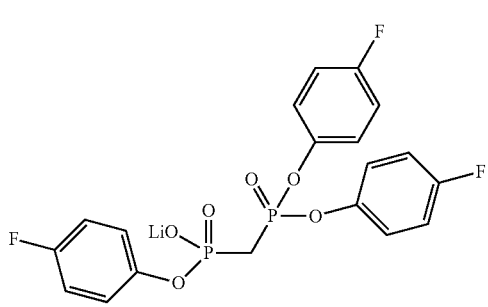
C30
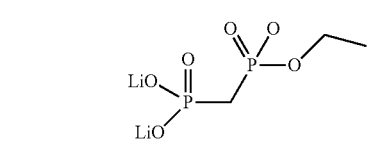
C31
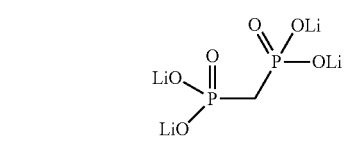
C32
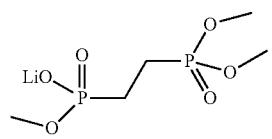
C33
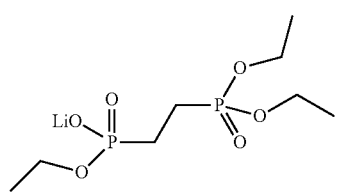
C34
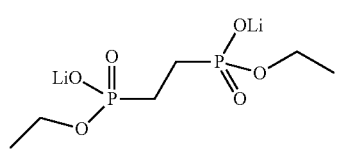
C35
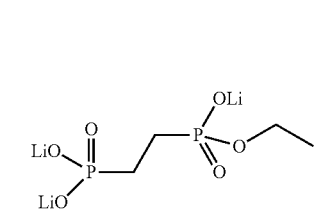
C36
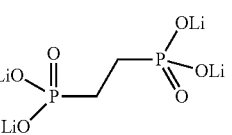
C37
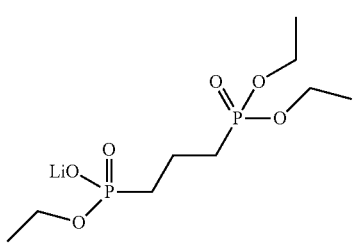
C38
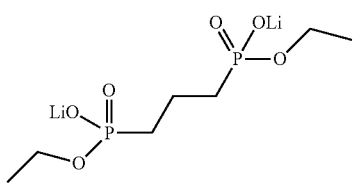
[Compounds Represented by General Formula (III-4)]
D1
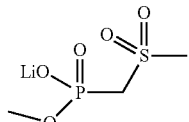
D2
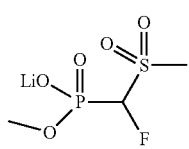
D3
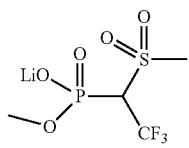
D4
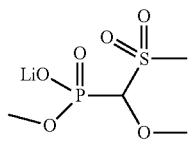
D5
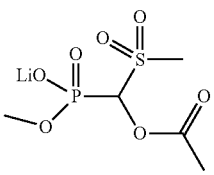

-continued
D6 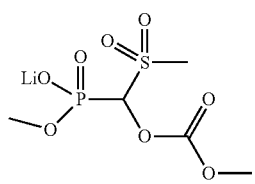
D7 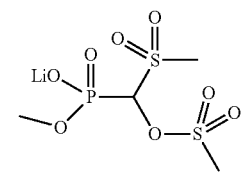
D8 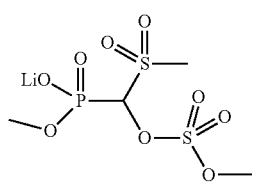
D9 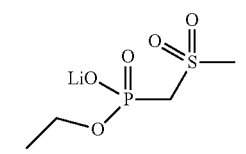
D10 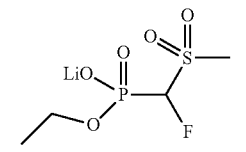
D11 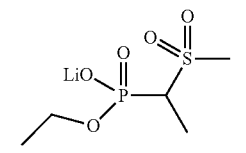
D12 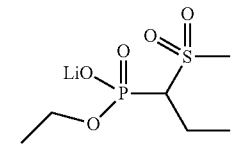
D13 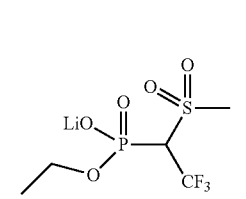
D14 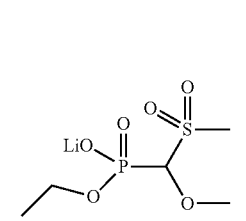
-continued
D15 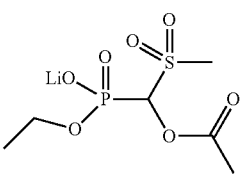
D16 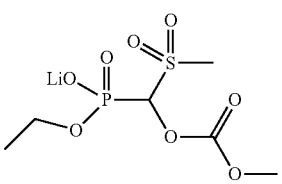
D17 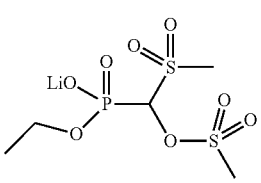
D18 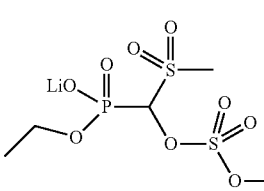
D19 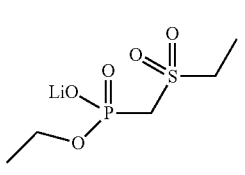
D20 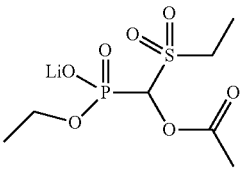
D21 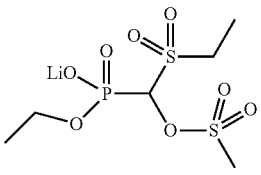
D22 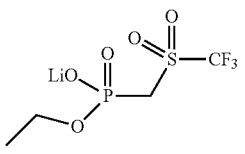
D23

-continued
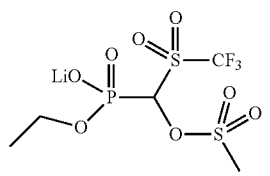
D24
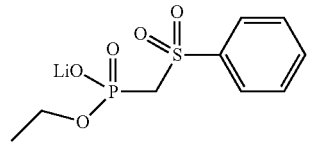
D25
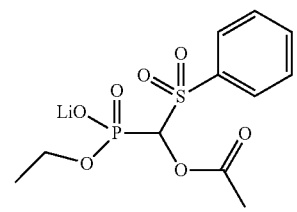
D26
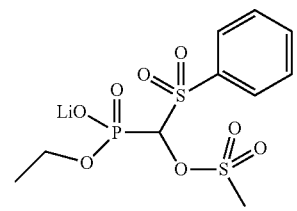
D27
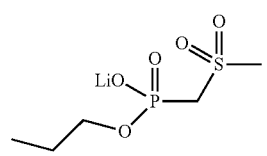
D28
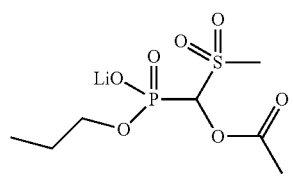
D29
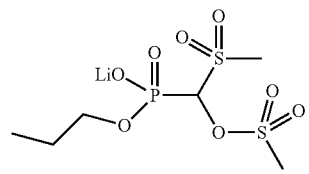
D30
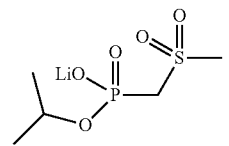
D31
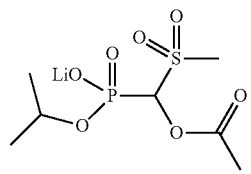
D32
-continued
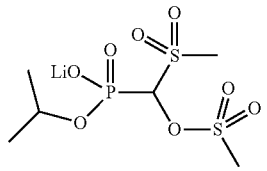
D33
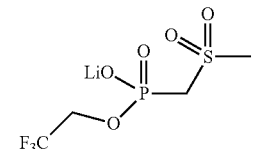
D34
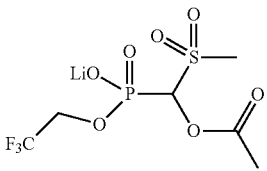
D35
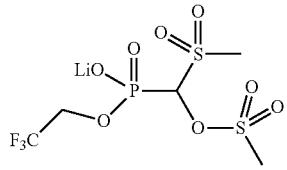
D36
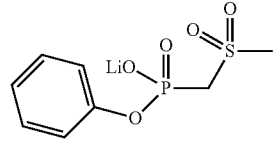
D37
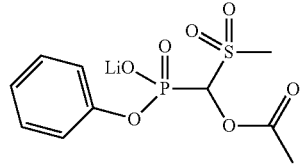
D38
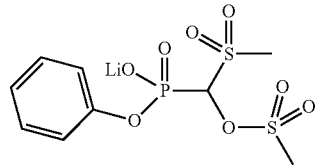
D39
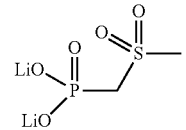
D40
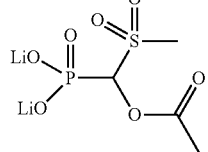
D41

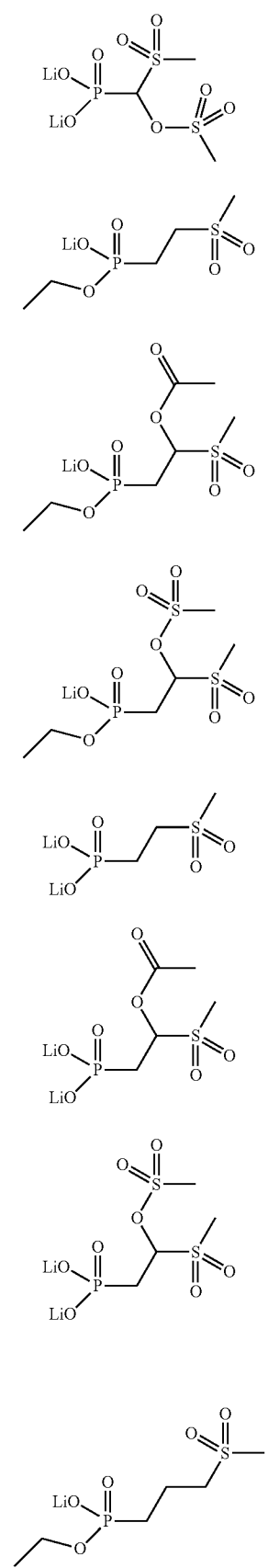
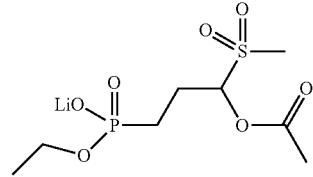
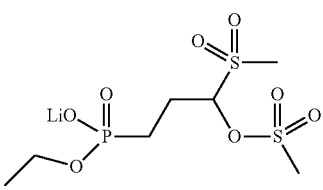
[Compounds Represented by General Formula (III-5)]

| | |
|---|---|
| E7 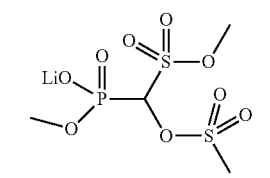 | E16 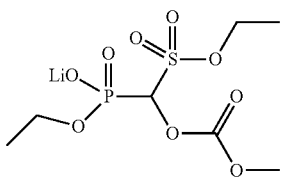 |
| E8 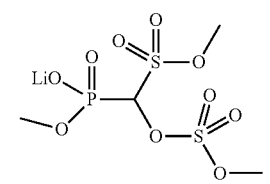 | E17 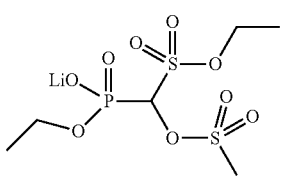 |
| E9 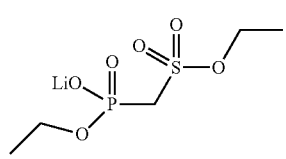 | E18 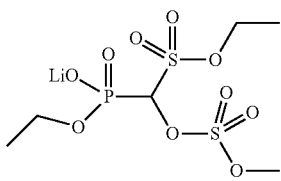 |
| E10 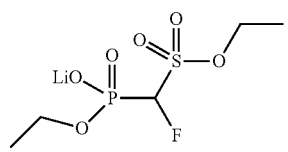 | E19 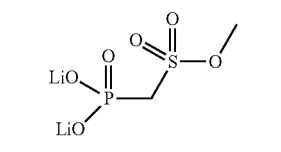 |
| E11 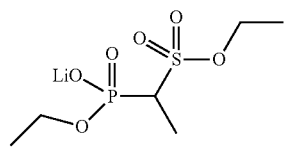 | E20 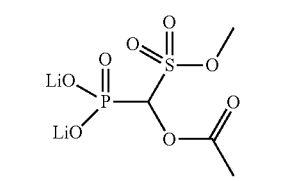 |
| E12 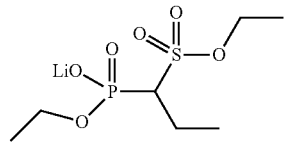 | E21 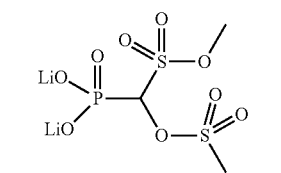 |
| E13 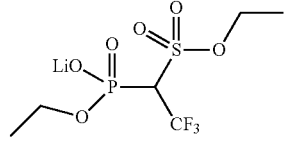 | E22 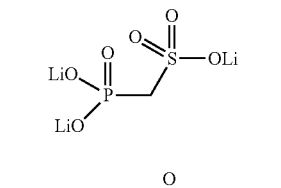 |
| E14 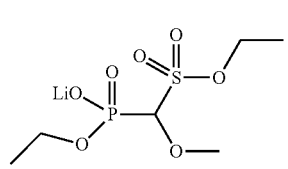 | E23 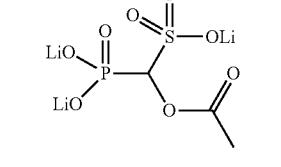 |
| E15 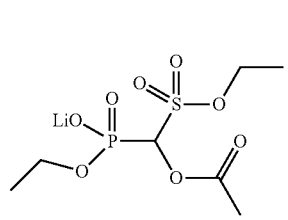 | E24 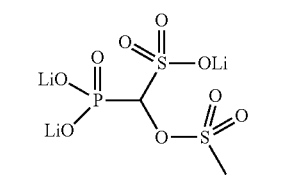 |

E25 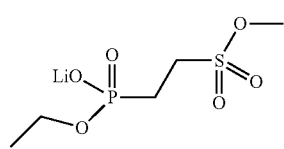
E26 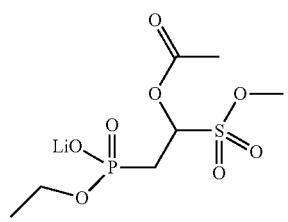
E27 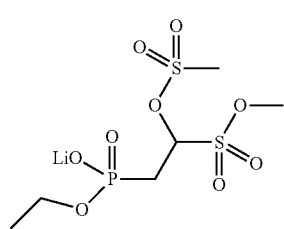
E28 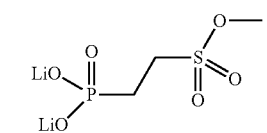
E29 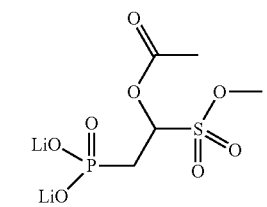
E30 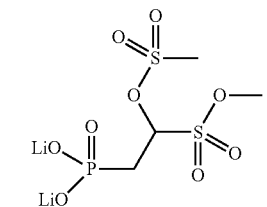
E31 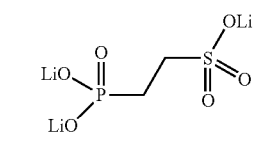
E32 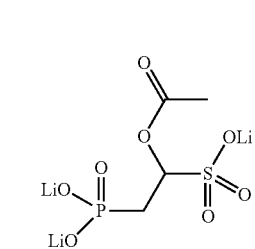
E33 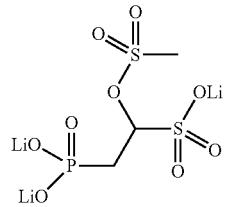
E34 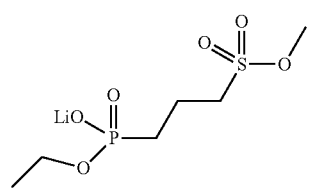
E35 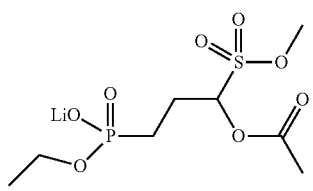
E36 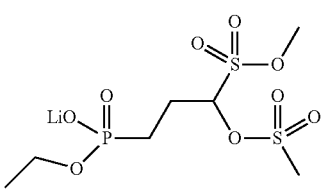
[Compounds Represented by General Formula (III-6)]
F1 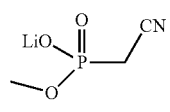
F2 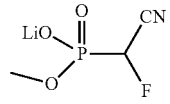
F3 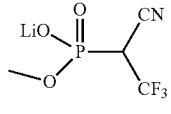
F4 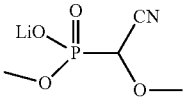
F5 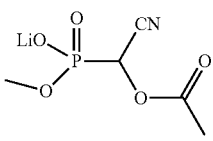

-continued
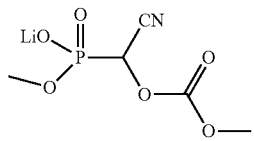 F6
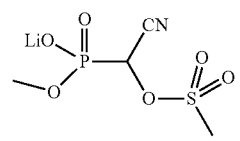 F7
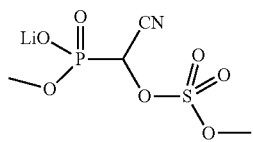 F8
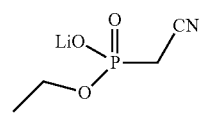 F9
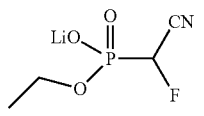 F10
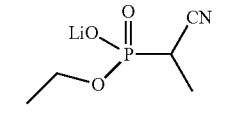 F11
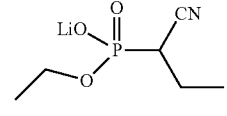 F12
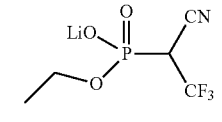 F13
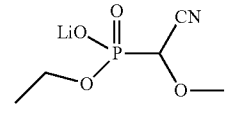 F14
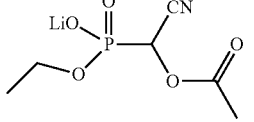 F15
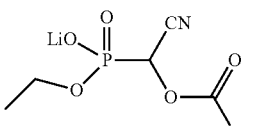 F16
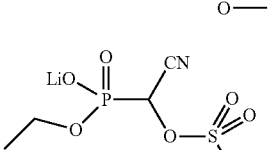 F17
-continued
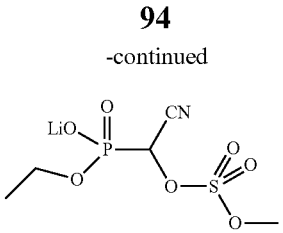 F18
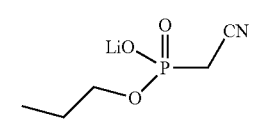 F19
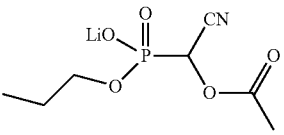 F20
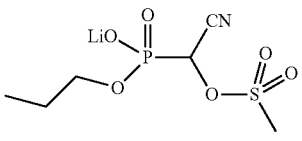 F21
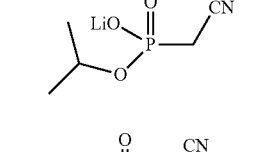 F22
F23
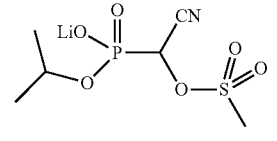 F24
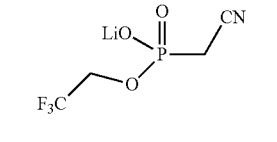 F25
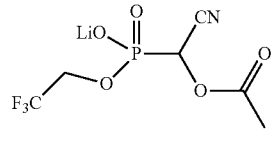 F26
F27
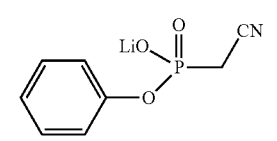 F28

[Compounds Represented by General Formula (III-7)]

-continued
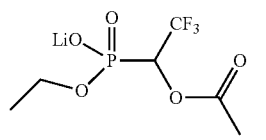 G7
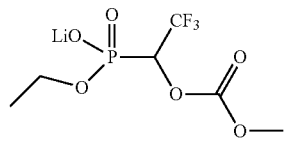 G8
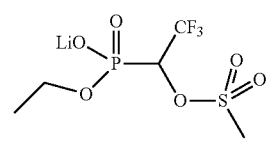 G9
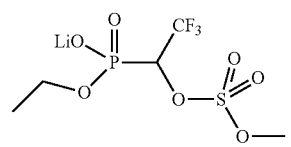 G10
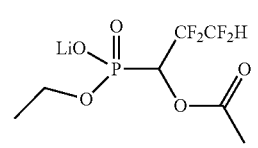 G11
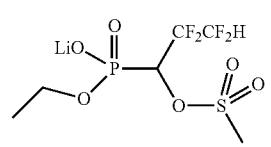 G12
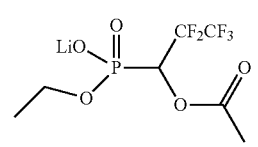 G13
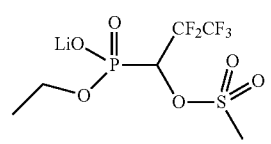 G14
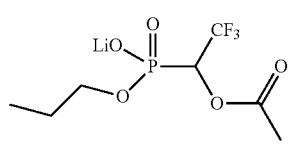 G15
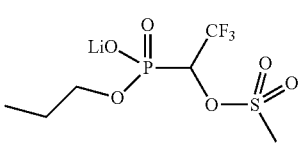 G16
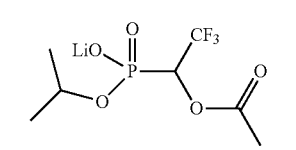 G17
-continued
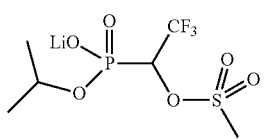 G18
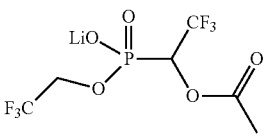 G19
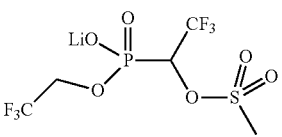 G20
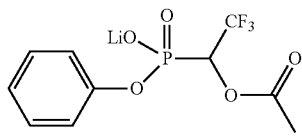 G21
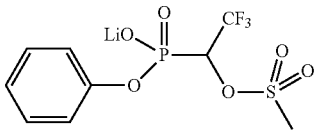 G22
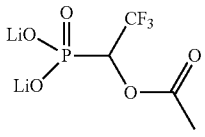 G23
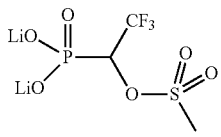 G24
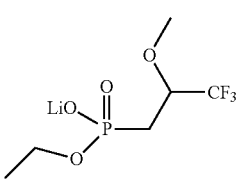 G25
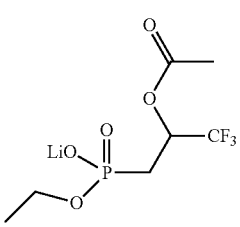 G26

G27
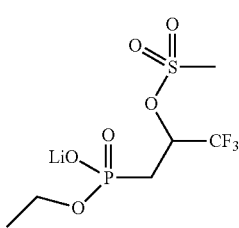

G28
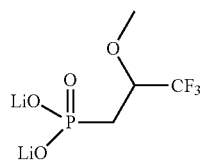

G29
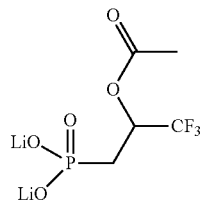

G30
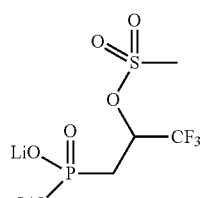

G31
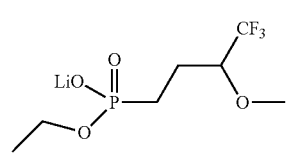

G32
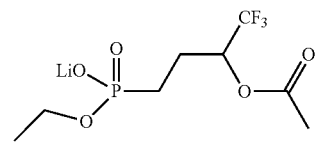

G33
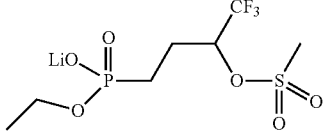

Among the aforementioned suitable examples, one or more selected from Compounds A5 to A9, A14 to A21, A24 to A31, A34 to A43, A46, A47, A52 to A54, A56, A57, B1 to B8, B10 to B12, B16 to B25, B28 to B35, B38 to B46, B49 to B64, B66, B67, B69, B70, B72 to B76, C1 to C22, C24 to C27, C30 to C33, C35, C36, D4 to D8, D14 to D18, D20, D21, D23, D24, D26, D27, D29, D30, D35, D36, D38 to D42, D44 to D48, E4 to E8, E14 to E24, E26, E27, E29, E30, E32, E33, F4 to F9, F14 to F18, F20, F21, F26, F27, F29 to F33, F35, F36, G1 to G16, and G19 to G24 are preferred; one or more selected from Compounds A6 to A8, A15 to A18, A20, A21, A24 to A31, A34 to A43, A47, B2 to B4, B7, B8, B10 to B12, B16 to B20, B22 to B25, B28 to B35, B39 to B41, B43 to B46, B49 to B56, B58 to B60, B63, B64, B66, B67, B69, B70, B72, B73, B75, B76, C1 to C3, C7 to C9, C11 to C13, C17 to C19, C21, C22, C24 to C27, C30 to C33, C35, C36, D5 to D7, D15 to D17, D20, D21, D23, D24, D26, D27, D29, D30, D35, D36, D38 to D42, E5 to E7, E15 to E17, E20, E21, E23, E24, F5 to F7, F9, F15 to F17, F20, F21, F26, F27, F29 to F33, F35, F36, F38, F39, G2 to G4, G7 to G9, G11 to G16, G19 to G24, G26, G27, G29, and G30 are more preferred; and one or more selected from lithium methyl (1-acetoxy-2-oxopropyl)phosphonate (Compound A6), lithium methyl (1-((methylsulfonyl)oxy)-2-oxopropyl)phosphonate (Compound A8), lithium ethyl (1-acetoxy-2-oxopropyl)phosphonate (Compound A15), lithium ethyl (1-((methylsulfonyl)oxy)-2-oxopropyl)phosphonate (Compound A18), lithium methyl (1-acetoxy-2-methoxy-2-oxoethyl)phosphonate (Compound B2), lithium methyl (1-((methylsulfonyl)oxy)-2-methoxy-2-oxoethyl)phosphonate (Compound B4), lithium ethyl (1-acetoxy-2-methoxy-2-oxoethyl)phosphonate (Compound B7), lithium ethyl (1-((methylsulfonyl)oxy)-2-methoxy-2-oxoethyl)phosphonate (Compound B17), lithium ethyl (1-acetoxy-2-ethoxy-2-oxoethyl)phosphonate (Compound B39), lithium ethyl (1-((methylsulfonyl)oxy)-2-ethoxy-2-oxoethyl)phosphonate (Compound B41), lithium ethyl (1-((methylsulfonyl)oxy)-2-(2,2,2-trifluoroethoxy)-2-oxoethyl)phosphonate (Compound B50), lithium methyl ((dimethoxyphosphoryl)methyl)phosphonate (Compound C1), lithium methyl (acetoxy(dimethoxyphosphoryl)methyl)phosphonate (Compound C7), lithium methyl ((dimethoxyphosphoryl)((methylsulfonyl)oxy)methylphosphonate (Compound C9), lithium ethyl ((diethoxyphosphoryl)methyl)phosphonate (Compound C11), lithium ethyl (acetoxy(diethoxyphosphoryl)methyl)phosphonate (Compound C17), lithium ethyl ((diethoxyphosphoryl)((methylsulfonyl)oxy)methyl)phosphonate (Compound C19), lithium methyl (2-dimethoxyphosphoryl)ethyl)phosphonate (Compound C32), lithium ethyl (2-(diethoxyphosphoryl)ethyl)phosphonate (Compound C33), lithium methyl (acetoxy(methylsulfonyl)methyl)phosphonate (Compound D5), lithium methyl ((methylsulfonyl)((methylsulfonyl)oxy)methyl)phosphonate (Compound D7), lithium ethyl (acetoxy(methylsulfonyl)methyl)phosphonate (Compound D15), lithium ethyl ((methylsulfonyl) ((methylsulfonyl)oxy)methyl)phosphonate (Compound D17), lithium methyl (acetoxy(methoxysulfonyl)methyl)phosphonate (Compound E5), lithium methyl ((methoxysulfonyl) ((methylsulfonyl)oxy)methyl) phosphonate (Compound E7), lithium ethyl (acetoxy (ethoxysulfonyl)methyl)phosphonate (Compound E15), lithium ethyl ((ethoxysulfonyl)((methylsulfonyl)oxy)methyl)phosphonate (Compound E17), lithium methyl (acetoxy (cyano)methyl)phosphonate (Compound F5), lithium methyl (cyano((methylsulfonyl)oxy)methyl)phosphonate (Compound F7), lithium ethyl cyanomethylphosphonate (Compound F9), lithium ethyl (acetoxy(cyano)methyl)phosphonate (Compound F15), lithium ethyl (cyano((methylsulfonyl)oxy)methyl)phosphonate (Compound F17), lithium methyl (1-acetoxy-2,2,2-trifluoroethyl)phosphonate (Compound G2), lithium methyl (2,2,2-trifluoro-1-((methylsulfonyl)oxy)ethyl)phosphonate (Compound G4), lithium ethyl (1-acetoxy-2,2,2-trifluoroethyl)phosphonate (Compound G7), and lithium ethyl (2,2,2-trifluoro-1-((methylsulfonyl)oxy)ethyl)phosphonate (Compound G9) are especially preferred.

In the nonaqueous electrolytic solution of the third invention, a content of the compound represented by the general formula (III), which is contained in the nonaqueous electrolytic solution, is preferably 0.001 to 10 mass % in the nonaqueous electrolytic solution. When the content is 10 mass % or less, there is less concern of occurrence of the matter that a surface film is excessively formed on an electrode, so that the low-temperature properties are worsened, whereas when it is 0.001 mass % or more, the formation of a surface film is sufficient, and an improving effect of the electrochemical characteristics in a broad temperature range is enhanced, and hence, the aforementioned range is preferred. The content is more preferably 0.05 mass % or more, and still more preferably 0.1 mass % or more in the nonaqueous electrolytic solution. An upper limit thereof is more preferably 5 mass % or less, and still more preferably 3 mass % or less.

In the nonaqueous electrolytic solution of the third invention, by combining the compound represented by the general formula (III) with a nonaqueous solvent, an electrolyte salt, and further other additives as mentioned later, a peculiar effect of synergistically improving the electrochemical characteristics in a broad temperature range is revealed.

[Nonaqueous Solvent]

As the nonaqueous solvent which is used for the nonaqueous electrolytic solution of the present invention, there are suitably exemplified one or more selected from cyclic carbonates, linear esters, lactones, ethers, and amides. In order that the electrochemical characteristics may be synergistically improved in a broad temperature range, it is preferred to include a linear ester, it is more preferred to include a linear carbonate, and it is most preferred to include both a cyclic carbonate and a linear carbonate.

The term "linear ester" is used as a concept including a linear carbonate and a linear carboxylic acid ester.

As the cyclic carbonate, there are exemplified one or more selected from ethylene carbonate (EC), propylene carbonate (PC), 1,2-butylene carbonate, 2,3-butylene carbonate, 4-fluoro-1,3-dioxolan-2-one (FEC), trans- or cis-4,5-difluoro-1,3-dioxolan-2-one (the both will be hereunder named generically as "DFEC"), vinylene carbonate (VC), vinyl ethylene carbonate (VEC), and 4-ethynyl-1,3-dioxolan-2-one (EEC). One or more selected from ethylene carbonate, propylene carbonate, 4-fluoro-1,3-dioxolan-2-one, vinylene carbonate, and 4-ethynyl-1,3-dioxolan-2-one (EEC) are more suitable.

Use of at least one of cyclic carbonates having an unsaturated bond, such as a carbon-carbon double bond, a carbon-carbon triple bond, etc., or a fluorine atom is preferred because the electrochemical characteristics are much more improved in a broad temperature range, and it is more preferred to contain both a cyclic carbonate having an unsaturated bond, such as a carbon-carbon double bond, a carbon-carbon triple bond, etc., and a cyclic carbonate having a fluorine atom. As the cyclic carbonate having an unsaturated bond, such as a carbon-carbon double bond, a carbon-carbon triple bond, etc., VC, VEC, or EEC is more preferred, and as the cyclic carbonate having a fluorine atom, FEC or DFEC is more preferred.

A content of the cyclic carbonate having an unsaturated bond, such as a carbon-carbon double bond, a carbon-carbon triple bond, etc., is preferably 0.07 volume % or more, more preferably 0.2 volume % or more, and still more preferably 0.7 volume % or more relative to a total volume of the nonaqueous solvent, and when an upper limit thereof is preferably 7 volume % or less, more preferably 4 volume % or less, and still more preferably 2.5 volume % or less, the electrochemical characteristics can be much more improved in a broad temperature range without impairing Li ion permeability, and hence, such is preferred.

A content of the cyclic carbonate having a fluorine atom is preferably 0.07 volume % or more, more preferably 4 volume % or more, and still more preferably 6 volume % or more relative to a total volume of the nonaqueous solvent, and when an upper limit thereof is preferably 35 volume % or less, more preferably 25 volume % or less, and still more preferably 15 volume % or less, the electrochemical characteristics can be much more improved in a broad temperature range without impairing Li ion permeability, and hence, such is preferred.

In the case where the nonaqueous solvent includes both the cyclic carbonate having an unsaturated bond, such as a carbon-carbon double bond, a carbon-carbon triple bond, etc., and the cyclic carbonate having a fluorine atom, the content of the cyclic carbonate having an unsaturated bond, such as a carbon-carbon double bond, a carbon-carbon triple bond, etc., is preferably 0.2 volume % or more, more preferably 3 volume % or more, and still more preferably 7 volume % or more relative to the content of the cyclic carbonate having a fluorine atom, and when an upper limit thereof is preferably 40 volume % or less, more preferably 30 volume % or less, and still more preferably 15 volume % or less, the electrochemical characteristics can be much more improved in a broad temperature range without impairing Li ion permeability, and hence, such is especially preferred.

When the nonaqueous solvent includes both ethylene carbonate and the cyclic carbonate having an unsaturated bond, such as a carbon-carbon double bond, a carbon-carbon triple bond, etc., the electrochemical characteristics of a surface film to be formed on an electrode in a broad temperature range is improved, and hence, such is preferred. A content of ethylene carbonate and the cyclic carbonate having an unsaturated bond, such as a carbon-carbon double bond, a carbon-carbon triple bond, etc., is preferably 3 volume % or more, more preferably 5 volume % or more, and still more preferably 7 volume % or more relative to a total volume of the nonaqueous solvent. An upper limit thereof is preferably 45 volume % or less, more preferably 35 volume % or less, and still more preferably 25 volume % or less.

These solvents may be used solely; in the case where a combination of two or more of the solvents is used, the electrochemical characteristics in a broad temperature range are more improved, and hence, such is preferred; and use of a combination of three or more thereof is especially preferred. As suitable combinations of these cyclic carbonates, EC and PC; EC and VC; PC and VC; VC and FEC; EC and FEC; PC and FEC; FEC and DFEC; EC and DFEC; PC and DFEC; VC and DFEC; VEC and DFEC; VC and EEC; EC and EEC; EC, PC and VC; EC, PC and FEC; EC, VC and FEC; EC, VC and VEC; EC, VC and EEC; EC, EEC and FEC; PC, VC and FEC; EC, VC and DFEC; PC, VC and DFEC; EC, PC, VC and FEC; EC, PC, VC and DFEC; and the like are preferred. Among the aforementioned combinations, combinations, such as EC and VC; EC and FEC; PC and FEC; EC, PC and VC; EC, PC and FEC; EC, VC and FEC; EC, VC and EEC; EC, EEC and FEC; PC, VC and FEC; EC, PC, VC and FEC; etc., are more preferred.

As the linear ester, there are suitably exemplified one or more asymmetric linear carbonates selected from methyl ethyl carbonate (MEC), methyl propyl carbonate (MPC), methyl isopropyl carbonate (MIPC), methyl butyl carbonate, and ethyl propyl carbonate; one or more symmetric linear carbonates selected from dimethyl carbonate (DMC), diethyl carbonate (DEC), dipropyl carbonate, and dibutyl carbonate; and one or more linear carboxylic acid esters selected from pivalate esters, such as methyl pivalate, ethyl pivalate, propyl pivalate, etc., methyl propionate, ethyl propionate, propyl propionate, methyl acetate, and ethyl acetate (EA).

Among the aforementioned linear esters, linear esters having a methyl group selected from dimethyl carbonate (DMC), methyl ethyl carbonate (MEC), methyl propyl carbonate (MPC), methyl isopropyl carbonate (MIPC), methyl butyl carbonate, methyl propionate, methyl acetate, and ethyl acetate (EA), are preferred, and linear carbonates having a methyl group are especially preferred.

In the case of using a linear carbonate, it is preferred to use two or more thereof. Furthermore, it is more preferred that both the symmetric linear carbonate and the asymmetric linear carbonate are included, and it is still more preferred that a content of the symmetric linear carbonate is more than a content of the asymmetric linear carbonate.

Although the content of the linear ester is not particularly limited, it is preferred to use the linear ester in an amount in the range of from 60 to 90 volume % relative to a total volume of the nonaqueous solvent. When the content is 60 volume % or more, the viscosity of the nonaqueous electrolytic solution does not become excessively high, and when it is 90 volume % or less, there is less concern of occurrence of the matter that an electroconductivity of the nonaqueous electrolytic solution is decreased, so that the electrochemical characteristics in a broad temperature range are worsened, and hence, the aforementioned range is preferred.

A proportion of the volume occupied by the symmetric linear carbonate in the linear carbonate is preferably 51 volume % or more, and more preferably 55 volume % or more. An upper limit thereof is preferably 95 volume % or less, and more preferably 85 volume % or less. It is especially preferred that dimethyl carbonate is included in the symmetric linear carbonate. It is more preferred that the asymmetric linear carbonate has a methyl group, and methyl ethyl carbonate is especially preferred. The aforementioned case is preferred because the electrochemical characteristics in a broad temperature range are much more improved.

As for a proportion of the cyclic carbonate and the linear ester, from the viewpoint of improving the electrochemical characteristics at a high temperature, a ratio of the cyclic carbonate to the linear ester (volume ratio) is preferably from 10/90 to 45/55, more preferably from 15/85 to 40/60, and especially preferably from 20/80 to 35/65.

As other nonaqueous solvents, there are suitably exemplified one or more selected from cyclic ethers, such as tetrahydrofuran, 2-methyltetrahydrofuran, 1,4-dioxane, etc.; linear ethers, such as 1,2-dimethoxyethane, 1,2-diethoxyethane, 1,2-butoxyethane, etc.; amides, such as dimethylformamide, etc.; sulfones, such as sulfolane, etc.; and lactones, such as γ-butyrolactone (GBL), γ-valerolactone, α-angelicalactone, etc.

The aforementioned other nonaqueous solvents are generally mixed and used for the purpose of achieving appropriate physical properties. As for a combination thereof, for example, there are suitably exemplified a combination of a cyclic carbonate, a linear ester, and a lactone, a combination of a cyclic carbonate, a linear ester, and an ether, and the like, and a combination of a cyclic carbonate, a linear ester, and a lactone is more preferred. Among the lactones, γ-butyrolactone (GBL) is still more preferably used.

The combination of a cyclic carbonate, a linear ester, and a lactone is preferred, and among the lactones, γ-butyrolactone (GBL) is more preferably used.

A content of other nonaqueous solvents is generally 1% or more, and preferably 2% or more, and generally 40% or less, preferably 30% or less, and more preferably 20% or less relative to a total volume of the nonaqueous solvent.

For the purpose of much more improving the electrochemical characteristics in a broad temperature range, it is preferred to further add other additives in the nonaqueous electrolytic solution.

As specific examples of other additives, there are exemplified compounds of the following (A) to (I).

(A) One or more nitriles selected from acetonitrile, propionitrile, succinonitrile, glutaronitrile, adiponitrile, pimelonitrile, suberonitrile, and sebaconitrile.

(B) Aromatic compounds having a branched alkyl group, such as cyclohexylbenzene, fluorocyclohexylbenzene compounds (e.g., 1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-butylbenzene, etc., and aromatic compounds, such as biphenyl, terphenyl (including o-, m-, and p-forms), diphenyl ether, fluorobenzene, difluorobenzene (including o-, m-, and p-forms), anisole, 2,4-difluoroanisole, a partial hydride of terphenyl (e.g., 1,2-dicyclohexylbenzene, 2-phenylbicyclohexyl, 1,2-diphenylcyclohexane, and o-cyclohexylbiphenyl), etc.

(C) One or more isocyanate compounds selected from methyl isocyanate, ethyl isocyanate, butyl isocyanate, phenyl isocyanate, tetramethylene diisocyanate, hexamethylene diisocyanate, octamethylene diisocyanate, 1,4-phenylene diisocyanate, 2-isocyanatoethyl acrylate, and 2-isocyanatoethyl methacrylate.

(D) One or more triple bond-containing compounds selected from 2-propynyl methyl carbonate, 2-propynyl acetate, 2-propynyl formate, 2-propynyl methacrylate, 2-propynyl methanesulfonate, 2-propynyl vinylsulfonate, 2-propynyl 2-(methanesulfonyloxy)propionate, di(2-propynyl) oxalate, methyl 2-propynyl oxalate, ethyl 2-propynyl oxalate, di(2-propynyl) glutarate, 2-butyne-1,4-diyl dimethanesulfonate, 2-butyne-1,4-diyl diformate, and 2,4-hexadiyne-1,6-diyl dimethanesulfonate.

(E) One or more cyclic or linear S=O group-containing compounds selected from sultones, such as 1,3-propanesultone, 1,3-butanesultone, 2,4-butanesultone, 1,4-butanesultone, 1,3-propenesultone, 2,2-dioxide-1,2-oxathiolane-4-yl acetate, 5,5-dimethyl-1,2-oxathiolane-4-one 2,2-dioxide, etc.; cyclic sulfites, such as ethylene sulfite, hexahydrobenzo[1,3,2]dioxathiolane-2-oxide (also called 1,2-cyclohexanediol cyclic sulfite), 5-vinyl-hexahydro-1,3,2-benzodioxathiol-2-oxide, 4-(methylsulfonylmethyl)-1,3,2-dioxathiolane-2-oxide, etc.; sulfonic acid esters, such as butane-2,3-diyl dimethanesulfonate, butane-1,4-diyl dimethanesulfonate, methylene methanedisulfonate, dimethyl methanedisulfonate, pentafluorophenyl methanesulfonate, etc.; and vinylsulfone compounds, such as divinylsulfone, 1,2-bis(vinylsulfonyl)ethane, bis(2-vinylsulfonylethyl) ether, etc.

(F) Cyclic acetal compounds, such as 1,3-dioxolane, 1,3-dioxane, 1,3,5-trioxane, etc.

(G) One or more phosphorus-containing compounds selected from trimethyl phosphate, tributyl phosphate, trioctyl phosphate, tris(2,2,2-trifluoroethyl)phosphate, bis(2,2,2-trifluoroethyl) methyl phosphate, bis(2,2,2-trifluoroethyl) ethyl phosphate, bis(2,2,2-trifluoroethyl) 2,2-difluoroethyl phosphate, bis(2,2,2-trifluoroethyl) 2,2,3,3-tetrafluoropropyl phosphate, bis(2,2-difluoroethyl) 2,2,2-trifluoroethyl phosphate, bis(2,2,3,3-tetrafluoropropyl) 2,2,2-trifluoroethyl phosphate, (2,2,2-trifluoroethyl) (2,2,3,3-tetrafluoropropyl)methyl phosphate, tris(1,1,1,3,3,3-hexafluoropropan-2-yl)phosphate, methyl methylenebisphosphonate, ethyl methylenebisphosphonate, methyl ethylenebisphosphonate, ethyl ethylenebisphosphonate, methyl butylenebisphosphonate, ethyl butylenebisphosphonate, methyl 2-(dimethylphosphoryl)acetate, ethyl 2-(dimethylphosphoryl)acetate, methyl 2-(diethylphosphoryl)acetate, ethyl 2-(diethylphosphoryl)acetate, 2-propynyl 2-(dimethylphosphoryl)acetate, 2-propynyl 2-(diethylphosphoryl)acetate, methyl 2-(dimethoxyphosphoryl)acetate, ethyl 2-(dimethoxyphosphoryl)acetate, methyl 2-(diethoxyphosphoryl)acetate, ethyl 2-(diethoxyphosphoryl)acetate, 2-propynyl 2-(dimethoxyphosphoryl)acetate, 2-propynyl 2-(diethoxyphosphoryl)acetate, methyl pyrophosphate, and ethyl pyrophosphate.

(H) Linear carboxylic acid anhydrides, such as acetic anhydride, propionic anhydride, etc., and cyclic acid anhydrides, such as succinic anhydride, maleic anhydride, 3-allylsuccinic anhydride, glutaric anhydride, itaconic anhydride, 3-sulfo-propionic anhydride, etc.

(I) Cyclic phosphazene compounds, such as methoxypentafluorocyclotriphosphazene, ethoxypentafluorocyclotriphosphazene, phenoxypentafluorocyclotriphosphazene, ethoxyheptafluorocyclotetraphosphazene, etc.

Of the foregoing, when at least one selected from the nitriles (A), the aromatic compounds (B), and the isocyanate compounds (C) is included, the electrochemical characteristics in a broad temperature range are much more improved, and hence, such is preferred.

Of the nitriles (A), one or more selected from succinonitrile, glutaronitrile, adiponitrile, and pimelonitrile are more preferred.

Of the aromatic compounds (B), one or more selected from biphenyl, terphenyl (including o-, m-, and p-forms), fluorobenzene, cyclohexylbenzene, tert-butylbenzene, and tert-amylbenzene are more preferred; and one or more selected from biphenyl, o-terphenyl, fluorobenzene, cyclohexylbenzene, and tert-amylbenzene are especially preferred.

Of the isocyanate compounds (C), one or more selected from hexamethylene diisocyanate, octamethylene diisocyanate, 2-isocyanatoethyl acrylate, and 2-isocyanatoethyl methacrylate are more preferred.

A content of each of the aforementioned additives (A) to (C) is preferably 0.01 to 7 mass % in the nonaqueous electrolytic solution. When the content falls within this range, a surface film is sufficiently formed without causing an excessive increase of the thickness, and the electrochemical characteristics in a broad temperature range are much more improved. The content is more preferably 0.05 mass % or more, and still more preferably 0.1 mass % or more in the nonaqueous electrolytic solution, and an upper limited thereof is more preferably 5 mass % or less, and still more preferably 3 mass % or less.

When the triple bond-containing compound (D), the cyclic or linear S=O group-containing compound (E) selected from sultones, cyclic sulfites, sulfonic acid esters, and vinylsulfones, the cyclic acetal compound (F), the phosphorus-containing compound (G), the cyclic acid anhydride (H), or the cyclic phosphazene compound (I) is included, the electrochemical characteristics in a broad temperature range are much more improved, and hence, such is preferred.

As the triple bond-containing compound (D), one or more selected from 2-propynyl methyl carbonate, 2-propynyl methacrylate, 2-propynyl methanesulfonate, 2-propynyl vinylsulfonate, 2-propynyl 2-(methanesulfonyloxy)propionate, di(2-propynyl) oxalate, methyl 2-propynyl oxalate, ethyl 2-propynyl oxalate, and 2-butyne-1,4-diyl dimethanesulfonate are preferred; and one or more selected from 2-propynyl methanesulfonate, 2-propynyl vinylsulfonate, 2-propynyl 2-(methanesulfonyloxy)propionate, di(2-propynyl) oxalate, and 2-butyne-1,4-diyl dimethanesulfonate are more preferred.

It is preferred to use the cyclic or linear S=O group-containing compound (E) selected from sultones, cyclic sulfites, sulfonic acid esters, and vinylsulfones (provided that triple bond-containing compounds and the specified lithium salt represented by any of the aforementioned general formulae are not included).

As the cyclic S=O group-containing compound, there are suitably exemplified one or more selected from sultones, such as 1,3-propanesultone, 1,3-butanesultone, 1,4-butanesultone, 2,4-butanesultone, 1,3-propenesultone, 2,2-dioxide-1,2-oxathiolane-4-yl acetate, 5,5-dimethyl-1,2-oxathiolane-4-one 2,2-dioxide, etc.; sulfonic acid esters, such as methylene methanedisulfonate, etc.; and cyclic sulfites, such as ethylene sulfite, 4-(methylsulfonylmethyl)-1,3,2-dioxathiolane 2-oxide, etc.

As the linear S=O group-containing compound, there are suitably exemplified one or more selected from butane-2,3-diyl dimethanesulfonate, butane-1,4-diyl dimethanesulfonate, dimethyl methanedisulfonate, pentafluorophenyl methanesulfonate, divinylsulfone, and bis(2-vinylsulfonylethyl) ether.

Of the aforementioned cyclic or linear S=O group-containing compounds, one or more selected from 1,3-propanesultone, 1,4-butanesultone, 2,4-butanesultone, 2,2-dioxide-1,2-oxathiolane-4-yl acetate, 5,5-dimethyl-1,2-oxathiolane-4-one 2,2-dioxide, butane-2,3-diyl dimethanesulfonate, pentafluorophenyl methanesulfonate, and divinylsulfone are more preferred.

As the cyclic acetal compound (F), 1,3-dioxolane and 1,3-dioxane are preferred, and 1,3-dioxane is more preferred.

As the phosphorus-containing compound (G), tris(2,2,2-trifluoroethyl) phosphate, tris(1,1,1,3,3,3-hexafluoropropan-2-yl) phosphate, methyl 2-(dimethylphosphoryl)acetate, ethyl 2-(dimethylphosphoryl)acetate, methyl 2-(diethylphosphoryl)acetate, ethyl 2-(diethylphosphoryl)acetate, 2-propynyl 2-(dimethylphosphoryl)acetate, 2-propynyl 2-(diethylphosphoryl)acetate, methyl 2-(dimethoxyphosphoryl)acetate, ethyl 2-(dimethoxyphosphoryl)acetate, methyl 2-(diethoxyphosphoryl)acetate, ethyl 2-(diethoxyphosphoryl)acetate, 2-propynyl 2-(dimethoxyphosphoryl)acetate, and 2-propynyl 2-(diethoxyphosphoryl)acetate are preferred; and tris(2,2,2-trifluoroethyl) phosphate, tris(1,1,1,3,3,3-hexafluoropropan-2-yl) phosphate, ethyl 2-(diethylphosphoryl)acetate, 2-propynyl 2-(dimethylphosphoryl)acetate, 2-propynyl 2-(diethylphosphoryl)acetate, ethyl 2-(diethoxyphosphoryl)acetate, 2-propynyl 2-(dimethoxyphosphoryl)acetate, and 2-propynyl 2-(diethoxyphosphoryl)acetate are more preferred.

As the cyclic acid anhydride (H), succinic anhydride, maleic anhydride, and 3-allylsuccinic anhydride are preferred, and succinic anhydride and 3-allylsuccinic anhydride are more preferred.

As the cyclic phosphazene compound (I), cyclic phosphazene compounds, such as methoxypentafluorocyclotriphosphazene, ethoxypentafluorocyclotriphosphazene, phenoxypentafluorocyclotriphosphazene, etc., are preferred, and methoxypentafluorocyclotriphosphazene and ethoxypentafluorocyclotriphosphazene are more preferred.

A content of each of the aforementioned additives (D) to (I) is preferably 0.001 to 5 mass % in the nonaqueous electrolytic solution. When the content falls within this range, a surface film is sufficiently formed without causing an excessive increase of the thickness, and the electrochemical characteristics in a broad temperature range are much more improved. The content is more preferably 0.01 mass % or more, and still more preferably 0.1 mass % or more in the nonaqueous electrolytic solution, and an upper limited thereof is more preferably 3 mass % or less, and still more preferably 2 mass % or less.

For the purpose of much more improving the electrochemical characteristics in abroad temperature range, it is preferred that at least one selected from lithium salts having an oxalate structure, lithium salts having a phosphate structure, and lithium salts having an S=O group is further included in the nonaqueous electrolytic solution.

As specific examples of the lithium salt, there are suitably exemplified at least one lithium salt having an oxalate structure, which is selected from lithium bis(oxalate)borate [LiBOB], lithium difluoro(oxalate)borate [LiDFOB], lithium tetrafluoro(oxalate)phosphate [LiTFOP], and lithium difluorobis(oxalate)phosphate [LiDFOP]; a lithium salt having a phosphate structure, such as $LiPO_2F_2$, $Li_2PO_3F$, etc.; and at least one lithium salt having an S=O group, which is selected from lithium trifluoro((methanesulfonyl)oxy)borate [LiTFMSB], lithium pentafluoro ((methanesulfonyl)oxy)phosphate [LiPFMSP], lithium methyl sulfate [LMS], lithium ethyl sulfate [LES], lithium 2,2,2-trifluoroethyl sulfate [LFES], and $FSO_3Li$.

Among those, it is more preferred that a lithium salt selected from LiBOB, LiDFOB, LiTFOP, LiDFOP, $LiPO_2F_2$, LiTFMSB, LMS, LES, LFES, and $FSO_3Li$ is included.

A total content of at least one selected from lithium salts having an oxalate structure, lithium salts having a phosphate structure, and lithium salts having an S=O group is preferably 0.001 to 10 mass % in the nonaqueous electrolytic solution. When the content is 10 mass % or less, there is less concern of occurrence of the matter that a surface film is excessively formed on an electrode, so that the storage characteristics are worsened, and when it is 0.001 mass % or more, the formation of a surface film is sufficient, and in the case of using a battery at a high temperature and at a high voltage, an improving effect of the characteristics is enhanced. The content is preferably 0.05 mass % or more, more preferably 0.1 mass % or more, and still more preferably 0.3 mass % or more in the nonaqueous electrolytic solution. An upper limit thereof is preferably 5 mass % or less, more preferably 3 mass % or less, and especially preferably 2 mass % or less.

(Electrolyte Salt)

As the electrolyte salt which is used in the present invention, there are suitably exemplified the following lithium salts.

As the lithium salt, there are suitably exemplified inorganic lithium salts, such as $LiPF_6$, $LiBF_4$, $LiClO_4$, etc.; linear fluoroalkyl group-containing lithium salts, such as $LiN(SO_2F)_2$ [LiFSI], $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3FT)_3$, $LiPF_5(iso-C_3FT)$, etc.; and cyclic fluoroalkylene chain-containing lithium salts, such as $(CF_2)_2(SO_2)_2NLi$, $(CF_2)_3(SO_2)_2NLi$, etc.; and the like. At least one lithium salt selected from these lithium salts is suitably exemplified, and one or more thereof may be used solely or in admixture.

Among those, one or more selected from $LiPF_6$, $LiBF_4$, $LiN(SO_2CF_3)_2$, $LiN(SO_2C_2F_5)_2$, and $LiN(SO_2F)_2$ [LiFSI] are preferred, and it is most preferred to use $LiPF_G$. In general, a concentration of the electrolyte salt is preferably 0.3 M or more, more preferably 0.7 M or more, and still more preferably 1.1 M or more relative to the nonaqueous solvent. An upper limit thereof is preferably 2.5 M or less, more preferably 2.0 M or less, and still more preferably 1.6 M or less.

As for a suitable combination of these electrolyte salts, the case of including $LiPF_6$ and further including at least one lithium salt selected from $LiBF_4$, $LiN(SO_2CF_3)_2$, and $LiN(SO_2F)_2$ [LiFSI] in the nonaqueous electrolytic solution is preferred. When a proportion of the lithium salt other than $LiPF_6$ occupying in the nonaqueous solvent is 0.001 M or more, an improving effect of the electrochemical characteristics in a broad temperature range is liable to be exhibited, and when it is 1.0 M or less, there is less concern of occurrence of the matter that the improving effect of the electrochemical characteristics in a broad temperature range is worsened, and hence, such is preferred. The proportion is preferably 0.01 M or more, especially preferably 0.03 M or more, and most preferably 0.04 M or more. An upper limit thereof is preferably 0.8 M or less, more preferably 0.6 M or less, still more preferably 0.4 M or less, and especially preferably 0.2 M or less.

[Production of Nonaqueous Electrolytic Solution]

The nonaqueous electrolytic solution of the present invention may be obtained, for example, by mixing the aforementioned nonaqueous solvent, adding the aforementioned electrolyte salt thereto, and further adding the compound represented by the general formula (X), (I), (II), or (III), in which the specified polar group is bound to the phosphorus atom, to the resulting nonaqueous electrolytic solution.

At this time, the nonaqueous solvent to be used and the compounds to be added to the nonaqueous electrolytic solution are preferably purified in advance to decrease impurities as far as possible within the range where the productivity is not remarkably worsened.

The nonaqueous electrolytic solution of the present invention may be used in first to fourth energy storage devices shown below, in which the nonaqueous electrolytic solution may be used as the nonaqueous electrolyte not only in the form of a liquid but also in the form of gel. Furthermore, the nonaqueous electrolytic solution of the present invention may also be used for a solid polymer electrolyte. Above all, the nonaqueous electrolytic solution is preferably used in the first energy storage device using a lithium salt as the electrolyte salt (namely, for a lithium battery) or in the fourth energy storage device (namely, for a lithium ion capacitor), more preferably used in a lithium battery, and still more preferably used in a lithium secondary battery.

[First Storage Device (Lithium Battery)]

The lithium battery as referred to in the present specification is a generic name for a lithium primary battery and a lithium secondary battery. In the present specification, the term "lithium secondary battery" is used as a concept also including a so-called lithium ion secondary battery. The lithium battery of the present invention includes a positive electrode, a negative electrode, and the aforementioned nonaqueous electrolytic solution having an electrolyte salt dissolved in a nonaqueous solvent. Other constitutional members than the nonaqueous electrolytic solution, such as the positive electrode, the negative electrode, etc., may be used without being particularly limited.

For example, examples of a positive electrode active material used for a lithium secondary battery include a complex metal oxide containing lithium and one or more selected from cobalt, manganese, and nickel. These positive electrode active materials may be used solely or in combination of two or more thereof.

Examples of the lithium complex metal oxide include one or more selected from $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$, and $LiCo_{0.98}Mg_{0.02}O_2$. These materials may be used as a combination, such as a combination of $LiCoO_2$ and $LiMn_2O_4$, a combination of $LiCoO_2$ and $LiNiO_2$, and a combination of $LiMn_2O_4$ and $LiNiO_2$.

For improving the safety on overcharging and the cycle characteristics, and for enabling the use at a charge potential of 4.3 V or more, a part of the lithium complex metal oxide may be substituted with other elements. For example, a part of cobalt, manganese, or nickel may be substituted with at least one element selected from Sn, Mg, Fe, Ti, Al, Zr, Cr, V, Ga, Zn, Cu, Bi, Mo, La, and the like, a part of O may be substituted with S or F, or the oxide may be coated with a compound containing any of such other elements.

Among those, a lithium complex metal oxide capable of being used at a charge potential of the positive electrode in a fully-charged state of 4.3 V or more based on Li, such as $LiCoO_2$, $LiMn_2O_4$, and $LiNiO_2$, is preferred; and a lithium complex metal oxide capable of being used at 4.4 V or more, such as $LiCo_{1-x}M_xO_2$ (wherein M represents one or more elements selected from Sn, Mg, Fe, Ti, Al, Zr, Cr, V, Ga, Zn, and Cu, and 0.001≤x≤0.05), $LiCo_{1/3}Ni_{1/3}Mn_{1/3}O_2$, $LiNi_{1/2}Mn_{3/2}O_4$, and a solid solution of $Li_2MnO_3$ and $LiMO_2$ (wherein M represents a transition metal, such as Co, Ni, Mn, Fe, etc.), is more preferred. The use of the lithium complex metal oxide capable of acting at a higher charged voltage is liable to worsen the electrochemical characteristics particularly in a broad temperature range due to the reaction with the electrolytic solution on charging, but in the lithium secondary battery according to the present invention, worsening of the electrochemical characteristics can be inhibited.

In particular, a battery with a positive electrode containing Mn tends to have an increased resistance of the battery due to elution of Mn ions from the positive electrode, thereby providing the tendency of worsening the electrochemical characteristics in a broad temperature range. However, the lithium secondary battery according to the present invention is preferred because worsening of the electrochemical characteristics can be inhibited.

Furthermore, a lithium-containing olivine-type phosphate may also be used as the positive electrode active material. In particular, a lithium-containing olivine-type phosphate including one or more selected from iron, cobalt, nickel, and manganese is preferred. As specific examples thereof, there are exemplified one or more selected from $LiFePO_4$, $LiCoPO_4$, $LiNiPO_4$, and $LiMnPO_4$.

A part of such a lithium-containing olivine-type phosphate may be substituted with other element. A part of iron, cobalt, nickel, or manganese may be substituted with one or more elements selected from Co, Mn, Ni, Mg, Al, B, Ti, V, Nb, Cu, Zn, Mo, Ca, Sr, W, and Zr, or the phosphate may be coated with a compound containing any of these other elements or with a carbon material. Among those, $LiFePO_4$ and $LiMnPO_4$ are preferred.

The lithium-containing olivine-type phosphate may also be used, for example, in admixture with the aforementioned positive electrode active material.

Examples of the positive electrode for a lithium primary battery include oxides or chalcogen compounds of one or more metal elements, such as $CuO$, $Cu_2O$, $Ag_2O$, $Ag_2CrO_4$, $CuS$, $CuSO_4$, $TiO_2$, $TiS_2$, $SiO_2$, $SnO$, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, $FeO$, $Fe_3O_4$, $Ni_2O_3$, $NiO$, $CoO_3$, $CoO$, and the like; a sulfur compound, such as $SO_2$, $SOCl_2$, etc.; and a carbon fluorides (graphite fluoride) represented by a general formula $(CF_x)_n$. Among those, $MnO_2$, $V_2O_5$, graphite fluoride, and the like are preferred.

In the case where when 10 g of the aforementioned positive electrode active material is dispersed in 100 mL of distilled water, a pH of a supernatant thereof is 10.0 to 12.5, the improving effect of the electrochemical characteristics in a much broader temperature range is liable to be obtained, and hence, such is preferred. The case where the pH is 10.5 to 12.0 is more preferred.

In the case where Ni is included as an element in the positive electrode, the content of impurities, such as LiOH, etc., in the positive electrode active material tends to increase, and the improving effect of the electrochemical characteristics in a much broader temperature range is liable to be obtained, and hence, such is preferred. The case where an atomic concentration of Ni in the positive electrode active material is 5 to 25 atomic % is more preferred, and the case where the atomic concentration of Ni is 8 to 21 atomic % is especially preferred.

An electroconductive agent of the positive electrode is not particularly limited so long as it is an electron-conductive material that does not undergo chemical change. Examples thereof include graphite, such as natural graphite (e.g., flaky graphite, etc.), artificial graphite, etc.; one or more carbon blacks selected from acetylene black, Ketjen black, channel black, furnace black, lamp black, and thermal black; and the like. The graphite and the carbon black may be appropriately mixed and used. An amount of the electroconductive agent added to a positive electrode mixture is preferably from 1 to 10 mass %, and especially preferably from 2 to 5 mass %.

The positive electrode can be produced in such a manner that the positive electrode active material is mixed with an electroconductive agent, such as acetylene black, carbon black, etc., and a binder, such as polytetrafluoroethylene (PTFE), polyvinylidene fluoride (PVDF), a copolymer of styrene and butadiene (SBR), a copolymer of acrylonitrile and butadiene (NBR), carboxymethyl cellulose (CMC), an ethylene-propylene-diene terpolymer, etc., to which is then added a high-boiling point solvent, such as 1-methyl-2-pyrrolidone, etc., followed by kneading to provide a positive electrode mixture, and the positive electrode mixture is applied onto a collector, such as an aluminum foil, a stainless steel-made lath plate, etc., dried, shaped under pressure, and then heat-treated in vacuum at a temperature of about 50° C. to 250° C. for about 2 hours.

A density of the positive electrode except for the collector is generally 1.5 $g/cm^3$ or more, and for the purpose of further increasing a capacity of the battery, the density is preferably 2 $g/cm^3$ or more, more preferably 3 $g/cm^3$ or more, and still more preferably 3.6 $g/cm^3$ or more. An upper limit thereof is preferably 4 $g/cm^3$ or less.

As a negative electrode active material for a lithium secondary battery, one or more selected from metal lithium, a lithium alloy, a carbon material capable of absorbing and releasing lithium [e.g., graphitizable carbon, non-graphitizable carbon having a spacing of a (002) plane of 0.37 nm or more, graphite having a spacing of the (002) plane of 0.34 nm or less, etc.], tin (elemental substance), a tin compound, silicon (elemental substance), a silicon compound, and a lithium titanate compound, such as $Li_4Ti_5O_{12}$, etc., may be used.

Among the aforementioned negative electrode active materials, in the ability of absorbing and releasing lithium ions, the use of a high-crystalline carbon material, such as artificial graphite, natural graphite, etc., is more preferred, and the use of a carbon material having a graphite-type crystal structure in which a lattice (002) spacing ($d_{002}$) is 0.340 nm (nanometers) or less, and especially from 0.335 to 0.337 nm, is still more preferred.

In particular, the use of artificial graphite particles having a bulky structure containing plural flattened graphite fine particles that are aggregated or bonded non-parallel to each other, or graphite particles produced through a spheroidizing treatment of flaky natural graphite particles by repeatedly applying a mechanical action, such as a compression force, a friction force, a shear force, etc., is preferred.

When a ratio I(110)/I(004) of a peak intensity I(110) of the (110) plane to a peak intensity I(004) of the (004) plane of the graphite crystal obtained through X-ray diffractometry of a negative electrode sheet that is shaped under pressure to such an extent that a density of the negative electrode except for the collector is 1.5 g/cm$^3$ or more, is 0.01 or more, the electrochemical characteristics are improved in a much broader temperature range, and hence, such is preferred. The ratio I(110)/I(004) is more preferably 0.05 or more, and still more preferably 0.1 or more. An upper limit of the ratio I(110)/I(004) of the peak intensity is preferably 0.5 or less, and more preferably 0.3 or less because there may be the case where the crystallinity is worsened to lower the discharge capacity of the battery due to an excessive treatment.

When the high-crystalline carbon material (core material) is coated with a carbon material having lower crystallinity than the core material, the electrochemical characteristics in a broad temperature range become much more favorable, and hence, such is preferred. The crystallinity of the carbon material in the coating may be confirmed through TEM.

When the high-crystalline carbon material is used, there is a tendency that it reacts with the nonaqueous electrolytic solution on charging, thereby worsening the electrochemical characteristics at a low temperature or a high temperature due to an increase of interfacial resistance. However, in the lithium secondary battery according to the present invention, the electrochemical characteristics in a broad temperature range become favorable.

As the metal compound capable of absorbing and releasing lithium as a negative electrode active material, there are suitably exemplified compounds containing at least one metal element, such as Si, Ge, Sn, Pb, P, Sb, Bi, Al, Ga, In, Ti, Mn, Fe, Co, Ni, Cu, Zn, Ag, Mg, Sr, Ba, etc. The metal compound may be in any form including an elemental substance, an alloy, an oxide, a nitride, a sulfide, a boride, an alloy with lithium, and the like, and any of an elemental substance, an alloy, an oxide, and an alloy with lithium is preferred because the battery capacity can be increased. Above all, compounds containing at least one element selected from Si, Ge, and Sn are preferred, and compounds containing at least one element selected from Si and Sn are more preferred because the battery capacity can be increased.

The negative electrode can be produced in such a manner that the same electroconductive agent, binder, and high-boiling point solvent as in the production of the positive electrode as described above are used and kneaded to provide a negative electrode mixture, and the negative electrode mixture is then applied on a collector, such as a copper foil, etc., dried, shaped under pressure, and then heat-treated in vacuum at a temperature of about from 50° C. to 250° C. for about 2 hours.

A density of the negative electrode except for the collector is generally 1.1 g/cm$^3$ or more, and for the purpose of further increasing a capacity of the battery, the density is preferably 1.5 g/cm$^3$ or more, and more preferably 1.7 g/cm$^3$ or more. An upper limit thereof is preferably 2 g/cm$^3$ or less.

Examples of the negative electrode active material for a lithium primary battery include metal lithium and a lithium alloy.

The structure of the lithium battery is not particularly limited, and may be a coin-type battery, a cylinder-type battery, a prismatic battery, a laminate-type battery, or the like, each having a single-layered or multi-layered separator.

The separator for the battery is not particularly limited, and a single-layered or laminated micro-porous film of a polyolefin, such as polypropylene, polyethylene, etc., a woven fabric, a nonwoven fabric, and the like may be used.

The lithium secondary battery in the present invention has excellent electrochemical characteristics in a broad temperature range even when a final charging voltage is 4.2 V or more, particularly 4.3 V or more, and furthermore, the characteristics are favorable even at 4.4 V or more. A final discharging voltage may be generally 2.8 V or more, and further 2.5 V or more, and the final discharging voltage of the lithium secondary battery in the present invention may be 2.0 V or more. An electric current is not particularly limited, and in general, the battery may be used within a range of from 0.1 to 30 C. The lithium battery in the present invention may be charged and discharged at from −40 to 100° C., and preferably from −10 to 80° C.

In the present invention, as a countermeasure against the increase in the internal pressure of the lithium battery, there may also be adopted such a method that a safety valve is provided in a battery cap, or a cutout is provided in a component, such as a battery can, a gasket, etc. As a safety countermeasure for prevention of overcharging, a circuit cut-off mechanism capable of detecting the internal pressure of the battery to cut off the current may be provided in the battery cap.

[Second Energy Storage Device (Electric Double Layer Capacitor)]

The second energy storage device of the present invention is an energy storage device including the nonaqueous electrolytic solution of the present invention and storing energy by utilizing an electric double layer capacitance in an interface between the electrolytic solution and the electrode. One example of the present invention is an electric double layer capacitor. A most typical electrode active material which is used in this energy storage device is active carbon. The double layer capacitance increases substantially in proportion to a surface area.

[Third Energy Storage Device]

The third energy storage device of the present invention is an energy storage device including the nonaqueous electrolytic solution of the present invention and storing energy by utilizing a doping/dedoping reaction of the electrode. Examples of the electrode active material which is used in this energy storage device include a metal oxide, such as ruthenium oxide, iridium oxide, tungsten oxide, molybdenum oxide, copper oxide, etc., and a π-conjugated polymer, such as polyacene, a polythiophene derivative, etc. A capacitor using such an electrode active material is capable of storing energy following the doping/dedoping reaction of the electrode.

[Fourth Energy Storage Device (Lithium Ion Capacitor)]

The fourth energy storage device of the present invention is an energy storage device including the nonaqueous electrolytic solution of the present invention and storing energy by utilizing intercalation of lithium ions into a carbon material, such as graphite, etc., as the negative electrode. This energy storage device is called a lithium ion capacitor (LIC). Examples of the positive electrode include one utilizing an electric double layer between an active carbon electrode and an electrolytic solution, one utilizing a doping/dedoping reaction of a π-conjugated polymer electrode, and the like. The electrolytic solution contains at least a lithium salt, such as $LiPF_6$, etc.

In the aforementioned constitutional examples of the energy storage device, an example in which the compound represented by the general formula (X), (I), (II), or (III) is contained in the electrolytic solution has been described. But, the aforementioned lithium phosphate may be contained in other constitutional elements of the energy storage device than the electrolytic solution.

In the following second embodiment to fourth embodiment, examples of the energy storage device in which the compound represented by the general formula (X), (I), (II), or (III) (hereinafter also referred to as "general formula (X), etc."), in which the specified polar group is bound directly to the phosphorus atom, is contained in advance in a constitutional element than the electrolytic solution, are described.

Second Embodiment: Example in which the Compound Represented by the General Formula (X), Etc. is Added to the Positive Electrode The positive electrode having the compound represented by the general formula (X), etc. added thereto can be produced in such a manner that the compound represented by the general formula (X), etc., in which the specified polar group is bound to the phosphorus atom, is mixed with the aforementioned positive electrode active material, electroconductive agent, and binder, to which is then added a high-boiling point solvent, such as 1-methyl-2-pyrrolidone, etc., followed by kneading to provide a positive electrode mixture, and the positive electrode mixture is applied onto a collector, such as an aluminum foil, a stainless steel-made lath plate, etc., dried, shaped under pressure, and then heat-treated in vacuum at a temperature of about 50° C. to 250° C. for about 2 hours.

An addition amount of the compound represented by the general formula (X), etc. is preferably 0.001 to 10 mass % relative to the positive electrode active material. The addition amount is more preferably 0.05 mass % or more, and still more preferably 0.1 mass % or more relative to the positive electrode active material. An upper limit thereof is more preferably 8 mass % or less, and still more preferably 5 mass % or less.

Third Embodiment: Example in which the Compound Represented by the General Formula (X), Etc. is Added to the Negative Electrode The negative electrode having the compound represented by the general formula (X), etc. added thereto can be produced in such a manner that the compound represented by the general formula (X), etc., in which the specified polar group is bound to the phosphorus atom, is kneaded with the same electroconductive agent, binder, and high-boiling point solvent as in the aforementioned production of the positive electrode, to provide a negative electrode mixture, and the negative electrode mixture is applied onto a collector, such as a copper foil, etc., dried, shaped under pressure, and then heat-treated in vacuum at a temperature of about 50° C. to 250° C. for about 2 hours.

An addition amount of the compound represented by the general formula (X), etc. is preferably 0.001 to 10 mass % relative to the negative electrode active material. The addition amount is more preferably 0.05 mass % or more, and still more preferably 0.1 mass % or more relative to the negative electrode active material. An upper limit thereof is more preferably 8 mass % or less, and still more preferably 5 mass % or less.

Fourth Embodiment: Example in which the Compound Represented by the General Formula (X), Etc. is Added to the Separator The separator containing the compound represented by the general formula (X), etc. on a surface or within pores thereof can be produced by a method in which the separator is dipped in and impregnated with a solution having the compound represented by the general formula (X), etc., in which the specified polar group is bound to the phosphorus atom, dissolved in an organic solvent or water, followed by drying. The separator containing the compound represented by the general formula (X), etc. can also be produced by preparing a coating liquid having the compound represented by the general formula (X), etc. dispersed in an organic solvent or water and applying the coating liquid on the entire surface of the separator.

[Novel Compound]

The compound of the present invention as a novel compound is hereunder described.

When the novel compound of the present invention is added to an energy storage device, the electrochemical characteristics of the energy storage device can be improved in a broad temperature range.

Although the novel compound of the present invention is especially useful as an additive for an energy storage device, in view of its special structure, it is useful as materials for an electrolyte application, a heat resistance application, etc. in the fields of general chemistry, particularly organic chemistry, electrochemistry, biochemistry, and polymer chemistry, and also useful as intermediate raw materials of drugs, agricultural chemicals, electronic materials, polymer materials, and the like.

<Novel Compound Related to First Invention>

The novel compound related to the first invention is a lithium phosphate represented by any of the following general formulae (I-V) to (I-VII), in which a polar group is bound directly to a phosphorus atom (P). Such a lithium phosphate is particularly useful as an additive for an energy storage device.

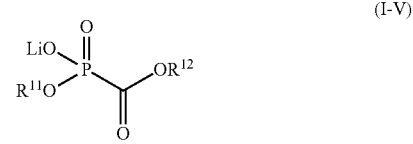

(I-V)

In the formula, $R^{11}$ and $R^{12}$ are each independently synonymous with $R^{20}$, provided that at least one of $R^{11}$ and $R^{12}$ is an alkynyl group having 3 to 6 carbon atoms.

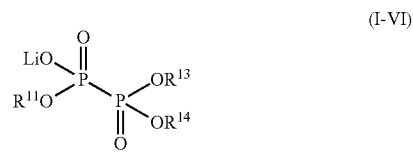

(I-VI)

In the formula, $R^{11}$, $R^{13}$, and $R^{14}$ are each independently synonymous with $R^{20}$, provided that the case where all of $R^{11}$, $R^{13}$, and $R^{14}$ are a lithium atom is excluded.

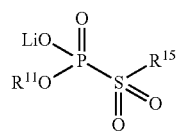

(I-VII)

In the formula, $R^{11}$ and $R^{15}$ are each independently synonymous with $R^{20}$.

The lithium phosphate represented by each of the general formulae (I-V) to (I-VII), which is related to the first invention, may be synthesized by a method of allowing a phosphate ester as a precursor to react with a lithium salt in the presence of a solvent, but the present invention is not limited to such a method at all.

The phosphate ester serving as a precursor may be synthesized by a known method. For example, methods described in *Journal of the American Chemical Society*, 2006, vol. 128, #15, p. 5251-5261, *Angewandte Chemie—International Edition*, 2010, vol. 49, #38, p. 6852-6855, German Patent No. 956404, and the like may be applied.

As the aforementioned lithium salt, there are suitably exemplified lithium carboxylates, such as lithium acetate, lithium formate, lithium propionate, lithium trifluoroacetate, lithium oxalate, lithium benzoate, etc., halogenated alkali metal salts, such as lithium fluoride, lithium chloride, lithium bromide, lithium iodide, etc., lithium carbonate, lithium hydroxide, and the like, but the present invention is not limited thereto at all.

Among the aforementioned lithium salts, lithium acetate, lithium chloride, lithium iodide, lithium carbonate, and lithium hydroxide are preferred, and lithium acetate and lithium chloride are more preferred.

An amount of the lithium salt used is preferably 0.5 mol or more, more preferably 0.7 mol or more, and still more preferably 0.9 mol or more per mol of the phosphate ester. This is because when the amount of the lithium salt used is less than 0.5 mol, the reaction does not thoroughly proceed, so that the yield is worsened. An upper limit thereof is preferably 2 mol or less, more preferably 1.5 mol or less, and still more preferably 1.1 mol or less. This is because when the amount of the lithium salt used is more than 2 mol, a side-reaction is liable to proceed, so that the yield is worsened, and impurities increase.

As the solvent which is used for the reaction, there are suitably exemplified water, an alcohol, a nitrile, a ketone, a sulfone, an amide, an ether, an ester, an aromatic compound, and a halogenated hydrocarbon. Among those, an alcohol, a ketone, and an ether are preferred.

As the solvent, specifically, there are suitably exemplified the following.

There are suitably exemplified water; an alcohol, such as methanol, ethanol, n-propanol, etc.; a nitrile, such as acetonitrile, propionitrile, etc.; a ketone, such as acetone, methyl ethyl ketone, methyl isobutyl ketone, etc.; a sulfone, such as dimethyl sulfoxide, etc.; an amide, such as N,N-dimethylformamide, N,N-dimethylacetamide, etc.; an ether, such as diethyl ether, tetrahydrofuran, etc.; an ester, such as ethyl acetate, ethyl propionate, dimethyl carbonate, diethyl carbonate, ethylmethyl carbonate, etc.; an aromatic compound, such as toluene, xylene, etc.; and a halogenated hydrocarbon, such as dichloromethane, 1,2-dichloroethane, o-dichlorobenzene, etc. However, the solvent is not limited thereto at all so long as it is a solvent not impairing the reaction.

Among those, an alcohol, such as methanol, ethanol, etc., a ketone, such as acetone, methyl ethyl ketone, methyl isobutyl ketone, etc., and an ether, such as diethyl ether, tetrahydrofuran, etc., are preferred, and acetone, methyl ethyl ketone, diethyl ether, and tetrahydrofuran are more preferred.

A lower limit of an amount of the solvent used is preferably 0.5 parts by mass or more, and more preferably 1 part by mass or more relative to 1 part by mass of the phosphate ester. An upper limit of the amount of the solvent used is preferably 50 parts by mass or less, and more preferably 20 parts by mass or less relative to 1 part by mass of the phosphate ester.

An upper limit of a reaction temperature is preferably 80° C. or lower, more preferably 70° C. or lower, and especially preferably 60° C. or lower. This is because in the case where the reaction temperature is higher than 80° C., a side-reaction is liable to proceed. A lower limit of the reaction temperature is preferably 0° C. or higher, more preferably 5° C. or higher, and especially preferably 10° C. or higher. This is because in the case where the reaction temperature is lower than 0° C., a reaction rate is largely decreased. However, in the case where a boiling point of the solvent used is 80° C. or lower, the boiling point of the solvent is set as the upper limit of the reaction temperature, whereas in the case where a melting point of the solvent used is 0° C. or higher, the melting point of the organic solvent is set as the lower limit of the reaction temperature.

Although a reaction time varies according to the reaction temperature or the amounts of the lithium salt and solvent used, a lower limit thereof is preferably 0.5 hours or more, and more preferably 1 hour or more. This is because when the reaction time is less than 0.5 hours, the reaction does not thoroughly proceed. Meanwhile, an upper limit thereof is preferably 24 hours or less, and more preferably 16 hours or less. This is because when the reaction time is more than 24 hours, a side-reaction is liable to proceed.

<Novel Compound Related to Second Invention>

The novel compound related to the second invention is a lithium phosphonate represented by any of the following general formulae (IV-I) to (IV-VI), in which a cyclic polar group is bound directly to a phosphorus atom (P). Such a lithium phosphonate is particularly useful as an additive for an energy storage device.

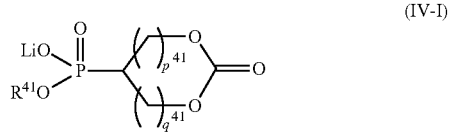

(IV-I)

In the formula, $R^{41}$ is synonymous with $R^{20}$; and $p^{41}$ and $q^{41}$ each independently represent an integer of 0 to 2 and satisfy a relation: $1 \leq (p^{41}+q^{41}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (IV-VII).

(IV-II)

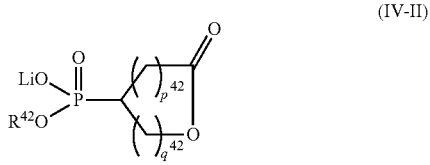

In the formula, $R^{42}$ is synonymous with $R^{20}$; and $p^{42}$ and $q^{42}$ each independently represent an integer of 0 to 3 and satisfy a relation: $1 \le (p^{42}+q^{42}) \le 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (IV-VII).

(IV-III)

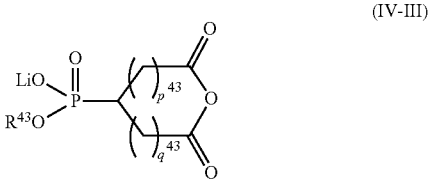

In the formula, $R^{43}$ is synonymous with $R^{20}$; and $p^{43}$ and $q^{43}$ each independently represent an integer of 0 to 2 and satisfy a relation: $1 \le (p^{43}+q^{43}) \le 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (IV-VII).

(IV-IV)

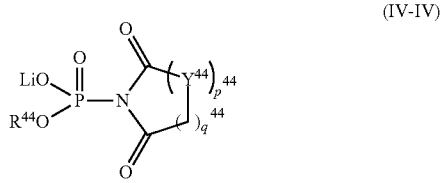

In the formula, $R^{44}$ is synonymous with $R^{20}$; $Y^{44}$ represents an —NH— group or an —O— group; $p^{44}$ represents an integer of 0 to 1; $q^{44}$ represents an integer of 1 to 4; and $p^{44}$ and $q^{44}$ satisfy a relation: $2 \le (p^{44}+q^{44}) \le 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (IV-VII).

(IV-V)

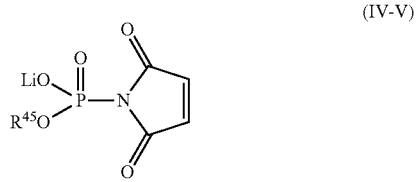

In the formula, $R^{45}$ is synonymous with $R^{20}$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (IV-VII).

(IV-VI)

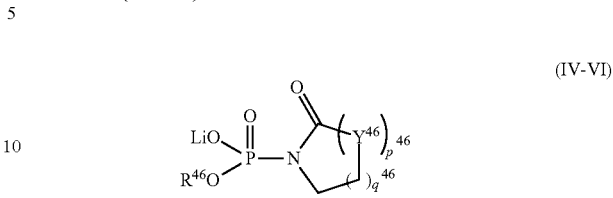

In the formula, $R^{46}$ is synonymous with $R^{20}$; $Y^{46}$ represents an —NH— group or an —O— group; $p^{46}$ represents an integer of 0 to 1; $q^{46}$ represents an integer of 1 to 4; and $p^{46}$ and $q^{46}$ satisfy a relation: $2 \le (p^{46}+q^{46}) \le 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (IV-VII).

(IV-VII)

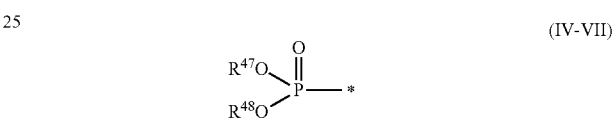

In the formula, $R^{47}$ and $R^{48}$ are each independently synonymous with $R^{20}$; and * represents a site binding to the cyclic polar group.

<Novel Compound Related to Third Invention>

The novel compound related to the third invention is a compound represented by any of the following general formulae (III-1) to (III-7), in which a polar group is bound directly to a phosphorus atom (P). Such a compound is particularly useful as an additive for an energy storage device.

(III-1)

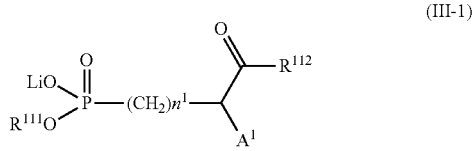

In the formula, $A^1$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{113}$ group, an —OC(=O)—OR$^{114}$ group, an —S(=O)$_2 R^{115}$ group, or an —S(=O)$_2$OR$^{116}$ group; $R^{111}$, $R^{114}$, and $R^{116}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; $R^{112}$, $R^{113}$, and $R^{115}$ each represent an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atoms; and $n^1$ represents an integer of 0 to 2.

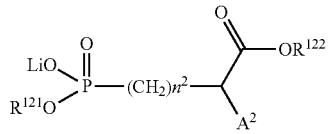

(III-2)

In the formula, $A^2$ represents an alkoxy group having 1 to 8 carbon atoms, in which a part of hydrogen atoms may be substituted with a halogen atom, an —OC(=O)$R^{123}$ group, an —OC(=O)—O$R^{124}$ group, an —S(=O)$_2R^{125}$ group, or an —S(=O)$_2$O$R^{126}$ group; $R^{121}$, $R^{122}$, $R^{124}$, and $R^{126}$ are each independently synonymous with $R^{20}$; $R^{123}$ and $R^{125}$ are each independently synonymous with $R^{113}$ and $R^{115}$, respectively; and $n^2$ represents an integer of 0 to 2.

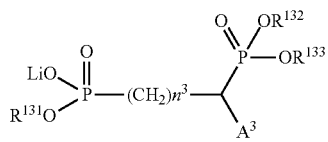

(III-3)

In the formula, $A^3$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{134}$ group, an —OC(=O)—O$R^{135}$ group, an —S(=O)$_2R^{136}$ group, or an —S(=O)$_2$O$R^{137}$ group; $R^{131}$, $R^{132}$, $R^{133}$, $R^{135}$, and $R^{137}$ are each independently synonymous with $R^{20}$; $R^{134}$ and $R^{136}$ are each independently synonymous with $R^{113}$ and $R^{115}$, respectively; and $n^3$ represents an integer of 0 to 2.

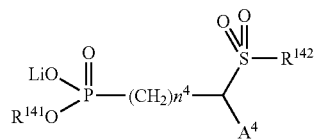

(III-4)

In the formula, $A^4$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{143}$ group, an —OC(=O)—O$R^{144}$ group, an —S(=O)$_2R^{145}$ group, or an —S(=O)$_2$O$R^{146}$ group; $R^{141}$, $R^{144}$, and $R^{146}$ are each independently synonymous with $R^{20}$; $R^{142}$, $R^{143}$, and $R^{145}$ are each independently synonymous with $R^{113}$ and $R^{115}$, respectively; and $n^4$ represents an integer of 0 to 2.

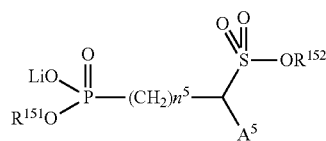

(III-5)

In the formula, $A^5$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{153}$ group, an —OC(=O)—O$R^{154}$ group, an —S(=O)$_2R^{155}$ group, or an —S(=O)$_2$O$R^{156}$ group; $R^{151}$, $R^{152}$, $R^{154}$, and $R^{156}$ are each independently synonymous with $R^{20}$; $R^{153}$ and $R^{155}$ are each independently synonymous with $R^{113}$ and $R^{115}$, respectively; and $n^5$ represents an integer of 0 to 2.

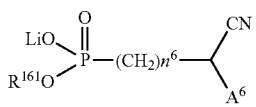

(III-6)

In the formula, $A^6$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{162}$ group, an —OC(=O)—O$R^{163}$ group, an —S(=O)$_2R^{164}$ group, or an —S(=O)$_2$O$R^{165}$ group; $R^{161}$, $R^{163}$, and $R^{165}$ are each independently synonymous with $R^{20}$; $R^{162}$ and $R^{164}$ are each independently synonymous with $R^{113}$ and $R^{115}$, respectively; and $n^6$ represents an integer of 0 to 2.

(III-7)

In the formula, $R^{172}$ represents an alkyl group having 1 to 6 carbon atoms, in which a part of hydrogen atoms are substituted with a fluorine atom; $A^7$ represents an alkoxy group having 1 to 8 carbon atoms, in which a part of hydrogen atoms may be substituted with a halogen atom, an —OC(=O)$R^{173}$ group, an —OC(=O)—O$R^{174}$ group, an —S(=O)$_2R^{175}$ group, or an —S(=O)$_2$O$R^{176}$ group; $R^{171}$, $R^{174}$, and $R^{176}$ are each independently synonymous with $R^{20}$; $R^{173}$ and $R^{175}$ are each independently synonymous with $R^{113}$ and $R^{115}$, respectively; and $n^7$ represents an integer of 0 to 2.

Specific examples and suitable examples of the compounds represented by the general formulae (III-1) to (III-7) are those as described above.

Each of the compounds represented by the general formulae (III-1) to (III-7), which is related to the third invention, may be synthesized by a method of allowing a phosphonate ester as a precursor to react with a lithium salt in the presence of a solvent, but the present invention is not limited to such a method at all.

The phosphonate ester serving as a precursor may be synthesized by a known method. For example, methods described in *Organic Letters* 2006, p. 1573, *Angewandte Chemie-International Edition*, 2010, vol. 49, #38, p. 6852-6855, German Patent No. 956404, and the like may be applied.

Specific examples of the lithium salt are the same as those described above.

Among the aforementioned lithium salts, lithium acetate, lithium chloride, lithium bromide, and lithium iodide are preferred, and lithium chloride and lithium bromide are more preferred.

An amount of the lithium salt used is preferably 0.5 mol or more, more preferably 0.7 mol or more, and still more preferably 0.9 mol or more per mol of the phosphonate ester. This is because when the amount of the lithium salt used is less than 0.5 mol, the reaction does not thoroughly proceed, so that the yield is worsened. An upper limit thereof is preferably 2 mol or less, more preferably 1.5 mol or less, and still more preferably 1.1 mol or less. This is because when the amount of the lithium salt used is more than 2 mol, a side-reaction is liable to proceed, so that the yield is worsened, and impurities increase.

Specific examples, suitable examples, and use amount of the solvent to be used for the reaction are the same as those described above.

An upper limit of a reaction temperature is preferably 120° C. or lower, more preferably 100° C. or lower, and especially preferably 80° C. or lower. This is because in the case where the reaction temperature is higher than 120° C., a side-reaction is liable to proceed. A lower limit of the reaction temperature is preferably 0° C. or higher, more preferably 10° C. or higher, and especially preferably 20° C. or higher. This is because in the case where the reaction temperature is lower than 0° C., a reaction rate is largely decreased. However, in the case where a boiling point of the solvent used is 150° C. or lower, the boiling point of the solvent is set as the upper limit of the reaction temperature, whereas in the case where a melting point of the solvent used is 0° C. or higher, the melting point of the organic solvent is set as the lower limit of the reaction temperature.

Although a reaction time varies according to the reaction temperature or the amounts of the lithium salt and solvent used, a lower limit thereof is preferably 0.5 hours or more, and more preferably 1 hour or more. This is because where the reaction time is less than 0.5 hours, the reaction does not thoroughly proceed. Meanwhile, an upper limit thereof is preferably 24 hours or less, and more preferably 16 hours or less. This is because when the reaction time is more than 24 hours, a side-reaction is liable to proceed.

EXAMPLES

[First Invention]

Synthesis Example of the lithium phosphate represented by the general formula (I) and Examples of the electrolytic solution using the same are hereunder described, but it should be construed that the present invention is by no means limited by these Examples.

Synthesis Example I-1 [Synthesis of Lithium Ethyl 2-Propynyloxycarbonylphosphonate (Compound AA57)]

10.00 g (45.4 mmol) of 2-propynyl (diethoxyphosphoryl) formate was added to a slurry of 1.73 g (40.9 mmol) of lithium chloride and 70 g of acetone, followed by refluxing for 6 hours. The resultant was cooled to room temperature, and a white crystal was separated by filtration and washed with tetrahydrofuran, followed by drying under reduced pressure to obtain 2.45 g of lithium ethyl 2-propynyloxycarbonylphosphonate (yield: 30%).

The resulting lithium ethyl 2-propynyloxycarbonylphosphonate was subjected to $^1$H-NMR measurement, thereby confirming a structure thereof.

(1) $^1$H-NMR (400 MHz, DMSO-$d_6$): δ=4.61 (dd, J=2.4, 0.9 Hz, 2H), 3.84-3.77 (m, 2H), 3.49 (t, J=2.4 Hz, 1H), 1.12 (t, J=7.1 Hz, 3H)

Examples I-1 to I-19 and Comparative Examples I-1 to I-2

[Production of Lithium Ion Secondary Battery]

94 mass % of $LiNi_{1/3}Mn_{1/3}Co_{1/3}O_2$ and 3 mass % of acetylene black (electroconductive agent) were mixed and then added to and mixed with a solution which had been prepared by dissolving 3 mass % of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby producing a positive electrode sheet. A density of the positive electrode except for the collector was 3.6 g/cm$^3$. In addition, 10 mass % of silicon (elemental substance), 80 mass % of artificial graphite ($d_{002}$=0.335 nm, negative electrode active material), and 5 mass % of acetylene black (electroconductive agent) were mixed and then added to and mixed with a solution which had been prepared by dissolving 5 mass % of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet. A density of the negative electrode except for the collector was 1.5 g/cm$^3$. In addition, the electrode sheet was analyzed by X-ray diffractometry, and a ratio [I(110)/I(004)] of the peak intensity I(110) of the (110) plane to the peak intensity I(004) of the (004) plane of the graphite crystal was 0.1. The positive electrode sheet, a micro-porous polyethylene-made film separator, and the negative electrode sheet were laminated in this order, and the nonaqueous electrolytic solution having each of compositions shown in Tables 1 to 3 was added, thereby producing a 2032-type coin battery.

[Evaluation of Low-Temperature Properties after High-Temperature Charged Storage]

<Initial Discharge Capacity>

In a thermostatic chamber at 25° C., the coin battery produced by the aforementioned method was charged up to a final voltage of 4.35 V with a constant current of 1 C and under a constant voltage for 3 hours, the temperature of the thermostatic chamber was decreased to −10° C., and then the battery was discharged down to a final voltage of 2.75 V with a constant current of 1 C, thereby determining an initial discharge capacity at −10° C.

<High-Temperature Charged Storage Test>

Subsequently, in a thermostatic chamber at 65° C., this coin battery was charged up to a final voltage of 4.35 V with a constant current of 1 C and under a constant voltage for 3 hours, and then stored for 10 days while being kept at 4.35 V. Thereafter, the battery was placed in a thermostatic chamber at 25° C., and once discharged under a constant current of 1 C to a final voltage of 2.75 V.

<Discharge Capacity after High-Temperature Charged Storage>

Further thereafter, the discharge capacity at −10° C. after the high-temperature charged storage was determined in the same manner as in the measurement of the initial discharge capacity.

<Low-Temperature Properties after High-Temperature Charged Storage>

The low-temperature properties after the high-temperature charged storage was determined from the following retention rate of the discharge capacity at −10° C.

Discharge capacity retention rate (%) at −10° C. after high-temperature charged storage=(Discharge capacity at −10° C. after high-temperature charged storage)/(Initial discharge capacity at −10° C.)×100

The battery characteristics are shown in Tables 1 to 3.

TABLE 1

| | Composition of electrolyte salt Composition of nonaqueous electrolytic solution (volume ratio of solvent) | Lithium phosphate of general formula (I) | | Discharge capacity retention rate at −10° C. after high-temperature charged storage at 65° C. (%) |
|---|---|---|---|---|
| | | Kind | Content in nonaqueous electrolytic solution (mass %) | |
| Example I-1 | 1.1 M LiPF6 EC/DMC/MEC (30/40/30) | (structure: LiO, EtO, P(=O), C(=O)O-Me) | 0.5 | 69 |
| Example I-2 | 1.1 M LiPF6 EC/MEC (30/70) | | 0.5 | 66 |
| Example I-3 | 1.1 M LiPF6 EC/VC/DMC/MEC (29/1/40/30) | | 0.008 | 70 |
| Example I-4 | 1.1 M LiPF6 EC/VC/DMC/MEC (29/1/40/30) | | 0.08 | 72 |
| Example I-5 | 1.1 M LiPF6 EC/VC/DMC/MEC (29/1/40/30) | | 0.5 | 77 |
| Example I-6 | 1.1 M LiPF6 EC/VC/DMC/MEC (29/1/40/30) | | 2 | 74 |

TABLE 2

| | Composition of electrolyte salt Composition of nonaqueous electrolytic solution (volume ratio of solvent) | Lithium phosphate of general formula (I) | | Discharge capacity retention rate at −10° C. after high-temperature charged storage at 65° C. (%) |
|---|---|---|---|---|
| | | Kind | Content in nonaqueous electrolytic solution (mass %) | |
| Example I-8 | 1.1 M LiPF6 EC/VC/DMC/MEC (29/1/40/30) | (structure: LiO, EtO, P(=O), C(=O)O-nBu) | 0.5 | 74 |
| Example I-9 | 1.1 M LiPF6 EC/VC/DMC/MEC (29/1/40/30) | (structure: LiO, nBuO, P(=O), C(=O)O-Et) | 0.5 | 72 |
| Example I-10 | 1.1 M LiPF6 EC/VC/DMC/MEC (29/1/40/30) | (structure: LiO, EtO, P(=O), C(=O)O-CH2C≡CH) | 0.5 | 78 |

TABLE 2-continued

| | Composition of electrolyte salt Composition of nonaqueous electrolytic solution (volume ratio of solvent) | Lithium phosphate of general formula (I) Kind | Content in nonaqueous electrolytic solution (mass %) | Discharge capacity retention rate at −10° C. after high-temperature charged storage at 65° C. (%) |
|---|---|---|---|---|
| Example I-11 | 1.1 M LiPF6 EC/VC/DMC/MEC (29/1/40/30) | 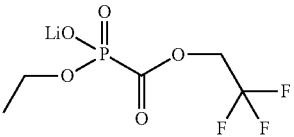 | 0.5 | 76 |
| Example I-12 | 1.1 M LiPF6 EC/VC/DMC/MEC (29/1/40/30) | 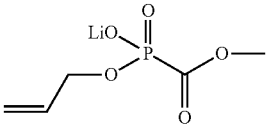 | 0.5 | 71 |
| Example I-13 | 1.1 M LiPF6 EC/VC/DMC/MEC (29/1/40/30) | 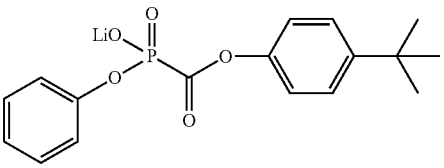 | 0.5 | 70 |
| Example I-14 | 1.1 M LiPF6 EC/VC/DMC/MEC (29/1/40/30) | 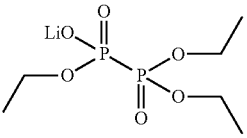 | 0.5 | 69 |
| Example I-15 | 1.1 M LiPF6 EC/VC/DMC/MEC (29/1/40/30) | 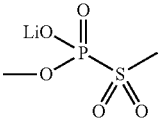 | 0.5 | 68 |

TABLE 3

| | Composition of electrolyte salt Composition of nonaqueous electrolytic solution (volume ratio of solvent) | Lithium phosphate of general formula (I) Kind | Content in nonaqueous electrolytic solution (mass %) | Discharge capacity retention rate at −10° C. after high-temperature charged storage at 65° C. (%) |
|---|---|---|---|---|
| Example I-16 | 1.1 M LiPF6 + 0.05 M LiBOB EC/FEC/VC/DMC/MEC (19/10/1/40/30) | 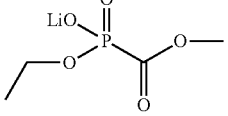 | 0.5 | 82 |
| Example I-17 | 1.1 M LiPF6 + 0.05 M LiPO2F2 EC/FEC/GBL/VC/DMC/MEC (19/7/3/1/40/30) | | 0.5 | 81 |
| Example I-18 | 1.1 M LiPF6 + 0.05 M LES EC/FEC/VC/DMC/MEC/EA (19/10/1/40/20/10) | | 0.5 | 82 |
| Example I-19 | 1.0 M LiPF6 + 0.1 M LiFSI EC/VC/DMC/MEC (29/1/40/30) | | 0.5 | 80 |

TABLE 3-continued

|  | Composition of electrolyte salt Composition of nonaqueous electrolytic solution (volume ratio of solvent) | Lithium phosphate of general formula (I) Kind | Content in nonaqueous electrolytic solution (mass %) | Discharge capacity retention rate at −10° C. after high-temperature charged storage at 65° C. (%) |
|---|---|---|---|---|
| Comparative Example I-1 | 1.1 M LiPF6 EC/VC/DMC/MEC (29/1/40/30) | None | — | 54 |
| Comparative Example I-2 | 1.1 M LiPF6 EC/VC/DMC/MEC (29/1/40/30) | (ethyl)O–P(=O)(O-ethyl)–C(=O)–O-ethyl | 0.5 | 56 |

Example I-20 and Comparative Example I-3

A positive electrode sheet was produced by using LiNi$_{1/2}$Mn$_{3/2}$O$_4$ (positive electrode active material) in place of the positive electrode active material used in Example I-1. 94 mass % of LiNi$_{1/2}$Mn$_{3/2}$O$_4$ coated with amorphous carbon and 3 mass % of acetylene black (electroconductive agent) were mixed and then added to and mixed with a solution which had been prepared by dissolving 3 mass % of polyvinylidene fluoride (binder) in 1-methyl-2-pyrrolidone in advance, thereby preparing a positive electrode mixture paste. A coin battery was produced and subjected to battery evaluation in the same manners as in Example I-1, except that this positive electrode mixture paste was applied onto one surface of an aluminum foil (collector), dried, and treated under pressure, followed by cutting into a predetermined size, thereby producing a positive electrode sheet; that in evaluating the battery, the final charging voltage and the final discharging voltage were set to 4.9 V and 2.7 V, respectively; and that the composition of the nonaqueous electrolytic solution was changed to a predetermined composition. The results are shown in Table 4.

Example I-21 and Comparative Example I-4

A negative electrode sheet was produced by using lithium titanate Li$_4$Ti$_5$O$_{12}$ (negative electrode active material) in place of the negative electrode active material used in Example I-1. 80 mass % of lithium titanate Li$_4$Ti$_5$O$_{12}$ and 15 mass % of acetylene black (electroconductive agent) were mixed and then added to and mixed with a solution which had been prepared by dissolving 5 mass % of polyvinylidene fluoride (binder) in 1-methyl-2-pyrrolidone in advance, thereby preparing a negative electrode mixture paste. A coin battery was produced and subjected to battery evaluation in the same manners as in Example I-1, except that this negative electrode mixture paste was applied onto one surface of a copper foil (collector), dried, and treated under pressure, followed by cutting into a predetermined size, thereby producing a negative electrode sheet; that in evaluating the battery, the final charging voltage and the final discharging voltage were set to 2.8 V and 1.2 V, respectively; and that the composition of the nonaqueous electrolytic solution was changed to a predetermined composition. The results are shown in Table 5.

TABLE 4

|  | Composition of electrolyte salt Composition of nonaqueous electrolytic solution (volume ratio of solvent) | Lithium phosphate of general formula (I) Kind | Content in nonaqueous electrolytic solution (mass %) | Discharge capacity retention rate at −10° C. after high-temperature charged storage at 65° C. (%) |
|---|---|---|---|---|
| Example I-20 | 1.1 M LiPF6 EC/FEC/MEC/DEC (20/10/40/30) | LiO–P(=O)(O-ethyl)–C(=O)–O–methyl | 0.5 | 70 |
| Comparative Example I-3 |  | None | — | 46 |

TABLE 5

| | Composition of electrolyte salt Composition of nonaqueous electrolytic solution (volume ratio of solvent) | Lithium phosphate of general formula (I) Kind | Content in nonaqueous electrolytic solution (mass %) | Discharge capacity retention rate at −10° C. after high-temperature charged storage at 65° C. (%) |
|---|---|---|---|---|
| Example I-21 | 1.1 M LiPF6 PC/DEC (30/70) | [structure: LiO–P(=O)(OEt)–C(=O)–O–CH3] | 0.5 | 85 |
| Comparative Example I-4 | | None | — | 60 |

Examples I-22 to I-23

Lithium secondary batteries were produced and subjected to battery evaluation in the same manners as in Comparative Example I-1, except for using a positive electrode produced by adding a predetermined amount of the lithium phosphate represented by the general formula (I) with the total mass of the positive electrode active material being taken as 100. The results are shown in Table 6.

Examples I-24 to I-25

Lithium secondary batteries were produced and subjected to battery evaluation in the same manners as in Comparative Example I-1, except for not adding the lithium phosphate represented by the general formula (I) to the positive electrode and using a negative electrode produced by adding a predetermined amount of the lithium phosphate represented by the general formula (I) with the total mass of the negative electrode active material being taken as 100. The results are shown in Table 6.

TABLE 6

| | Composition of electrolyte salt Composition of nonaqueous electrolytic solution (volume ratio of solvent) | Lithium phosphate of general formula (I) Kind | Addition part | Content in positive electrode or negative electrode active material (mass %) | Discharge capacity retention rate at −10° C. after high-temperature charged storage at 65° C. (%) |
|---|---|---|---|---|---|
| Example I-22 | 1.1 M LiPF6 EC/VC/DMC/MEC (29/1/40/30) | [structure: LiO–P(=O)(OEt)–C(=O)–O–CH3] | Positive electrode | 0.5 | 75 |
| Example I-23 | | [structure: LiO–P(=O)(OEt)–C(=O)–OLi] | | 0.5 | 72 |
| Example I-24 | | [structure: LiO–P(=O)(OEt)–C(=O)–O–CH3] | Negative electrode | 0.5 | 74 |
| Example I-25 | | [structure: (LiO)2–P(=O)–C(=O)–O–CH3] | | 0.5 | 70 |

All of the lithium secondary batteries of Examples I-1 to I-19 as described above are remarkably improved in the electrochemical characteristics in a broad temperature range, as compared with the lithium secondary batteries of Comparative Example I-1 which is in the case of not adding the lithium phosphate represented by the general formula (I) and Comparative Example I-2 which is in the case of adding triethyl phosphonoformate, in the nonaqueous electrolytic solution of the present invention. In the light of the above, it has become clear that in the nonaqueous electrolytic solution having an electrolyte salt dissolved in a nonaqueous solvent, the effects of the present invention are peculiar effects brought in the case of containing the lithium phosphate in which the specified polar group ($X^1$) is bound directly to the phosphorus atom (P).

In addition, from the comparison of Example I-20 with Comparative Example I-3 and the comparison of Example I-21 with Comparative Example I-4 in the case of using lithium nickel manganate ($LiNi_{1/2}Mn_{3/2}O_4$) for the positive electrode and also in the case of using lithium titanate for the negative electrode, the same effects are brought. In consequence, it is evident that the effects of the present invention according to the first invention are not an effect relying upon a specified positive electrode or negative electrode.

In addition, from the comparison of Examples I-22 to I-25 with Comparative Example I-1, it has become clear that the effects of the present invention are brought even in the case of containing the lithium phosphate represented by the general formula (I) in other part than the electrolytic solution.

Furthermore, the nonaqueous electrolytic solution of the first invention also has an effect for improving the discharging properties in the case of using a lithium primary battery in a broad temperature range.

[Second Invention]

Synthesis Examples of the compound represented by the general formula (II) and Examples of the electrolytic solution using such a compound are hereunder described, but it should be construed that the present invention is by no means limited by these Examples.

Synthesis Example II-1 [Synthesis of Lithium Ethyl (2-Oxo-1,3-dioxolan-4-yl)phosphonate (Compound a3)]

11.95 g (53.3 mmol) of diethyl (2-oxo-1,3-dioxolan-4-yl) phosphonate (Compound d2) was added to a slurry of 2.14 g (50.7 mmol) of lithium chloride and 30 g of methyl isobutyl ketone, followed by heating under reflux for 10 hours. The methyl isobutyl ketone was then distilled off by concentration under reduced pressure. A deposited white crystal was washed with diethyl ether, separated by filtration, and then dried under reduced pressure to obtain 3.90 g of lithium ethyl (2-oxo-1,3-dioxolan-4-yl)phosphonate (yield: 39%).

The obtained lithium ethyl (2-oxo-1,3-dioxolan-4-yl) phosphonate was subjected to $^1$H-NMR measurement, thereby confirming a structure thereof.

$^1$H-NMR (400 MHz, DMSO-$d_6$): δ=4.64-4.56 (m, 1H), 4.49-4.41 (m, 1H), 4.06-3.98 (m, 1H), 3.89-3.79 (m, 2H), 1.13 (t, J=7.1 Hz, 3H)

Synthesis Example II-2 [Synthesis of Diphenyl (2-Oxo-1,3-dioxolan-4-yl)phosphonate (Compound d9)]

6.13 g (50.0 mmol) of chloroethylene carbonate and 11.71 g (0.05 mol) of diphenyl phosphite were dissolved in 50 g of ethyl acetate, followed by cooling to 10° C. To this solution, 5.06 g (0.05 mol) of triethylamine was added dropwise at 10° C. to 15° C. over 15 minutes, followed by stirring at room temperature for 3 hours. A formed salt was filtered, the solvent was concentrated under reduced pressure, and the resulting residue was purified by silica gel chromatography (elution with ethyl acetate/hexane=1/1), thereby obtaining 5.6 g of diphenyl (2-oxo-1,3-dioxolan-4-yl)phosphonate (yield: 35%).

The obtained diphenyl (2-oxo-1,3-dioxolan-4-yl)phosphonate was subjected to $^1$H-NMR, thereby confirming its structure. $^1$H-NMR (400 MHz, CDCl$_3$): δ=7.38-7.34 (m, 4H), 7.26-7.18 (m, 6H), 5.14-5.09 (m, 1H), 4.89-4.52 (m, 2H)

Synthesis Example II-3 [Synthesis of Bis(2,2,2-trifluoroethyl) (2-Oxo-1,3-dioxolan-4-yl)phosphonate (Compound d6)]

The experiment was performed in the same manner as in Synthesis Example II-2, except for using bistrifluoroethyl phosphite in place of the diphenyl phosphite, thereby obtaining 9.1 g of bis(2,2,2-trifluoroethyl) (2-oxo-1,3-dioxolan-4-yl)phosphonate (yield: 55%).

The obtained bis(2,2,2-trifluoroethyl) (2-oxo-1,3-dioxolan-4-yl)phosphonate was subjected to $^1$H-NMR, thereby confirming its structure.

$^1$H-NMR (400 MHz, CDCl$_3$): δ=5.00-4.96 (m, 1H), 4.78-4.62 (m, 2H), 4.60-4.48 (m, 4H)

Synthesis Example II-4 [Synthesis of Lithium Ethyl (2,5-Dioxopyrolidin-1-yl)phosphonate (Compound g3)]

The experiment was performed in the same manner as in Synthesis Example II-1, except for using diethyl (2,5-dioxopyrolidin-1-yl)phosphonate in place of the diethyl (2-oxo-1,3-dioxolan-4-yl)phosphonate, thereby obtaining 7.0 g of lithium ethyl (2,5-dioxopyrolidin-1-yl)phosphonate (yield: 65%).

The obtained lithium ethyl (2,5-dioxopyrolidin-1-yl) phosphonate was subjected to $^1$H-NMR, thereby confirming its structure.

$^1$H-NMR (400 MHz, DMSO-$d_6$): δ=3.87-3.80 (m, 2H), 2.61 (s, 4H), 1.09 (t, J=7.1 Hz, 3H)

Examples II-1 to II-34 and II-41 to II-58 and Comparative Examples II-1 to II-2

[Production of Lithium Ion Secondary Battery]

94 mass % of $LiNi_{1/3}Mn_{1/3}Co_{1/3}O_2$ and 3 mass % of acetylene black (electroconductive agent) were mixed and then added to and mixed with a solution which had been prepared by dissolving 3 mass % of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby producing a positive electrode sheet. A density of the positive electrode except for the collector was 3.6 g/cm$^3$. In addition, 10 mass % of silicon (elemental substance), 80 mass % of artificial graphite ($d_{002}$=0.335 nm, negative electrode active material), and 5 mass % of acetylene black (electroconductive agent) were mixed and then added to and mixed with a solution which had been prepared by dissolving 5 mass % of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet. A density of the negative electrode except for the collector was 1.5 g/cm³. In addition, the electrode sheet was analyzed by X-ray diffractometry, and a ratio [I(110)/I(004)] of the peak intensity I(110) of the (110) plane to the peak intensity I(004) of the (004) plane of the graphite crystal was 0.1. The positive electrode sheet, a micro-porous polyethylene-made film separator, and the negative electrode sheet were laminated in this order, and the nonaqueous electrolytic solution having each of compositions shown in Tables 7 to 13 was added, thereby producing a 2032-type coin battery.

[Evaluation of Low-Temperature Properties after High-Temperature Charged Storage]

<Initial Discharge Capacity>

The initial discharge capacity at −10° C. was determined in the same manner as in Example I-1.

<High-Temperature Charged Storage Test>

Subsequently, in a thermostatic chamber at 60° C., this coin battery was charged up to a final voltage of 4.35 V with a constant current of 1 C and under a constant voltage for 3 hours, and then stored for 10 days while being kept at 4.35 V. Thereafter, the battery was placed in a thermostatic chamber at 25° C., and once discharged under a constant current of 1 C to a final voltage of 2.75 V.

<Discharge Capacity after High-Temperature Charged Storage>

The discharge capacity at −10° C. after the high-temperature charged storage was determined in the same manner as in Example I-1.

<Low-Temperature Properties after High-Temperature Charged Storage>

The discharge capacity retention rate (%) at −10° C. after the high-temperature charged storage was determined in the same manner as in Example I-1.

The battery characteristics are shown in Tables 7 to 13.

TABLE 7

|  | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-1 | 1.1 M LiPF6 EC/DMC/MEC (30/40/30) | 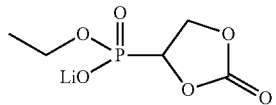 | 1 | 70 |
| Example II-2 | 1.1 M LiPF6 EC/MEC (30/70) | | 1 | 68 |
| Example II-3 | 1.1 M LiPF6 EC/VC/DMC/MEC (29/1/40/30) | | 0.05 | 73 |
| Example II-4 | 1.1 M LiPF6 EC/VC/DMC/MEC (29/1/40/30) | | 0.5 | 75 |
| Example II-5 | 1.1 M LiPF6 EC/VC/DMC/MEC (29/1/40/30) | | 1 | 79 |
| Example II-6 | 1.1 M LiPF6 EC/VC/DMC/MEC (29/1/40/30) | | 3 | 76 |

TABLE 8

|  | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-7 | 1.1 M LiPF6 EC/VC/DMC/MEC (29/1/40/30) | 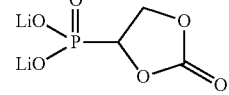 | 1 | 82 |
| Example II-8 | 1.1 M LiPF6 EC/VC/DMC/MEC (29/1/40/30) | 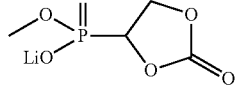 | 1 | 78 |

TABLE 8-continued

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-9 | 1.1 M LiPF6 EC/VC/DMC/MEC (29/1/40/30) | F3C–O–P(=O)(OLi)–(dioxolan-2-one) | 1 | 81 |
| Example II-10 | 1.1 M LiPF6 EC/VC/DMC/MEC (29/1/40/30) | HC≡C–CH2–O–P(=O)(OLi)–(dioxolan-2-one) | 1 | 80 |
| Example II-11 | 1.1 M LiPF6 EC/VC/DMC/MEC (29/1/40/30) | Ph–O–P(=O)(OLi)–(dioxolan-2-one) | 1 | 78 |
| Example II-12 | 1.1 M LiPF6 EC/VC/DMC/MEC (29/1/40/30) | Et–O–P(=O)(OLi)–(γ-butyrolactone) | 1 | 78 |
| Example II-13 | 1.1 M LiPF6 EC/VC/DMC/MEC (29/1/40/30) | Ph–O–P(=O)(OLi)–(γ-butyrolactone) | 1 | 76 |
| Example II-14 | 1.1 M LiPF6 EC/VC/DMC/MEC (29/1/40/30) | Et–O–P(=O)(OLi)–(dimethyl γ-butyrolactone) | 1 | 76 |
| Example II-15 | 1.1 M LiPF6 EC/VC/DMC/MEC (29/1/40/30) | Et–O–P(=O)(OLi)–(succinic anhydride) | 1 | 77 |

TABLE 9

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-16 | 1.1 M LiPF6 + 0.05 M LiBOB EC/FEC/VC/DMC/MEC (19/10/1/40/30) | Et–O–P(=O)(OLi)–(dioxolan-2-one) | 1 | 85 |
| Example II-17 | 1.1 M LiPF6 + 0.05 M LiPO2F2 EC/FEC/GBL/VC/DMC/MEC (19/7/3/1/40/30) | Et–O–P(=O)(OLi)–(dioxolan-2-one) | 1 | 84 |

TABLE 9-continued

| | Composition of electrolyte salt Composition of nonaqueous electrolytic solution (volume ratio of solvent) | Compound of general formula (II) Kind | Compound of general formula (II) Content in nonaqueous electrolytic solution (mass %) | Discharge capacity retention rate at −10° C. after high-temperature charged storage at 60° C. (%) |
|---|---|---|---|---|
| Example II-18 | 1.1 M LiPF6 + 0.05 M LES EC/FEC/VC/DMC/MEC/EA (19/10/1/40/20/10) | | 1 | 84 |
| Example II-19 | 0.7 M LiPF6 + 0.4 M LiFSI EC/VC/DMC/MEC (29/1/40/30) | | 1 | 83 |
| Comparative Example II-1 | 1.1 M LiPF6 EC/VC/DMC/MEC (29/1/40/30) | None | — | 57 |
| Comparative Example II-2 | 1.1 M LiPF6 EC/VC/DMC/MEC (29/1/40/30) | 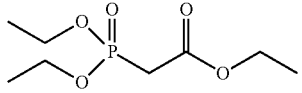 | 1 | 58 |

TABLE 10

| | Composition of electrolyte salt Composition of nonaqueous electrolytic solution (volume ratio of solvent) | Compound of general formula (II) Kind | Compound of general formula (II) Content in nonaqueous electrolytic solution (mass %) | Discharge capacity retention rate at −10° C. after high-temperature charged storage at 60° C. (%) |
|---|---|---|---|---|
| Example II-20 | 1.1 M LiPF6 EC/DMC/MEC (30/40/30) | 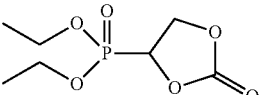 | 1 | 68 |
| Example II-21 | 1.1 M LiPF6 EC/MEC (30/70) | | 1 | 66 |
| Example II-22 | 1.1 M LiPF6 EC/VC/DMC/MEC (29/1/40/30) | | 0.05 | 70 |
| Example II-23 | 1.1 M LiPF6 EC/VC/DMC/MEC (29/1/40/30) | | 0.5 | 71 |
| Example II-24 | 1.1 M LiPF6 EC/VC/DMC/MEC (29/1/40/30) | | 1 | 76 |
| Example II-25 | 1.1 M LiPF6 EC/VC/DMC/MEC (29/1/40/30) | | 4 | 74 |

TABLE 11

| | Composition of electrolyte salt Composition of nonaqueous electrolytic solution (volume ratio of solvent) | Compound of general formula (II) Kind | Compound of general formula (II) Content in nonaqueous electrolytic solution (mass %) | Discharge capacity retention rate at −10° C. after high-temperature charged storage at 60° C. (%) |
|---|---|---|---|---|
| Example II-26 | 1.1 M LiPF6 EC/VC/DMC/MEC (29/1/40/30) | 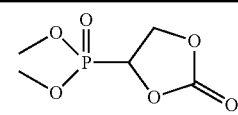 | 1 | 75 |

TABLE 11-continued

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-27 | 1.1 M LiPF6 EC/VC/DMC/MEC (29/1/40/30) | [structure] | 1 | 80 |
| Example II-28 | 1.1 M LiPF6 EC/VC/DMC/MEC (29/1/40/30) | [structure] | 1 | 74 |
| Example II-29 | 1.1 M LiPF6 EC/VC/DMC/MEC (29/1/40/30) | [structure] | 1 | 74 |
| Example II-30 | 1.1 M LiPF6 EC/VC/DMC/MEC (29/1/40/30) | [structure] | 1 | 73 |
| Example II-31 | 1.1 M LiPF6 + 0.05 M LiBOB EC/FEC/VC/DMC/MEC (19/10/1/40/30) | [structure] | 1 | 81 |
| Example II-32 | 1.1 M LiPF6 + 0.05 M LiPO2F2 EC/FEC/CBL/VC/DMC/MEC (19/7/3/1/40/30) | | 1 | 80 |
| Example II-33 | 1.1 M LiPF6 + 0.05 M LES EC/FEC/VC/DMC/MEC/EA (19/10/1/40/20/10) | | 1 | 79 |
| Example II-34 | 0.7 M LiPF6 + 0.4 M LiFSI EC/VC/DMC/MEC (29/1/40/30) | | 1 | 78 |

TABLE 12

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-41 | 1.1M LiPF6 EC/DMC/MEC (30/40/30) | [structure] | 1 | 65 |
| Example II-42 | 1.1M LiPF6 EC/MEC (30/70) | | 1 | 63 |
| Example II-43 | 1.1M LiPF6 EC/VC/DMC/MEC (29/1/40/30) | | 0.05 | 71 |
| Example II-44 | 1.1M LiPF6 EC/VC/DMC/MEC (29/1/40/30) | | 0.5 | 73 |

TABLE 12-continued

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-45 | 1.1M LiPF6 EC/VC/DMC/MEC (29/1/40/30) | | 1 | 78 |
| Example II-46 | 1.1M LiPF6 EC/VC/DMC/MEC (29/1/40/30) | | 4 | 73 |

15

TABLE 13

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-47 | 1.1M LiPF6 EC/VC/DMC/MEC (29/1/40/30) | [structure] | 1 | 78 |
| Example II-48 | 1.1M LiPF6 EC/VC/DMC/MEC (29/1/40/30) | [structure] | 1 | 75 |
| Example II-49 | 1.1M LiPF6 EC/VC/DMC/MEC (29/1/40/30) | [structure] | 1 | 74 |
| Example II-50 | 1.1M LiPF6 EC/VC/DMC/MEC (29/1/40/30) | [structure] | 1 | 75 |
| Example II-51 | 1.1M LiPF6 EC/VC/DMC/MEC (29/1/40/30) | [structure] | 1 | 73 |
| Example II-52 | 1.1M LiPF6 EC/VC/DMC/MEC (29/1/40/30) | [structure] | 1 | 72 |

TABLE 13-continued

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-53 | 1.1M LiPF6 EC/VC/DMC/MEC (29/1/40/30) | 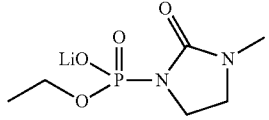 | 1 | 72 |
| Example II-54 | 1.1M LiPF6 EC/VC/DMC/MEC (29/1/40/30) | 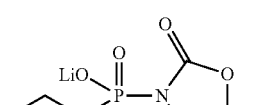 | 1 | 73 |
| Example II-55 | 1.1M LiPF6 + 0.05M LiBOB EC/FEC/VC/DMC/MEC (19/10/1/40/30) | 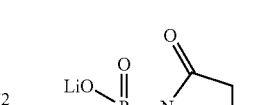 | 1 | 82 |
| Example II-56 | 1.1M LiPF6 + 0.05M LiPO2F2 EC/FEC/GBL/VC/DMC/MEC (19/7/3/1/40/30) | | 1 | 81 |
| Example II-57 | 1.1M LiPF6 + 0.05M LES EC/FEC/VC/DMC/MEC/EA (19/10/1/40/20/10) | | 1 | 81 |
| Example II-58 | 0.7M LiPF6 + 0.4M LiFSI EC/VC/DMC/MEC (29/1/40/30) | | 1 | 79 |

Examples II-35 and II-59 and Comparative Example II-3

A positive electrode sheet was produced by using LiNi$_{1/2}$Mn$_{3/2}$O$_4$ (positive electrode active material) in place of the positive electrode active material used in Example II-1. 94 mass % of LiNi$_{1/2}$Mn$_{3/2}$O$_4$ coated with amorphous carbon and 3 mass % of acetylene black (electroconductive agent) were mixed and then added to and mixed with a solution which had been prepared by dissolving 3 mass % of polyvinylidene fluoride (binder) in 1-methyl-2-pyrrolidone in advance, thereby preparing a positive electrode mixture paste. A coin battery was produced and subjected to battery evaluation in the same manners as in Example II-1, except that this positive electrode mixture paste was applied onto one surface of an aluminum foil (collector), dried, and treated under pressure, followed by cutting into a predetermined size, thereby producing a positive electrode sheet; that in evaluating the battery, the final charging voltage and the final discharging voltage were set to 4.9 V and 2.7 V, respectively; and that the composition of the nonaqueous electrolytic solution was changed to a predetermined composition. The results are shown in Tables 14 and 15.

TABLE 14

| | Composition of electrolyte salt Composition of nonaqueous electrolytic solution (volume ratio of solvent) | Compound of general formula (II) Kind | Content in nonaqueous electrolytic solution (mass %) | Discharge capacity retention rate at −10° C. after high-temperature charged storage at 60° C. (%) |
|---|---|---|---|---|
| Example II-35 | 1.1M LiPF6 EC/FEC/MEC/DEC (20/10/40/30) | 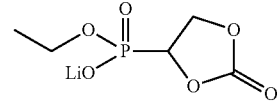 | 1 | 71 |
| Comparative Example II-3 | | None | — | 51 |

TABLE 15

| | Composition of electrolyte salt Composition of nonaqueous electrolytic solution (volume ratio of solvent) | Compound of general formula (II) | | Discharge capacity retention rate at −10° C. after high-temperature charged storage at 60° C. (%) |
|---|---|---|---|---|
| | | Kind | Content in nonaqueous electrolytic solution (mass %) | |
| Example II-59 | 1.1M LiPF6 EC/FEC/MEC/DEC (20/10/40/30) | 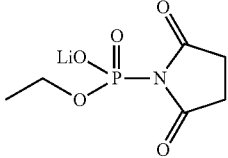 | 1 | 69 |

Examples II-36 and II-60 and Comparative Example II-4

A negative electrode sheet was produced by using lithium titanate $Li_4Ti_5O_{12}$ (negative electrode active material) in place of the negative electrode active material used in Example II-1. 80 mass % of lithium titanate $Li_4T_5O_{12}$ and 15 mass % of acetylene black (electroconductive agent) were mixed and then added to and mixed with a solution which had been prepared by dissolving 5 mass % of polyvinylidene fluoride (binder) in 1-methyl-2-pyrrolidone in advance, thereby preparing a negative electrode mixture paste. A coin battery was produced and subjected to battery evaluation in the same manners as in Example II-1, except that this negative electrode mixture paste was applied onto one surface of a copper foil (collector), dried, and treated under pressure, followed by cutting into a predetermined size, thereby producing a negative electrode sheet; that in evaluating the battery, the final charging voltage and the final discharging voltage were set to 2.8 V and 1.2 V, respectively; and that the composition of the nonaqueous electrolytic solution was changed to a predetermined composition. The results are shown in Tables 16 and 17.

TABLE 16

| | Composition of electrolyte salt Composition of nonaqueous electrolytic solution (volume ratio of solvent) | Compound of general formula (II) | | Discharge capacity retention rate at −10° C. after high-temperature charged storage at 60° C. (%) |
|---|---|---|---|---|
| | | Kind | Content in nonaqueous electrolytic solution (mass %) | |
| Example II-36 | 1.1M LiPF6 PC/DEC (30/70) | 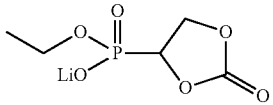 | 1 | 86 |
| Comparative Example II-4 | | None | — | 63 |

TABLE 17

| | Composition of electrolyte salt Composition of nonaqueous electrolytic solution (volume ratio of solvent) | Compound of general formula (II) | | Discharge capacity retention rate at −10° C. after high-temperature charged storage at 60° C. (%) |
|---|---|---|---|---|
| | | Kind | Content in nonaqueous electrolytic solution (mass %) | |
| Example II-60 | 1.1M LiPF6 PC/DEC (30/70) | 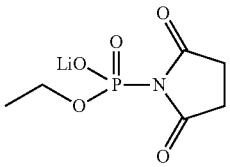 | 1 | 83 |

Examples II-37, II-38, II-61, and II-62

Lithium secondary batteries were produced and subjected to battery evaluation in the same manners as in Comparative Example II-1, except for using a positive electrode produced by adding a predetermined amount of the compound represented by the general formula (II) with the total mass of the positive electrode active material being taken as 100. The results are shown in Tables 18 and 19.

Examples II-39, II-40, II-63, and II-64

Lithium secondary batteries were produced and subjected to battery evaluation in the same manners as in Comparative Example II-1, except for not adding the compound represented by the general formula (II) to the positive electrode and using a negative electrode produced by adding a predetermined amount of the compound represented by the general formula (II) with the total mass of the negative electrode active material being taken as 100. The results are shown in Tables 18 and 19.

TABLE 18

| | Composition of electrolyte salt Composition of nonaqueous electrolytic solution (volume ratio of solvent) | Compound of general formula (II) | | Addition part | Content in positive electrode or negative electrode active material (mass %) | Discharge capacity retention rate at −10° C. after high-temperature charged storage at 60° C. (%) |
|---|---|---|---|---|---|---|
| | | Kind | | | | |
| Example II-37 | 1.1M LiPF6 EC/VC/DMC/MEC (29/1/40/30) | [structure: ethyl-O-P(=O)(OLi)-CH(cyclic carbonate)] | | Positive electrode | 0.3 | 77 |
| Example II-38 | | [structure: (LiO)2P(=O)-CH(cyclic carbonate)] | | | 0.3 | 78 |
| Example II-39 | | [structure: ethyl-O-P(=O)(OLi)-CH(cyclic carbonate)] | | Negative electrode | 0.3 | 75 |
| Example II-40 | | [structure: (LiO)2P(=O)-CH(cyclic carbonate)] | | | 0.3 | 76 |

TABLE 19

| | Composition of electrolyte salt Composition of nonaqueous electrolytic solution (volume ratio of solvent) | Compound of general formula (II) | | Addition part | Content in positive electrode or negative electrode active material (mass %) | Discharge capacity retention rate at −10° C. after high-temperature charged storage at 60° C. (%) |
|---|---|---|---|---|---|---|
| | | Kind | | | | |
| Example II-61 | 1.1M LiPF6 EC/VC/DMC/MEC (29/1/40/30) | [structure: ethyl-O-P(=O)(OLi)-N(succinimide)] | | Positive electrode | 0.3 | 73 |

TABLE 19-continued

| | Composition of electrolyte salt Composition of nonaqueous electrolytic solution (volume ratio of solvent) | Compound of general formula (II) | | Content in positive electrode or negative electrode active material (mass %) | Discharge capacity retention rate at −10° C. after high-temperature charged storage at 60° C. (%) |
|---|---|---|---|---|---|
| | | Kind | Addition part | | |
| Example II-62 | | 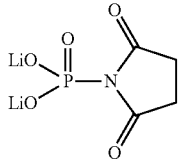 | | 0.3 | 74 |
| Example II-63 | | 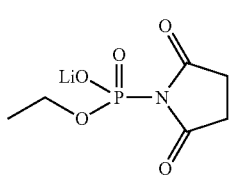 | Negative electrode | 0.3 | 70 |
| Example II-64 | | 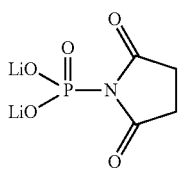 | | 0.3 | 72 |

All of the lithium secondary batteries of Examples II-1 to II-34 as described above are remarkably improved in the electrochemical characteristics in a broad temperature range, as compared with the lithium secondary batteries of Comparative Example II-1 which is in the case of not adding the compound represented by the general formula (II) and Comparative Example II-2 which is in the case of adding triethyl phosphonoacetate, in the nonaqueous electrolytic solution of the present invention. In the light of the above, it has become clear that in the nonaqueous electrolytic solution having an electrolyte salt dissolved in a nonaqueous solvent, the effects of the present invention are peculiar effects brought in the case of containing the compound in which the specified cyclic polar group ($X^2$) is bound directly to the phosphorus atom (P).

From the comparison of Example II-35 with Comparative Example II-3 and the comparison of Example II-36 with Comparative Example II-4 in the case of using lithium nickel manganate ($LiNi_{1/2}Mn_{3/2}O_4$) for the positive electrode and also in the case of using lithium titanate for the negative electrode, the same effects are brought. In consequence, it is evident that the effects of the present invention according to the second invention are not an effect relying upon a specified positive electrode or negative electrode.

From the comparison of Examples II-37 to II-40 with Comparative Example II-1, it has become clear that the effects of the present invention are brought even in the case of containing the compound represented by the general formula (II), in which the specified cyclic polar group ($X^2$) is bound directly to the phosphorus atom (P) in other part than the electrolytic solution.

In addition, it is noted from Examples II-41 to II-64, in the general formula (II), in the case where $X^2$ is a cyclic polar group containing a —C(=O)—N— group, the same effects as in the case where $X^2$ is a cyclic polar group containing a —C(=O)—O— group are also brought.

Furthermore, the nonaqueous electrolytic solution of the second invention also has an effect for improving the discharging properties in the case of using a lithium primary battery in a broad temperature range.

[Third Invention]

Synthesis Examples of the compound represented by the general formula (III) and Examples of the electrolytic solution using such a compound are hereunder described, but it should be construed that the present invention is by no means limited by these Examples.

Synthesis Example III-1 [Synthesis of Lithium Ethyl (1-Acetoxy-2-ethoxy-2-oxoethyl)phosphonate (Compound B39)]

In a 100-mL glass-made flask, 6.00 g (21.3 mmol) of ethyl 2-acetoxy-2-(diethoxyphosphoryl)acetate, 50 mL of methyl isobutyl ketone, and 0.72 g (17.0 mmol) of lithium chloride were added. The contents were stirred at a bath temperature of 100° C. for 19 hours. A deposited solid was filtered to obtain 9.10 g of a white solid. This was dried in vacuum at a bath temperature of 100° C., thereby obtaining 4.30 g of lithium ethyl (1-acetoxy-2-ethoxy-2-oxoethyl)phosphonate as a white solid (yield: 97%).

The obtained lithium ethyl (1-acetoxy-2-ethoxy-2-oxoethyl)phosphonate was subjected to $^1$H-NMR measurement, thereby confirming a structure thereof. The results are shown below.

$^1$H-NMR (400 MHz, DMSO-$d_1$): δ4.80 (1H, d, J=15.2 Hz), 3.95-4.1 (2H, m), 3.7-3.85 (2H, m), 2.05 (3H, s), 1.16 (3H, t, J=7.1 Hz), 1.10 (3H, t, J=7.1 Hz)

Synthesis Example III-2 [Synthesis of Lithium Ethyl (2-Methoxy-1-((methylsulfonyl)oxy)-2-oxoethyl)phosphonate (Compound B17)]

In a 200-mL flask, 6.00 g (19.7 mmol) of methyl-2-(diethoxyphosphoryl)-2-((methylsulfonyl)oxy)acetate, 90 mL of methyl isobutyl ketone, and 0.84 g (19.7 mmol) of lithium chloride were added. The contents were stirred at a bath temperature of 70° C. for 64 hours. An insoluble matter was filtered, and a filtrate was concentrated under reduced pressure. A concentrate was dissolved in 5 mL of water and washed three times with 10 mL of toluene. An aqueous layer was concentrated under reduced pressure and then dried in vacuum at a bath temperature of 60° C., thereby obtaining 3.43 g of lithium ethyl (2-methoxy-1-((methylsulfonyl)oxy)-2-oxoethyl)phosphonate as a white solid (yield: 62%).

The obtained lithium ethyl (2-methoxy-1-((methylsulfonyl)oxy)-2-oxoethyl)phosphonate was subjected to $^1$H-NMR measurement, thereby confirming a structure thereof. The results are shown below.

$^1$H-NMR (400 MHz, DMSO-$d_6$): δ4.91 (1H, d, J=15.7 Hz), 3.75-3.9 (2H, m), 3.66 (3H, s), 3.20 (3H, s), 1.12 (3H, t, J=7.0 Hz)

Synthesis Example III-3 [Synthesis of Lithium Ethyl ((Diethoxyphosphoryl)methyl)phosphonate (Compound C11)]

In a 100-mL flask, 5.00 g (17.3 mmol) of tetraethyl methylenediphosphonate and 10 mL of water were added. 0.65 g (15.6 mmol) of lithium hydroxide monohydrate was further added, and the contents were stirred at room temperature for 23 hours. 20 mL of dimethyl carbonate was added, followed by concentration under reduced pressure. To a concentrate, 20 mL of dimethyl carbonate was added, and the contents were stirred at room temperature for 24 hours. A deposited solid was filtered and dried in vacuum at a bath temperature of 50° C., thereby obtaining 3.21 g of lithium ethyl ((diethoxyphosphoryl)methyl)phosphonate as a white solid (yield: 82%).

The obtained lithium ethyl ((diethoxyphosphoryl)methyl)phosphonate was subjected to $^1$H-NMR measurement, thereby confirming a structure thereof. The results are shown below.

$^1$H-NMR (400 MHz, DMSO-$d_6$): δ4.10-3.95 (m, 4H), 3.80-3.65 (m, 2H), 2.03 (dd, J=20, 19 Hz, 1H), 1.22 (t, J=7 Hz, 6H), 1.12 (t, J=7 Hz, 3H)

Synthesis Example III-4 [Synthesis of Lithium Ethyl (2,2,2-Trifluoro-1-((methylsulfonyl)oxy)ethyl)phosphonate (Compound B50)]

In a 100-mL flask, 6.00 g (19.1 mmol) of 1-(diethoxyphosphoryl)-2,2,2-trifluoroethyl methanesulfonate, 1.33 g (15.3 mmol) of lithium bromide, and 50 mL of methyl isobutyl ketone were added. The contents were stirred at a bath temperature of 100° C. for 59 hours. A deposited solid was filtered and dried in vacuum at a bath temperature of 40° C. There was thus obtained 4.17 g of lithium ethyl (2,2,2-trifluoro-1-((methylsulfonyl)oxy)ethyl)phosphonate as a while solid (yield: 93%).

The obtained lithium ethyl (2,2,2-trifluoro-1-((methylsulfonyl)oxy)ethyl)phosphonate was subjected to $^1$H-NMR measurement, thereby confirming a structure thereof. The results are shown below.

$^1$H-NMR (400 MHz, DMSO-$d_6$): δ4.78-4.65 (m, 1H), 3.88-3.78 (m, 2H), 3.37 (s, 3H), 1.12 (t, J=7 Hz, 3H)

Synthesis Example III-5 [Synthesis of Lithium Ethyl (1-Acetoxy-2,2,2-trifluoroethyl)phosphonate (Compound G7)]

In a 100-mL flask, 6.47 g (22.0 mmol) of 1-(diethoxyphosphoryl)-2,2,2-trifluoroethyl acetate, 1.53 g (17.6 mmol) of lithium bromide, and 30 mL of methyl isobutyl ketone were added. The contents were stirred at a bath temperature of 100° C. for 54 hours. A deposited solid was filtered and dried in vacuum at a bath temperature of 70° C. There was thus obtained 3.65 g of lithium ethyl (1-acetoxy-2,2,2-trifluoroethyl)phosphonate as a white solid (yield: 81%).

The obtained lithium ethyl (1-acetoxy-2,2,2-trifluoroethyl)phosphonate was subjected to $^1$H-NMR measurement, thereby confirming a structure thereof. The results are shown below.

$^1$H-NMR (400 MHz, DMSO-$d_6$): δ5.32-5.19 (m, 1H), 3.80 (quintet, J=7.1 Hz, 2H), 2.11 (s, 3H), 1.14 (t, J=7.0 Hz, 3H)

Synthesis Example III-6 [Synthesis of Lithium Ethyl (Cyanomethyl)phosphonate (Compound F9)]

In a 100-mL flask, 5.06 g (28.6 mmol) of diethyl (cyanomethyl)phosphonate, 1.97 g (22.7 mmol) of lithium bromide, and 40 mL of methyl isobutyl ketone were added. The contents were stirred at a bath temperature of 100° C. for 70 hours. A deposited solid was filtered and dried in vacuum at a bath temperature of 70° C. There was thus obtained 3.59 g of lithium ethyl (cyanomethyl)phosphonate as a white solid (yield: 100%).

The obtained lithium ethyl (cyanomethyl)phosphonate was subjected to $^1$H-NMR measurement, thereby confirming a structure thereof. The results are shown below.

$^1$H-NMR (400 MHz, DMSO-$d_6$): δ3.82 (quintet, J=7.1 Hz, 2H), 2.54 (d, J=18 Hz, 2H), 1.14 (t, J=7.0 Hz, 3H)

Examples III-1 to III-27 and Comparative Examples III-1 to III-3

[Production of Lithium Ion Secondary Battery]

94 mass % of $LiNi_{1/3}Mn_{1/3}Co_{1/3}O_2$ and 3 mass % of acetylene black (electroconductive agent) were mixed and then added to and mixed with a solution which had been prepared by dissolving 3 mass % of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby producing a positive electrode sheet. A density of the positive electrode except for the collector was 3.6 g/cm$^3$. In addition, 10 mass % of silicon (elemental substance), 80 mass % of artificial graphite ($d_{002}$=0.335 nm, negative electrode active material), and 5 mass % of acetylene black (electroconductive agent) were mixed and then added to and mixed with a solution which had been prepared by dissolving 5 mass % of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet. A density of the negative electrode except for the collector was 1.5 g/cm³. In addition, the electrode sheet was analyzed by X-ray diffractometry, and a ratio [I(110)/I(004)] of the peak intensity I(110) of the (110) plane to the peak intensity I(004) of the (004) plane of the graphite crystal was 0.1. The positive electrode sheet, a micro-porous polyethylene-made film separator, and the negative electrode sheet were laminated in this order, and the nonaqueous electrolytic solution having each of compositions shown in Tables 20 to 23 was added, thereby producing a 2032-type coin battery.

[Evaluation of Low-Temperature Properties after High-Temperature Charged Storage]

<Initial Discharge Capacity>

The initial discharge capacity at −10° C. was determined in the same manner as in Example I-1.

<High-Temperature Charged Storage Test>

The high-temperature charged storage test was performed in the same manner as in Example I-1.

<Discharge Capacity after High-Temperature Charged Storage>

The discharge capacity at −10° C. after the high-temperature charged storage was determined in the same manner as in Example I-1.

<Low-Temperature Properties after High-Temperature Charged Storage>

The discharge capacity retention rate (%) at −10° C. after the high-temperature charged storage was determined in the same manner as in Example I-1.

The battery characteristics are shown in Tables 20 to 22.

TABLE 20

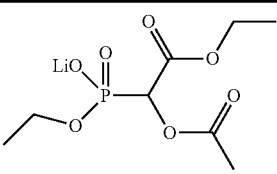

TABLE 21

| | Composition of electrolyte salt Composition of nonaqueous electrolytic solution (volume ratio of solvent) | Compound of general formula (III) | | Discharge capacity retention rate at −10° C. after high-temperature charged storage at 65° C. (%) |
|---|---|---|---|---|
| | | Kind | Content in nonaqueous electrolytic solution (mass %) | |
| Example III-11 | 1.0M LiPF6 EC/VC/DMC/MEC (29/1/40/30) | 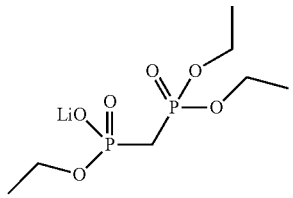 | 1 | 71 |
| Example III-12 | 1.0M LiPF6 EC/VC/DMC/MEC (29/1/40/30) | 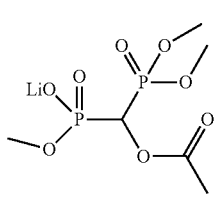 | 1 | 73 |
| Example III-13 | 1.0M LiPF6 EC/VC/DMC/MEC (29/1/40/30) | 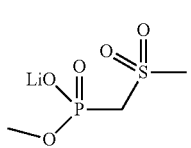 | 1 | 65 |
| Example III-14 | 1.0M LiPF6 EC/VC/DMC/MEC (29/1/40/30) | 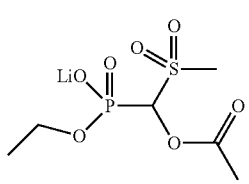 | 1 | 68 |
| Example III-15 | 1.0M LiPF6 EC/VC/DMC/MEC (29/1/40/30) | 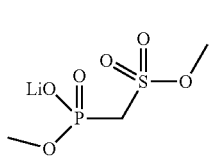 | 1 | 64 |
| Example III-16 | 1.0M LiPF6 EC/VC/DMC/MEC (29/1/40/30) | 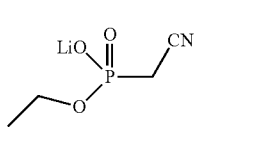 | 1 | 62 |
| Example III-17 | 1.0M LiPF6 EC/VC/DMC/MEC (29/1/40/30) | 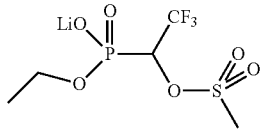 | 1 | 67 |
| Example III-18 | 1.0M LiPF6 EC/VC/DMC/MEC (29/1/40/30) | 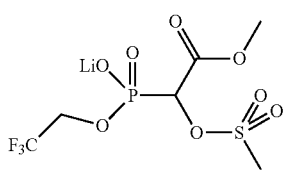 | 1 | 71 |

TABLE 21-continued

| | Composition of electrolyte salt Composition of nonaqueous electrolytic solution (volume ratio of solvent) | Compound of general formula (III) | | Discharge capacity retention rate at −10° C. after high-temperature charged storage at 65° C. (%) |
|---|---|---|---|---|
| | | Kind | Content in nonaqueous electrolytic solution (mass %) | |
| Example III-19 | 1.0M LiPF6 EC/VC/DMC/MEC (29/1/40/30) | [structure with LiO-P(=O)(O-CH2-C≡CH)-CH(OC(=O)CH3)-C(=O)-O-CH3] | 1 | 73 |
| Example III-20 | 1.0M LiPF6 EC/VC/DMC/MEC (29/1/40/30) | [structure with LiO-P(=O)(OEt)-CH(O-S(=O)2-C6H5)-C(=O)-O-CH3] | 1 | 70 |

TABLE 22

| | Composition of electrolyte salt Composition of nonaqueous electrolytic solution (volume ratio of solvent) | Compound of general formula (III) | | Discharge capacity retention rate at −10° C. after high-temperature charged storage at 65° C. (%) |
|---|---|---|---|---|
| | | Kind | Content in nonaqueous electrolytic solution (mass %) | |
| Example III-21 | 1.0M LiPF6 EC/VC/DMC/MEC (29/1/40/30) | [structure with LiO-P(=O)(OEt)-CH2-CH(OC(=O)CH3)-C(=O)-O-CH3] | 1 | 68 |
| Example III-22 | 1.0M LiPF6 EC/VC/DMC/MEC (29/1/40/30) | [structure with LiO-P(=O)(OEt)-CH2-CH2-P(=O)(OEt)2] | 1 | 70 |
| Example III-23 | 1.0M LiPF6 EC/VC/DMC/MEC (29/1/40/30) | [structure with LiO-P(=O)(OEt)-CH2-CH2-S(=O)2-OCH3] | 1 | 63 |

TABLE 23

| | Composition of electrolyte salt Composition of nonaqueous electrolytic solution (volume ratio of solvent) | Compound of general formula (III) Kind | Content in nonaqueous electrolytic solution (mass %) | Discharge capacity retention rate at −10° C. after high-temperature charged storage at 65° C. (%) |
|---|---|---|---|---|
| Example III-24 | 1.0M LiPF6 + 0.05M LiBOB EC/FEC/VC/DMC/MEC (19/10/1/40/30) | 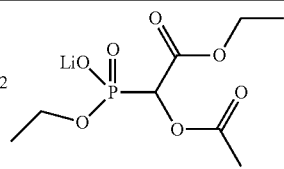 | 1 | 77 |
| Example III-25 | 1.0M LiPF6 + 0.05M LiPO2F2 EC/FEC/GBL/VC/DMC/MEC (19/7/3/1/40/30) | | 1 | 78 |
| Example III-26 | 1.0M LiPF6 + 0.05M LMS EC/FEC/VC/DMC/MEC/EA (19/10/1/40/20/10) | | 1 | 80 |
| Example III-27 | 0.7M LiPF6 + 0.3M LiFSI EC/VC/DMC/MEC (29/1/40/30) | | 1 | 79 |
| Comparative Example III-1 | 1.0M LiPF6 EC/VC/DMC/MEC (29/1/40/30) | None | — | 51 |
| Comparative Example III-2 | 1.01M LiPF6 EC/VC/DMC/MEC (29/1/40/30) |  | 1 | 56 |
| Comparative Example III-3 | 1.01M LiPF6 EC/VC/DMC/MEC (29/1/40/30) |  | 1 | 53 |

Example III-28 and Comparative Example III-4

A positive electrode sheet was produced by using $LiNi_{1/2}Mn_{3/2}O_4$ (positive electrode active material) in place of the positive electrode active material used in Example III-1. 94 mass % of $LiNi_{1/2}Mn_{3/2}O_4$ coated with amorphous carbon and 3 mass % of acetylene black (electroconductive agent) were mixed and then added to and mixed with a solution which had been prepared by dissolving 3 mass % of polyvinylidene fluoride (binder) in 1-methyl-2-pyrrolidone in advance, thereby preparing a positive electrode mixture paste. A coin battery was produced and subjected to battery evaluation in the same manners as in Example III-1, except that this positive electrode mixture paste was applied onto one surface of an aluminum foil (collector), dried, and treated under pressure, followed by cutting into a predetermined size, thereby producing a positive electrode sheet; that in evaluating the battery, the final charging voltage and the final discharging voltage were set to 4.9 V and 2.7 V, respectively; and that the composition of the nonaqueous electrolytic solution was changed to a predetermined composition. The results are shown in Table 24.

TABLE 24

| | Composition of electrolyte salt Composition of nonaqueous electrolytic solution (volume ratio of solvent) | Compound of general formula (III) Kind | Content in nonaqueous electrolytic solution (mass %) | Discharge capacity retention rate at −10° C. after high-temperature charged storage at 65° C. (%) |
|---|---|---|---|---|
| Example III-28 | 1.0M LiPF6 EC/FEC/MEC/DEC (20/10/40/30) | 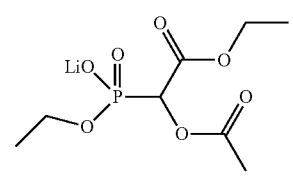 | 1 | 70 |
| Comparative Example III-4 | | None | — | 44 |

Example III-29 and Comparative Example III-5

A negative electrode sheet was produced by using lithium titanate $Li_4Ti_5O_{12}$ (negative electrode active material) in place of the negative electrode active material used in Example III-1. 80 mass % of lithium titanate $Li_4Ti_5O_{12}$ and 15 mass % of acetylene black (electroconductive agent) were mixed and then added to and mixed with a solution which had been prepared by dissolving 5 mass % of polyvinylidene fluoride (binder) in 1-methyl-2-pyrrolidone in advance, thereby preparing a negative electrode mixture paste. A coin battery was produced and subjected to battery evaluation in the same manners as in Example III-1, except that this negative electrode mixture paste was applied onto one surface of a copper foil (collector), dried, and treated under pressure, followed by cutting into a predetermined size, thereby producing a negative electrode sheet; that in evaluating the battery, the final charging voltage and the final discharging voltage were set to 2.8 V and 1.2 V, respectively; and that the composition of the nonaqueous electrolytic solution was changed to a predetermined composition. The results are shown in Table 25.

TABLE 25

| | Composition of electrolyte salt Composition of nonaqueous electrolytic solution (volume ratio of solvent) | Compound of general formula (III) | | Discharge capacity retention rate at −10° C. after high-temperature charged storage at 65° C. (%) |
|---|---|---|---|---|
| | | Kind | Content in nonaqueous electrolytic solution (mass %) | |
| Example III-29 | 1.0M LiPF6 PC/DEC (30/70) | 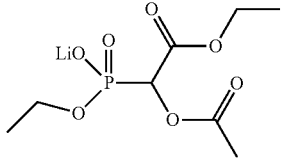 | 1 | 83 |
| Comparative Example III-5 | | None | — | 61 |

Examples III-30 and III-31

Lithium secondary batteries were produced and subjected to battery evaluation in the same manners as in Comparative Example III-1, except for using a positive electrode produced by adding a predetermined amount of the compound represented by the general formula (III) with the total mass of the positive electrode active material being taken as 100. The results are shown in Table 26.

Examples III-32 and III-33

Lithium secondary batteries were produced and subjected to battery evaluation in the same manners as in Comparative Example III-1, except for not adding the compound represented by the general formula (III) to the positive electrode and using a negative electrode produced by adding a predetermined amount of the compound represented by the general formula (III) with the total mass of the negative electrode active material being taken as 100. The results are shown in Table 26.

TABLE 26

| | Composition of electrolyte salt Composition of nonaqueous electrolytic solution (volume ratio of solvent) | Compound of general formula (III) | | Addition part | Content in positive electrode or negative electrode active material (mass %) | Discharge capacity retention rate at −10° C. after high-temperature charged storage at 65° C. (%) |
| --- | --- | --- | --- | --- | --- | --- |
| | | Kind | | | | |
| Example III-30 | 1.0M LiPF6 EC/VC/DMC/MEC (29/1/40/30) | 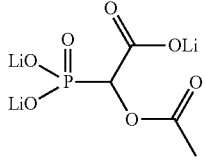 | | Positive electrode | 0.3 | 72 |
| Example III-31 | | 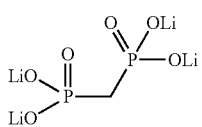 | | | 0.3 | 75 |
| Example III-32 | | 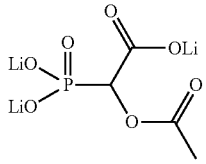 | | Negative electrode | 0.3 | 63 |
| Example III-33 | | 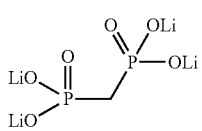 | | | 0.3 | 67 |

All of the lithium secondary batteries of Examples III-1 to III-27 as described above are remarkably improved in the electrochemical characteristics in a broad temperature range, as compared with the lithium secondary batteries of Comparative Example III-1 which is in the case of not adding the compound represented by the general formula (III), in which the specified polar group (X) is bound to the phosphorus atom (P), Comparative Example III-2 which is in the case of adding triethyl phosphonoacetate, and Comparative Example III-3 which is in the case of adding phosphonoacetate, in the nonaqueous electrolytic solution of the present invention. In the light of the above, it has become clear that in the nonaqueous electrolytic solution having an electrolyte salt dissolved in a nonaqueous solvent, the effects of the present invention are peculiar effects brought in the case of containing the compound of the present invention, in which the specified polar group (X) is bound to the phosphorus atom (P).

In addition, from the comparison of Example III-28 with Comparative Example III-4 and the comparison of Example III-29 with Comparative Example III-5 in the case of using lithium nickel manganate (LiNi$_{1/2}$Mn$_{3/2}$O$_4$) for the positive electrode and also in the case of using lithium titanate for the negative electrode, the same effects are brought. In consequence, it is evident that the effects of the present invention according to the third invention are not an effect relying upon a specified positive electrode or negative electrode.

In addition, from the comparison of Examples III-30 to III-33 with Comparative Example III-1, it has become clear that the effects of the present invention are brought even in the case of containing the compound represented by the general formula (III), in which the specified polar group (X) is bound to the phosphorus atom (P) in other part than the electrolytic solution.

Furthermore, the nonaqueous electrolytic solution of the third invention also has an effect for improving the discharging properties in the case of using a lithium primary battery in a broad temperature range.

INDUSTRIAL APPLICABILITY

By using the nonaqueous electrolytic solution containing the compound according to the present invention, in which a polar group is bound to a phosphorus atom, it is possible to obtain an energy storage device which is excellent in electrochemical characteristics in a broad temperature range. In particular, when the nonaqueous electrolytic solution according to the present invention is used as a nonaqueous electrolytic solution for an energy storage device, such as a lithium secondary battery to be mounted in a hybrid electric vehicle, a plug-in hybrid electric vehicle, a battery electric vehicle, and so on, it is possible to obtain an energy storage device in which the electrochemical characteristics in a broad temperature range are hardly worsened.

In addition, as for the novel compound of the present invention, in view of its special structure, it is useful as materials for an electrolyte application, a heat resistance application, etc. in the fields of general chemistry, particularly organic chemistry, electrochemistry, biochemistry, and polymer chemistry, and also useful as intermediate raw materials of drugs, agricultural chemicals, electronic materials, polymer materials, and the like or a battery material.

The invention claimed is:

1. A nonaqueous electrolytic solution, comprising an electrolyte salt dissolved in a nonaqueous solvent, the nonaqueous electrolytic solution comprising a lithium phosphate of formula (I), in which a polar group ($X^1$) is bound directly to a phosphorus atom (P):

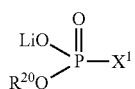
(I)

wherein, $R^{20}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^1$ is a polar group (i) containing a —C(=O) group, a —P(=O) group, or an —S(=O)$_2$ group.

2. The nonaqueous electrolytic solution according to claim 1, wherein the lithium phosphate is at least one lithium phosphate of any of formulae (I-II) to (I-IV):

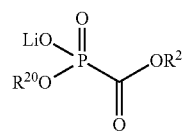
(I-II)

wherein, $R^1$ and $R^2$ are each independently synonymous with $R^{20}$,

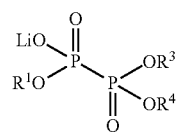
(I-III)

wherein, $R^1$, $R^3$, and $R^4$ are each independently synonymous with $R^{20}$, and

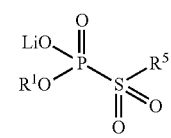
(I-IV)

wherein, $R^1$ and $R^5$ are each independently synonymous with $R^{20}$.

3. An energy storage device comprising a positive electrode, a negative electrode, and the nonaqueous electrolytic solution according to claim 1.

4. The energy storage device according to claim 3, wherein the electrolyte salt comprises at least one selected from the group consisting of LiPF$_6$, LiBF$_4$, LiN(SO$_2$CF$_3$)$_2$, LiN(SO$_2$C$_2$F$_5$)$_2$, and LiN(SO$_2$F)$_2$ in a concentration of 0.3 M or more and 2.5 M or less.

5. The energy storage device according to claim 3, which comprises a complex metal oxide comprising lithium and at least one selected from the group consisting of cobalt, manganese, and nickel and/or a lithium-containing olivine-type phosphate comprising at least one selected from the group consisting of iron, cobalt, nickel, and manganese, as a positive electrode active material.

6. The energy storage device according to claim 3, which comprises at least one selected from the group consisting of metal lithium, a lithium alloy, a carbon material capable of absorbing and releasing lithium, tin, a tin compound, silicon, a silicon compound, and a lithium titanate compound, as a negative electrode active material.

7. The nonaqueous electrolyte solution according to claim 1, wherein the lithium phosphate is any one of formulae (I-V) to (I-VII), in which a polar group is bound directly to a phosphorus atom (P):

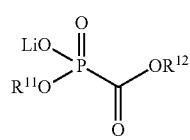
(I-V)

wherein, $R^{11}$ and $R^{12}$ are each independently synonymous with $R^{20}$, provided that at least one of $R^{11}$ and $R^{12}$ is an alkynyl group having 3 to 6 carbon atoms,

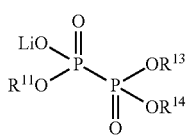
(I-VI)

wherein, $R^{11}$, $R^{13}$, and $R^{14}$ are each independently synonymous with $R^{20}$, provided that the case where all of $R^{11}$, $R^{13}$, and $R^{14}$ are a lithium atom is excluded, and

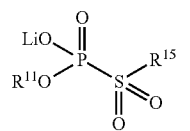
(I-VII)

wherein, $R^{11}$ and $R^{15}$ are each independently synonymous with $R^{20}$.

8. A nonaqueous electrolytic solution, comprising an electrolyte salt dissolved in a nonaqueous solvent, the nonaqueous electrolytic solution comprising a compound of formula (II), in which a cyclic polar group ($X^2$) is bound directly to a phosphorus atom (P):

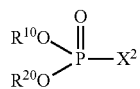
(II)

wherein, $R^{10}$ and $R^{20}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^2$ is a 4- to 7-membered ring polar group (iii) containing a —C(=O)—O— group or a —C(=O)—N— group, provided that when $X^2$ is a 4- to 7-membered ring polar group containing a —C(=O)—N— group, at least one of $R^{10}$ and $R^{20}$ is a lithium atom.

9. The nonaqueous electrolytic solution according to claim 8, wherein in formula (II), at least of $R^{10}$ and $R^{20}$ is a lithium atom.

10. The nonaqueous electrolytic solution according to claim 8, wherein the compound of formula (II) is at least one compound of any of formulae (II-I) to (II-VI), in which a cyclic polar group is bound directly to a phosphorus atom (P):

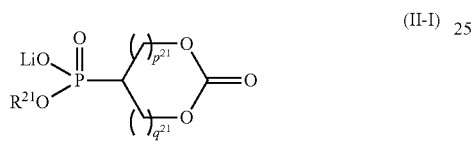
(II-I)

wherein, $R^{21}$ is synonymous with $R^{20}$; and $p^{21}$ and $q^{21}$ each independently represent an integer of 0 to 2 and satisfy a relation: $1\leq(p^{21}+q^{21})\leq3$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented by the following general formula (I-VII),

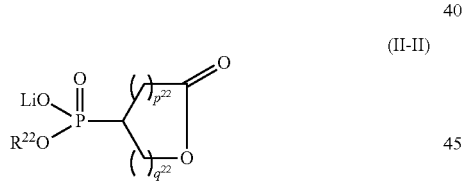
(II-II)

wherein, $R^{22}$ is synonymous with $R^{20}$; and $p^{22}$ and $q^{22}$ each independently represent an integer of 0 to 3 and satisfy a relation: $1\leq(p^{22}+q^{22})\leq4$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (II-VII),

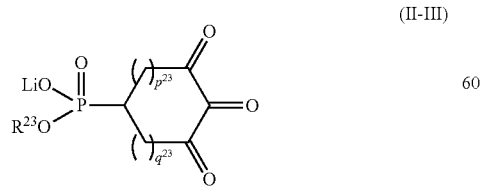
(II-III)

wherein, $R^{23}$ is synonymous with $R^{20}$; and $p^{23}$ and $q^{23}$ each independently represent an integer of 0 to 2 and satisfy a relation: $1\leq(p^{23}+q^{23})\leq3$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (II-VII),

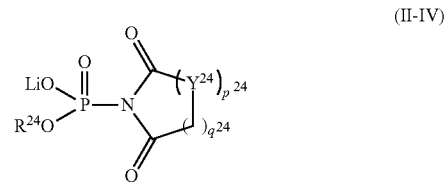
(II-IV)

wherein, $R^{24}$ is synonymous with $R^{20}$; $Y^{24}$ represents an —NH— group or an —O— group; $p^{24}$ represents an integer of 0 to 1; $q^{24}$ represents an integer of 1 to 4; and $p^{24}$ and $q^{24}$ satisfy a relation: $2\leq(p^{24}+q^{24})\leq4$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (II-VII),

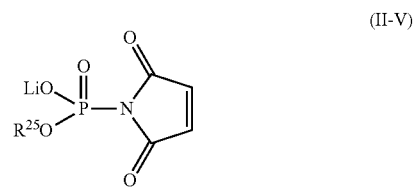
(II-V)

wherein, $R^{25}$ is synonymous with $R^{20}$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (II-VII),

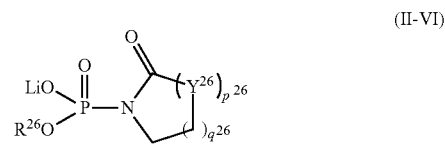
(II-VI)

wherein, $R^{26}$ is synonymous with $R^{20}$; $Y^{26}$ represents an —NH— group or an —O— group; $p^{26}$ represents an integer of 0 to 1; $q^{26}$ represents an integer of 1 to 4; and $p^{26}$ and $q^{26}$ satisfy a relation $2\leq(p^{26}+q^{26})\leq4$, provided that in the cyclic polar group, a part of hydrogen atoms may be substituted with a halogen atom, an alkyl group having 1 to 8 carbon atoms, a haloalkyl group having 1 to 8 carbon atoms, or a substituent represented of formula (II-VII), and

(II-VII)

wherein, $R^{27}$ and $R^{28}$ are each independently synonymous with $R^{20}$; and * represents a site binding to the cyclic polar group.

11. The nonaqueous electrolytic solution according to claim 8, wherein the compound of formula (II) is at least one selected from the group consisting of compounds of any of formulae (V-I) to (V-III), in which a cyclic polar group is bound directly to a phosphorus atom (P):

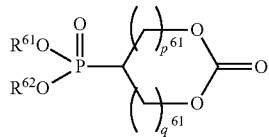

(V-I)

wherein, $R^{61}$ and $R^{62}$ are each independently an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom; and $p^{61}$ and $q^{61}$ each independently represent an integer of 0 to 2 and satisfy a relation: $1 \leq (p^{61}+q^{61}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (V-IV),

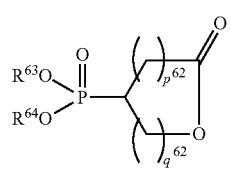

(V-II)

wherein, $R^{63}$ and $R^{64}$ are each independently synonymous with $R^{61}$ and $R^{62}$, respectively; and $p^{62}$ and $q^{62}$ each independently represent an integer of 0 to 3 and satisfy a relation: $1 \leq (p^{62}+q^{62}) \leq 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (V-IV),

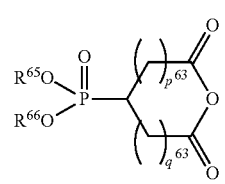

(V-III)

wherein, $R^{65}$ and $R^{66}$ are each independently synonymous with $R^{61}$ and $R^{62}$, respectively; and $p^{63}$ and $q^{63}$ each independently represent an integer of 0 to 2 and satisfy a relation: $1 \leq (p^{63}+q^{63}) \leq 3$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (V-IV), and

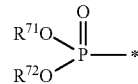

(V-IV)

wherein, $R^{71}$ and $R^{72}$ are each independently synonymous with $R^{61}$ and $R^{62}$, respectively.

12. An energy storage device comprising a positive electrode, a negative electrode, and the nonaqueous electrolytic solution according to claim 8.

13. The energy storage device according to claim 12, wherein the electrolyte salt comprises at least one selected from the group consisting of $LiPF_6$, $LiBF_4$, $LiN(SO_2CF_3)_2$, $LiN(SO_2C_2F_5)_2$, and $LiN(SO_2F)_2$ in a concentration of 0.3 M or more and 2.5 M or less.

14. The energy storage device according to claim 12, which comprises a complex metal oxide comprising lithium and at least one selected from the group consisting of cobalt, manganese, and nickel and/or a lithium-containing olivine-type phosphate comprising at least one selected from the group consisting of iron, cobalt, nickel, and manganese, as a positive electrode active material.

15. The energy storage device according to claim 12, which comprises at least one selected from the group consisting of metal lithium, a lithium alloy, a carbon material capable of absorbing and releasing lithium, tin, a tin compound, silicon, a silicon compound, and a lithium titanate compound, as a negative electrode active material.

16. A nonaqueous electrolytic solution, comprising an electrolyte salt dissolved in a nonaqueous solvent, the nonaqueous electrolytic solution comprising a compound of formula (III), in which a polar group ($X^3$) is bound to a phosphorus atom (P):

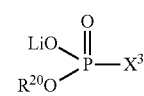

(III)

wherein, $R^{20}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and $X^3$ is a polar group containing a —C(=O) group, a —P(=O) group, an —S(=O)$_2$ group, a —CN group, or an alkyl group having 1 to 6 carbon atoms, in which a part of hydrogen atoms is substituted with a fluorine atom.

17. The nonaqueous electrolytic solution according to claim 16, wherein the compound of formula (III) is at least one compound of any of formulae (III-1) to (III-7):

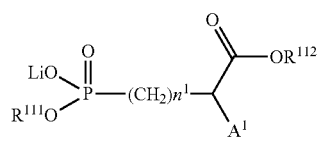

(III-1)

wherein, $A^1$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{113}$ group, an —OC(=O)—O$R^{114}$ group, an —S(=O)$_2R^{115}$ group, or an —S(=O)$_2$O$R^{116}$ group; $R^{111}$, $R^{114}$, and $R^{116}$ each independently represent an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; $R^{112}$, $R^{113}$, and $R^{115}$ each represent an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atoms; and $n^1$ represents an integer of 0 to 2,

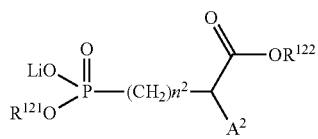
(III-2)

wherein, $A^2$ represents an alkoxy group having 1 to 8 carbon atoms, in which a part of hydrogen atoms may be substituted with a halogen atom, an —OC(=O)$R^{123}$ group, an —OC(=O)—O$R^{124}$ group, an —S(=O)$_2R^{125}$ group, or an —S(=O)$_2$O$R^{126}$ group; $R^{121}$, $R^{122}$, $R^{124}$, and $R^{126}$ are each independently synonymous with $R^{20}$; $R^{123}$ and $R^{125}$ are each independently synonymous with $R^{113}$ and $R^{115}$, respectively; and $n^2$ represents an integer of 0 to 2,

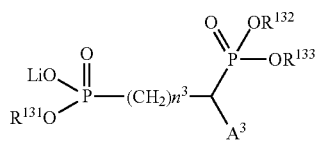
(III-3)

wherein, $A^3$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{134}$ group, an —OC(=O)—O$R^{135}$ group, an —S(=O)$_2R^{136}$ group, or an —S(=O)$_2$O$R^{137}$ group; $R^{131}$, $R^{132}$, $R^{133}$, $R^{135}$, and $R^{137}$ are each independently synonymous with $R^{20}$; $R^{134}$ and $R^{136}$ are each independently synonymous with $R^{113}$ and $R^{115}$, respectively; and $n^3$ represents an integer of 0 to 2,

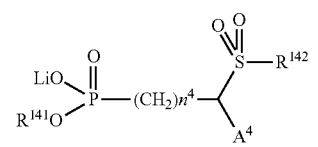
(III-4)

wherein, $A^4$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{143}$ group, an —OC(=O)—O$R^{144}$ group, an —S(=O)$_2R^{145}$ group, or an —S(=O)$_2$O$R^{146}$ group; $R^{141}$, $R^{144}$, and $R^{146}$ are each independently synonymous with $R^{20}$; $R^{142}$, $R^{143}$, and $R^{145}$ are each independently synonymous with $R^{113}$ and $R^{115}$, respectively; and $n^4$ represents an integer of 0 to 2,

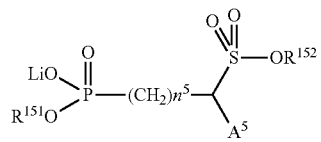
(III-5)

wherein, $A^5$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{153}$ group, an —OC(=O)—O$R^{154}$ group, an —S(=O)$_2R^{155}$ group, or an —S(=O)$_2$O$R^{156}$ group; $R^{151}$, $R^{152}$, $R^{154}$, and $R^{156}$ are each independently synonymous with $R^{20}$; $R^{153}$ and $R^{155}$ are each independently synonymous with $R^{113}$ and $R^{115}$, respectively; and $n^5$ represents an integer of 0 to 2,

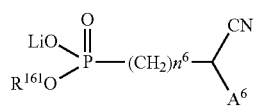
(III-6)

wherein, $A^6$ represents a hydrogen atom, a halogen atom, an alkyl group having 1 to 8 carbon atoms, in which a part of hydrogen atoms may be substituted with a halogen atom, an alkoxy group having 1 to 8 carbon atoms, in which a part of hydrogen atoms may be substituted with a halogen atom, an —OC(=O)$R^{162}$ group, an —OC(=O)—O$R^{163}$ group, an —S(=O)$_2R^{164}$ group, or an —S(=O)$_2$O$R^{165}$ group; $R^{161}$, $R^{163}$, and $R^{165}$ are each independently synonymous with $R^{20}$; $R^{162}$ and $R^{164}$ are each independently synonymous with $R^{113}$ and $R^{115}$, respectively; and $n^6$ represents an integer of 0 to 2, and

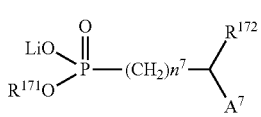
(III-7)

wherein, $R^{172}$ represents an alkyl group having 1 to 6 carbon atoms, in which a part of hydrogen atoms are substituted with a fluorine atom; $A^7$ represents an alkoxy group having 1 to 8 carbon atoms, in which a part of hydrogen atoms may be substituted with a halogen atom, an —OC(=O)R$^{173}$ group, an —OC(=O)—OR$^{174}$ group, an —S(=O)$_2$R$^{175}$ group, or an —S(=O)$_2$OR$^{176}$ group; R$^{171}$, R$^{174}$, and R$^{176}$ are each independently synonymous with R$^{20}$; R$^{173}$ and R$^{175}$ are each independently synonymous with R$^{113}$ and R$^{115}$, respectively; and n$^7$ represents an integer of 0 to 2.

18. An energy storage device comprising a positive electrode, a negative electrode, and the nonaqueous electrolytic solution being the nonaqueous electrolytic solution according to claim 16.

19. The energy storage device according to claim 18, wherein the electrolyte salt comprises at least one selected from the group consisting of LiPF$_6$, LiBF$_4$, LiN(SO$_2$CF$_3$)$_2$, LiN(SO$_2$C$_2$F$_5$)$_2$, and LiN(SO$_2$F)$_2$ in a concentration of 0.3 M or more and 2.5 M or less.

20. The energy storage device according to claim 18, which comprises a complex metal oxide comprising lithium and at least one selected from the group consisting of cobalt, manganese, and nickel and/or a lithium-containing olivine-type phosphate comprising at least one selected from the group consisting of iron, cobalt, nickel, and manganese, as a positive electrode active material.

21. The energy storage device according to claim 18, which comprises at least one selected from the group consisting of metal lithium, a lithium alloy, a carbon material capable of absorbing and releasing lithium, tin, a tin compound, silicon, a silicon compound, and a lithium titanate compound, as a negative electrode active material.

22. A lithium phosphate of any one of formulae (IV-I) to (IV-VI), in which a cyclic polar group is bound directly to a phosphorus atom (P):

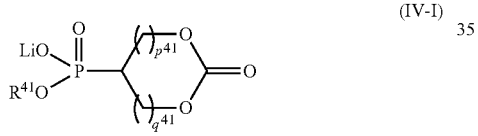

(IV-I)

wherein, R$^{41}$ is an organic group selected from the group consisting of an alkyl group having 1 to 8 carbon atoms, an alkenyl group having 2 to 6 carbon atoms, an alkynyl group having 3 to 6 carbon atoms, and an aryl group having 6 to 12 carbon atoms, in each of which a part of hydrogen atoms may be substituted with a halogen atom, or a lithium atom; and p$^{41}$ and q$^{41}$ each independently represent an integer of 0 to 2 and satisfy a relation: 1≤(p$^{41}$+q$^{41}$)≤3, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (IV-VII),

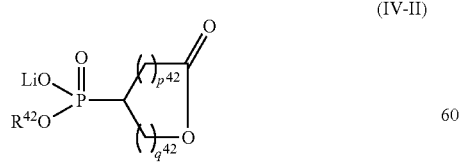

(IV-II)

wherein, R$^{42}$ is synonymous with R$^{41}$; and p$^{42}$ and q$^{42}$ each independently represent an integer of 0 to 3 and satisfy a relation: 1≤(p$^{42}$+q$^{42}$)≤4, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (IV-VII),

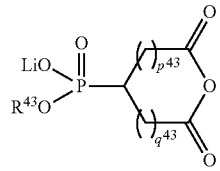

(IV-III)

wherein, R$^{43}$ is synonymous with R$^{41}$; and p$^{43}$ and q$^{43}$ each independently represent an integer of 0 to 2 and satisfy a relation: 1≤(p$^{43}$+q$^{43}$)≤3, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (IV-VII),

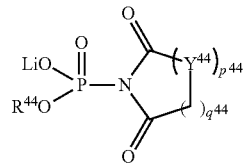

(IV-IV)

wherein, R$^{44}$ is synonymous with R$^{41}$; Y$^{44}$ represents an —NH— group or an —O— group; p$^{44}$ represents an integer of 0 to 1; q$^{44}$ represents an integer of 1 to 4; and p$^{44}$ and q$^{44}$ satisfy a relation: 2≤(p$^{44}$+q$^{44}$)≤4, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (IV-VII),

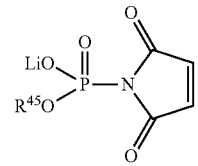

(IV-V)

wherein, R$^{45}$ is synonymous with R$^{41}$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (IV-VII),

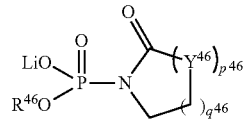

(IV-VI)

wherein, R$^{46}$ is synonymous with R$^{41}$; Y$^{46}$ represents an —NH— group or an —O— group; p$^{46}$ represents an integer of 0 to 1; $q^{46}$ represents an integer of 1 to 4; and $p^{46}$ and $q^{46}$ satisfy a relation: $2 \leq (p^{46}+q^{46}) \leq 4$, provided that in the cyclic polar group, a part of hydrogen atoms may be substituted with a halogen atom, an alkyl group having 1 to 8 carbon atoms, a haloalkyl group having 1 to 8 carbon atoms, or a substituent of formula (IV-VII), and

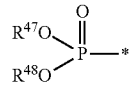
(IV-VII)

wherein, $R^{47}$ and $R^{48}$ are each independently synonymous with $R^{41}$; and * represents a site binding to the cyclic polar group.

* * * * *